US010251423B2

(12) United States Patent
Mamoun et al.

(10) Patent No.: US 10,251,423 B2
(45) Date of Patent: Apr. 9, 2019

(54) PROGRAMMABLE ELECTRONIC VAPORIZING APPARATUS AND SMOKING CESSATION SYSTEM

(71) Applicant: NICODART, INC., Los Angeles, CA (US)

(72) Inventors: Michael Suhayl Mamoun, Los Angeles, CA (US); Daniel Lawrence Blanchard, Los Angeles, CA (US); Arthur Lawrence Brody, Los Angeles, CA (US)

(73) Assignee: NicoDart, Inc., Los Angeles, CA (US)

( * ) Notice: Subject to any disclaimer, the term of this patent is extended or adjusted under 35 U.S.C. 154(b) by 77 days.

(21) Appl. No.: 15/021,577

(22) PCT Filed: Sep. 12, 2014

(86) PCT No.: PCT/US2014/055523
§ 371 (c)(1),
(2) Date: Mar. 11, 2016

(87) PCT Pub. No.: WO2015/038981
PCT Pub. Date: Mar. 19, 2015

(65) Prior Publication Data
US 2016/0219938 A1 Aug. 4, 2016

Related U.S. Application Data

(60) Provisional application No. 61/877,587, filed on Sep. 13, 2013.

(51) Int. Cl.
*A24F 47/00* (2006.01)
*H05B 3/00* (2006.01)
(Continued)

(52) U.S. Cl.
CPC ............ *A24F 47/008* (2013.01); *A24F 47/00* (2013.01); *G05B 15/02* (2013.01); *G05D 7/0676* (2013.01); *H05B 3/0014* (2013.01)

(58) Field of Classification Search
CPC ....... A24F 47/00; A24F 47/008; G05B 15/02; G05D 7/0676; H05B 3/0014;
(Continued)

(56) References Cited

U.S. PATENT DOCUMENTS

| 6,886,557 B2 | 5/2005 | Childers et al. |
| 2004/0084044 A1 | 5/2004 | Childers et al. |

(Continued)

FOREIGN PATENT DOCUMENTS

| CN | 1498663 A | 5/2004 |
| CN | 105722417 A | 6/2016 |

(Continued)

OTHER PUBLICATIONS

European Patent Application No. 14844115.7 extended European Search Report dated Apr. 10, 2017.
(Continued)

*Primary Examiner* — Anthony Calandra
*Assistant Examiner* — Jamel M Nelson
(74) *Attorney, Agent, or Firm* — Wilson Sonsini Goodrich & Rosati

(57) ABSTRACT

A programmable smoking cessation system includes an electronic vaporizing apparatus system, apparatus, nicotine management plan. Methods for the reduction of nicotine consumption based on the nicotine management plan to reduce or eliminate nicotine dependence. The systems, apparatuses and methods described herein utilize a digital processing device in combination with a vapor release mechanism to vaporize and blend nicotine and non-nicotine liquid substances from cartridge chambers to produce vapors configured to reduce nicotine consumption and dependence at a modulated rate over a specified period of time based on the nicotine management plan. The system and apparatus are configurable to track and report data acquired during use and provide feedback to a user and/or a clinical professional.

23 Claims, 20 Drawing Sheets

(51) Int. Cl.
*G05B 15/02* (2006.01)
*G05D 7/06* (2006.01)

(58) Field of Classification Search
CPC .......... A61M 5/16877; A61M 5/16881; A61M 5/16886; A61M 5/172; A61M 5/1723
See application file for complete search history.

(56) References Cited

U.S. PATENT DOCUMENTS

| | | | |
|---|---|---|---|
| 2011/0120482 A1* | 5/2011 | Brenneise | A24F 47/008 131/328 |
| 2011/0265806 A1* | 11/2011 | Alarcon | A24F 47/00 131/273 |
| 2012/0204889 A1 | 8/2012 | Xiu | |
| 2012/0227752 A1 | 9/2012 | Alelov | |
| 2012/0291791 A1* | 11/2012 | Pradeep | A24F 47/008 131/273 |
| 2013/0192623 A1 | 8/2013 | Tucker et al. | |

FOREIGN PATENT DOCUMENTS

| | | |
|---|---|---|
| WO | WO-2010107613 A1 | 9/2010 |
| WO | WO-2015038981 A2 | 3/2015 |

OTHER PUBLICATIONS

PCT Patent Application No. PCT/US2014/055523 International Search Report and Written Opinion dated Mar. 11, 2015.
PCT Patent Application No. PCT/US2014/055523 International Preliminary Report on Patentability dated Mar. 24, 2016.
Chinese Patent Application No. 2014800623782 First Office Action dated Feb. 5, 2018.

* cited by examiner

PROGRAMMABLE ELECTRONIC VAPORIZING APPARATUS AND SMOKING CESSATION SYSTEM

CROSS-REFERENCE

This application is filed pursuant to 35 U.S.C. § 371 as United States National Phase Application of International Application No. PCT/US2014/055523, entitled "PROGRAMMABLE ELECTRONIC VAPORIZING APPARATUS AND SMOKING CESSATION SYSTEM, which claims the benefit of U.S. Provisional Application No. 61/877,587, filed Sep. 13, 2013, each of which application is incorporated herein by reference in its entirety.

SUMMARY OF THE INVENTION

Provided herein are systems, methods, and devices (apparatuses) for the reduction of nicotine consumption based on a nicotine management plan to reduce or eliminate nicotine dependence. The systems, apparatuses and methods described herein utilize a digital processing device in combination with a vapor release mechanism to vaporize and blend nicotine and non-nicotine liquid substances from cartridge chambers to produce vapors configured to reduce nicotine consumption and dependence at a modulated rate over a specified period of time based on the nicotine management plan. The system and apparatus are configurable to track and report data acquired during use and provide feedback to a user and/or a clinical professional. The combination of the apparatus configuration and the management plan allows for fine control of the nicotine delivered to a user over time.

The nicotine management plan utilizes an electronic vaporizing apparatus system comprising an electronic controller, software and a multi-chamber cartridge or multiple cartridges to multiple vapors (nicotine based and nicotine-free; either of which could include flavorants or without flavorants), so that as a nicotine amount or percentage is gradually decreased over time, the user senses no changes in a vapor characteristic or flavor (or both), while simultaneously reducing physical dependence on nicotine.

Further, the nicotine management plan uses a software application or applications in the apparatus and/or in a controlling device (computer or smart device, for example) to establish or record or allow for input of a user's baseline nicotine behavior and usage. The software application or applications automatically or allow a user or caregiver to develop the nicotine management plan or choose a pre-set nicotine management plan. The user then uses the electronic vaporizer apparatus according to the nicotine management plan. The apparatus controls the experience for the user according to the nicotine management plan, which limits the amount or rate or percent of nicotine the user can intake for a given time, for example. The apparatus is configured to allow fine control of the nicotine deliverable or delivered to a user, thus the nicotine management plan may subtly reduce the amount of nicotine delivered to the user with little noticeable change in user experience from one day to the next, or one use to the next. The software application or applications is configured to track, record and report progress back to the user and/or a clinician (i.e. caregiver, clinical provider, physician, nurse, or other medical professional) to assist in the reinforcement of the nicotine management plan and achievement of a goal of reduction or cessation of nicotine dependence. Data which may be acquired and stored in the device memory and displayed to a user and/or clinician, and/or may be transmitted to a user or clinician wirelessly or in a wired manner comprises activity of the heater, activity of the apparatus, use durations, use time of day, flow rate, puffs per day, puffs per hour, puff volume, rate or amount of nicotine delivery per puff or per day or per hour or per week or month or a combination thereof, activity of the heater coil(s), activity of the foil heater circuit(s), date, flow intensity, power delivered to each of the heaters, duration of energization of each of the heaters, PWM profile or pulse profile, and/or airflow rate. The apparatus may comprise one or more sensor for collection of such data. While the ultimate goal may be cessation of nicotine dependence, another alternative goal may simply be reduction of nicotine usage. Thus, as used herein the systems are described as "cessation system" or "cessation systems", however, they could alternatively be called a "reduction system" or "reduction systems" in any embodiment described herein.

Provided herein is a programmable smoking cessation system comprising an electronic vaporizing apparatus comprising: a first liquid substance in a first cartridge chamber wherein the first liquid substance comprises nicotine; a second liquid substance in a second cartridge chamber; a vapor release mechanism configured to form a third vapor comprising a first vapor formed from the first liquid substance, a second vapor formed from the second liquid substance, or a combination thereof; and a digital processing device, and a nicotine management plan, wherein the system changes the third vapor formed by the vapor release mechanism according to instructions provided to the digital processing device from a computer program based on the nicotine management plan. In some embodiments of the system, in order to change the third vapor, the digital processing device is configured to modulate an amount of nicotine in the third vapor according to the nicotine management plan, an amount of nicotine in the first vapor according to the nicotine management plan, an amount of the first liquid substance in the third vapor according to the nicotine management plan, an amount of the first liquid substance in the first vapor according to the nicotine management plan, an amount of the second liquid substance in the third vapor according to the nicotine management plan, an amount of the second liquid substance in the second vapor according to the nicotine management plan, a percentage of the first liquid substance in the third vapor according to the nicotine management plan, a percentage of the second liquid substance in the third vapor according to the nicotine management plan, a percentage of nicotine in the third vapor according to the nicotine management plan, a ratio of the first liquid substance to the second substance in the third vapor according to the nicotine management plan, or a combination thereof. In some embodiments, the first liquid substance comprises a flavorant. In some embodiments, the second liquid substance comprises nicotine. In some embodiments, the second liquid substance comprises no nicotine. In some embodiments, the second liquid substance comprises a flavorant. In some embodiments, the second liquid substance comprises a non-nicotine liquid. In still other embodiments, the non-nicotine liquid is a flavorant. In some embodiments of the system, the electronic vaporizing apparatus comprises a first absorbent material in the first cartridge chamber, the second cartridge chamber, or both. In some embodiments of the system, the vapor release mechanism is configured to independently or simultaneously vaporize variable amounts of the first liquid substance and the second liquid substance. In some embodiments of the system, the vapor release mechanism comprises: a first heater coupled to a first wick, a second heater coupled to a second wick, a first control circuit coupled to the first heater, a second control circuit coupled to the second heater, and a first vaporization chamber, wherein the first wick is configured to draw the first liquid substance in proximity to or in contact with the first heater, wherein the second wick is configured to draw the second liquid substance in proximity to or in contact with the second heater, and wherein the first heater and second heater are in fluid communication with the first vaporization chamber, wherein the first control circuit and the second control circuit are part of the digital processing device, and wherein the digital processing device is configured to modulate the amount of the first liquid substance drawn by the first wick to the first heater using the first control circuit and to modulate the amount of the second liquid substance drawn by the second wick to the second heater using the second control circuit. The first heater may comprise a first heater coil configured to heat the first liquid substance in the first wick to vaporize the first liquid substance. The second heater may comprise a second heater coil configured to heat the second liquid substance in the second wick to vaporize the second liquid substance. The first heater may comprise a first foil heater circuit configured to heat the first liquid substance in the first wick (alternatively called a first wicking surface) to vaporize the first liquid substance. The second heater may comprise a second foil heater circuit configured to heat the second liquid substance in the second wick (alternatively called a second wicking surface) to vaporize the second liquid substance. In some embodiments, the vapor release mechanism comprises a first sensor that detects a volume of the first liquid substance in the first cartridge chamber. In some embodiments, the vapor release mechanism comprises a second sensor that detects a volume of the second liquid substance in the second cartridge chamber. In some embodiments, the system comprises a vaporizer housing comprising a first cartridge comprising the first cartridge chamber, a second cartridge comprising the second cartridge chamber, and the vapor release mechanism, or a third cartridge comprising the first cartridge chamber, the second cartridge chamber, and the vapor release mechanism. In some embodiments, the system comprises a durable housing comprising the digital processing device or a portion thereof. In some embodiments, the durable housing is coupled integrally with or removably from the vaporizer housing. In some embodiments of the system, the digital processing device comprises a printed circuit assembly comprising an electronic interface connection, a flow sensor analyzer, an energy control circuit, and a memory for storing the computer program for providing instruction to the digital processing device. In some embodiments of the system, the printed circuit assembly further comprises: a microprocessor, an electronic communication system for communicating with other electronic devices, and an antenna. In some embodiments of the system, the energy control circuit is configured to produce either a simple pulse or a Pulse Width Modulation output signal configured to individually meter electrical power delivered to the first heater, the second heater, or both; control a first temperature of the first heater and/or coil or foil heater circuit thereof, a second temperature the second heater and/or coil or foil heater circuit thereof, or a combination thereof and control a first rate of production of the first vapor, a second rate of production of the second vapor, or a third rate of production of the third vapor. In some embodiments, the system is configured to change the third vapor for any given puff, according to the nicotine management plan. In some embodiments, a vaporization chamber volume of the vaporization chamber corresponds to a typical puff volume. In some embodiments the vaporization chamber volume is greater than the puff volume. In some embodiments, a typical puff volume is about 15 ml to about 175 ml, about 20 ml to about 150 ml, about 15 ml to about 100 ml, about 15 ml to about 75 ml, about 20 ml to about 75 ml, about 25 ml to about 50 ml, about 25 ml, about 35 ml, about 40 ml, about 45 ml, about 50 ml, about 60 ml, 15 ml to 175 ml, 20 ml to 150 ml, 15 ml to 100 ml, 15 ml to 75 ml, 20 ml to 75 ml, 25 ml to 50 ml, 25 ml, 35 ml, 40 ml, 45 ml, 50 ml, or 60 ml. In some embodiments, the user's own typical puff volume is determined by system, or the user's own typical puff volume is provided to the system and used to adjust the nicotine in the third vapor (as amount or percentage) over time according to the management plan. In some embodiments, the system and/or apparatus is configured to provide an amount of nicotine in the third vapor (i.e. in a given 100 ml volume of the third vapor), wherein the amount of nicotine in 100 ml of third vapor is from about 0.0 mcg to about 200.0 mcg, from 0.0 mcg to 200 mcg, about 0.0 mcg to about 100.0 mcg, from 0.0 mcg to 100 mcg, from about 0.1 mcg to about 199.9 mcg, from 0.1 mcg to 199.9 mcg, from about 0.1 mcg to about 99.9 mcg, from 0.1 mcg to 99.9 mcg, from about 0.5 mcg to about 99.5 mcg, from 0.5 mcg to 99.5 mcg, from about 1.0 mcg to about 99.0 mcg, from 1.0 mcg to 99.0 mcg, from about 5.0 mcg to about 95.0 mcg, from 5.0 mcg to 95.0 mcg, from about 0.5 mcg to about 90.0 mcg, from 0.5 mcg to 90.0 mcg, from about 0.0 mcg to about 90.0 mcg, from 0.0 ml to 90.0 ml, from about 0.0 mcg to about 80.0 mcg, from about 0.5 mcg to about 80.0 mcg, from 0.5 mcg to 80.0 mcg, from 0.0 mcg to 80.0 mcg, from about 0.0 mcg to about 70.0 mcg, from 0.0 mcg to 70.0 mcg, from about 0.0 mcg to about 60.0 mcg, from 0.0 ml to 60.0 ml, from about 1.0 mcg to about 60.0 mcg, from 1.0 ml to 60.0 ml, from about 0.5 mcg to about 60.0 mcg, from 0.5 mcg to 60.0 mcg, from about 0.0 mcg to about 50.0 mcg, from 0.0 mcg to 50.0 mcg, from about 0.5 mcg to about 50.0 mcg, from 0.5 mcg to 50.0 mcg, from about 0.0 mcg to about 20 mcg, or from 0.0 mcg to 20.0 mcg. In some embodiments, the system and/or apparatus is configured to adjust the amount of nicotine in the third vapor (per 100 ml volume of the third vapor) in increments of 0.01 mcg, 0.05 mcg, 0.1 mcg, 0.15 mcg, 0.2 mcg, 0.25 mcg, 0.3 mcg, 0.35 mcg, 0.4 mcg, 0.5 mcg, 0.6 mcg, 0.7 mcg, 0.75 mcg, 0.8 mcg, 0.9 mcg, 1.0 mcg, 2.0 mcg, 3.0 mcg, 4.0 mcg, 5.0 mcg, 6.0 mcg, 7.0 mcg, 8.0 mcg, 9.0 mcg, 10.0 mcg, 11.0 mcg, 12.0 mcg, 13.0 mcg, 14.0 mcg, 15.0 mcg, 16.0 mcg, 17.0 mcg, 18.0 mcg, 19.0 mcg, 20.0 mcg, 25.0 mcg, 30.0 mcg, 40.0 mcg, 50.0 mcg, about 0.01 mcg, about 0.05 mcg, about 0.1 mcg, about 0.15 mcg, about 0.2 mcg, about 0.25 mcg, about 0.3 mcg, about 0.35 mcg, about 0.4 mcg, about 0.5 mcg, about 0.6 mcg, about 0.7 mcg, about 0.75 mcg, about 0.8 mcg, about 0.9 mcg, about 1.0 mcg, about 2.0 mcg, about 3.0 mcg, about 4.0 mcg, about 5.0 mcg, about 6.0 mcg, about 7.0 mcg, about 8.0 mcg, about 9.0 mcg, about 10.0 mcg, about 11.0 mcg, about 12.0 mcg, about 13.0 mcg, about 14.0 mcg, about 15.0 mcg, about 16.0 mcg, about 17.0 mcg, about 18.0 mcg, about 19.0 mcg, about 20.0 mcg, about 25.0 mcg, about 30.0 mcg, about 40.0 mcg, or about 50.0 mcg. In some embodiments, the system and/or apparatus is configured to provide an amount of the nicotine in the third vapor based on a typical puff volume (as defined above) or based on the user's individual puff volume as measured by the apparatus or as provided to the system, the amount of nicotine for example being from about 0.0 mcg to about 250.0 mcg, from 0.0 mcg to 250.0 mcg, about 0.0 mcg to about 100.0 mcg, from 0.0 mcg to 100.0 mcg, from about 0.5 mcg to about 100.0 mcg, from 0.5 mcg to 100.0 mcg, from about 0.5 mcg to about 90.0 mcg, from 0.5 mcg to 90.0 mcg, from about 0.0 mcg to about 75.0 mcg, from 0.0 mcg to 75.0 mcg, 0.01 mcg, 0.05 mcg, 0.1 mcg, 0.15 mcg, 0.2 mcg, 0.25 mcg, 0.3 mcg, 0.35 mcg, 0.4 mcg, 0.5 mcg, 0.6 mcg, 0.7 mcg, 0.75 mcg, 0.8 mcg, 0.9 mcg, 1.0 mcg, 2.0 mcg, 3.0 mcg, 4.0 mcg, 5.0 mcg, 6.0 mcg, 7.0 mcg, 8.0 mcg, 9.0 mcg, 10.0 mcg, 11.0 mcg, 12.0 mcg, 13.0 mcg, 14.0 mcg, 15.0 mcg, 16.0 mcg, 17.0 mcg, 18.0 mcg, 19.0 mcg, 20.0 mcg, 21.0 mcg, 22.0 mcg, 23.0 mcg, 24.0 mcg, 25.0 mcg, 26.0 mcg, 27.0 mcg, 28.0 mcg, 29.0 mcg, 30.0 mcg, 31.0 mcg, 32.0 mcg, 33.0 mcg, 34.0 mcg, 35.0 mcg, 36.0 mcg, 37.0 mcg, 38.0 mcg, 39.0 mcg, 40.0 mcg, 41.0 mcg, 42.0 mcg, 43.0 mcg, 44.0 mcg, 45.0 mcg, 46.0 mcg, 47.0 mcg, 48.0 mcg, 49.0 mcg, 50.0 mcg, 51.0 mcg, 52.0 mcg, 53.0 mcg, 54.0 mcg, 55.0 mcg, 56.0 mcg, 57.0 mcg, 58.0 mcg, 59.0 mcg, 60.0 mcg, 61.0 mcg, 62.0 mcg, 63.0 mcg, 64.0 mcg, 65.0 mcg, 66.0 mcg, 67.0 mcg, 68.0 mcg, 69.0 mcg, 70.0 mcg, 71.0 mcg, 72.0 mcg, 73.0 mcg, 74.0 mcg, 75.0 mcg, 76.0 mcg, 77.0 mcg, 78.0 mcg, 79.0 mcg, 80.0 mcg, 81.0 mcg, 82.0 mcg, 83.0 mcg, 84.0 mcg, 85.0 mcg, 86.0 mcg, 87.0 mcg, 88.0 mcg, 89.0 mcg, 90.0 mcg, 91.0 mcg, 92.0 mcg, 93.0 mcg, 94.0 mcg, 95.0 mcg, 96.0 mcg, 97.0 mcg, 98.0 mcg, 99.0 mcg, 100.0 mcg, 0 mcg to 100 mcg in increments of 0.01 mcg, 0 mcg to 100 mcg in increments of 0.1 mcg, 0 mcg to 100 mcg in increments of 0.5 mcg, 0 mcg to 100 mcg in increments of 1 mcg, 0.5 mcg to 100 mcg in increments of 0.5-5 mcg, 0.0 mcg to 100 mcg in increments of 0.5 mcg to 5 mcg, 0.0 mcg to 150 mcg in increments of 0.5 mcg to 5 mcg, 0.0 mcg to 100 mcg in increments of 0.5 mcg to 25 mcg, about 0.01 mcg, about 0.05 mcg, about 0.1 mcg, about 0.15 mcg, about 0.2 mcg, about 0.25 mcg, about 0.3 mcg, about 0.35 mcg, about 0.4 mcg, about 0.5 mcg, about 0.6 mcg, about 0.7 mcg, about 0.75 mcg, about 0.8 mcg, about 0.9 mcg, about 1.0 mcg, about 2.0 mcg, about 3.0 mcg, about 4.0 mcg, about 5.0 mcg, about 6.0 mcg, about 7.0 mcg, about 8.0 mcg, about 9.0 mcg, about 10.0 mcg, about 11.0 mcg, about 12.0 mcg, about 13.0 mcg, about 14.0 mcg, about 15.0 mcg, about 16.0 mcg, about 17.0 mcg, about 18.0 mcg, about 19.0 mcg, about 20.0 mcg, about 21.0 mcg, about 22.0 mcg, about 23.0 mcg, about 24.0 mcg, about 25.0 mcg, about 26.0 mcg, about 27.0 mcg, about 28.0 mcg, about 29.0 mcg, about 30.0 mcg, about 31.0 mcg, about 32.0 mcg, about 33.0 mcg, about 34.0 mcg, about 35.0 mcg, about 36.0 mcg, about 37.0 mcg, about 38.0 mcg, about 39.0 mcg, about 40.0 mcg, about 41.0 mcg, about 42.0 mcg, about 43.0 mcg, about 44.0 mcg, about 45.0 mcg, about 46.0 mcg, about 47.0 mcg, about 48.0 mcg, about 49.0 mcg, about 50.0 mcg, about 51.0 mcg, about 52.0 mcg, about 53.0 mcg, about 54.0 mcg, about 55.0 mcg, about 56.0 mcg, about 57.0 mcg, about 58.0 mcg, about 59.0 mcg, about 60.0 mcg, about 61.0 mcg, about 62.0 mcg, about 63.0 mcg, about 64.0 mcg, about 65.0 mcg, about 66.0 mcg, about 67.0 mcg, about 68.0 mcg, about 69.0 mcg, about 70.0 mcg, about 71.0 mcg, about 72.0 mcg, about 73.0 mcg, about 74.0 mcg, about 75.0 mcg, about 76.0 mcg, about 77.0 mcg, about 78.0 mcg, about 79.0 mcg, about 80.0 mcg, about 81.0 mcg, about 82.0 mcg, about 83.0 mcg, about 84.0 mcg, about 85.0 mcg, about 86.0 mcg, about 87.0 mcg, about 88.0 mcg, about 89.0 mcg, about 90.0 mcg, about 91.0 mcg, about 92.0 mcg, about 93.0 mcg, about 94.0 mcg, about 95.0 mcg, about 96.0 mcg, about 97.0 mcg, about 98.0 mcg, about 99.0 mcg, about 100.0 mcg, about 0 mcg to about 100 mcg in increments of 0.01 mcg, about 0 mcg to about 100 mcg in increments of 0.1 mcg, about 0 mcg to about 100 mcg in increments of 0.5 mcg, about 0 mcg to about 100 mcg in increments of 1 mcg, about 0.5 mcg to about 100 mcg in increments of 0.5-5 mcg, about 0.0 mcg to about 100 mcg in increments of 0.5 mcg to 5 mcg, about 0.0 mcg to about 150 mcg in increments of 0.5 mcg to 5 mcg, or about 0.0 mcg to about 100 mcg in increments of 0.5 mcg to 25 mcg. In some embodiments, the system and/or apparatus is configured to modulate or adjust the amount of nicotine in the third vapor in increments of 1.0 mcg, 5.0 mcg, 10.0 mcg, 20.0 mcg, 25.0 mcg, 30.0 mcg, 40.0 mcg, 50.0 mcg, 75.0 mcg, 100.0 mcg, 150.0 mcg, 200.0 mcg, 250.0 mcg, about 1.0 mcg, about 5.0 mcg, about 10.0 mcg, about 20.0 mcg, about 25.0 mcg, about 30.0 mcg, about 40.0 mcg, about 50.0 mcg, about 75.0 mcg, about 100.0 mcg, about 150.0 mcg, about 200.0 mcg, about 250.0 mcg, less than 250.0 mcg, less than 200.0 mcg, less than 150.0 mcg, less than 100.0 mcg, less than 75.0 mcg, less than 50.0 mcg, less than 40.0 mcg, less than 30.0 mcg, less than 25.0 mcg, less than 20.0 mcg, less than 10.0 mcg, less than 5.0 mcg, greater than about 5.0 mcg, greater than about 10.0 mcg, greater than about 20.0 mcg, greater than about 25.0 mcg, greater than about 30.0 mcg, greater than about 40.0 mcg, greater than about 50.0 mcg, greater than about 75.0 mcg, greater than about 100.0 mcg, greater than about 150.0 mcg, greater than about 200.0 mcg and greater than about 250.0 mcg. In some embodiments, the system and/or apparatus is configured to modulate the percentage of nicotine in the third vapor from about 0% to about 100%, from 0% to 100%, from about 0.01% to about 99.99%, from 0.01% to 99.99%, from about 0.05% to about 99.95%, from about 0.1% to about 99.9%, from 0.1% to about 99.9%, from about 0.5% to about 99.5%, from 0.5% to 99.5%, from about 0% to about 90%, from 0% to 90%, from about 0% to about 80%, from 0% to 80%, from about 0% to about 75%, from 0% to 75%, from about 0% to about 10%, from 0% to 10%, from about 0.01% to about 10%, from 0.01% to 10%, from about 0% to about 25%, from 0% to 25%, from about 0.01% to about 25%, and/or from 0.01% to 25%. In some embodiments, the system and/or apparatus is configured to change the percentage of nicotine in the third vapor in increments of 100%, 50%, 40%, 35%, 30%, 25%, 20%, 15%, 10%, 9%, 8%, 7%, 7.5%, 6%, 5%, 4%, 3%, 2%, 1%, 0.5%, 0.1%, 0.05%, 0.01%, about 100%, about 50%, about 40%, about 35%, about 30%, about 25%, about 20%, about 15%, about 10%, about 9%, about 8%, about 7%, about 7.5%, about 6%, about 5%, about 4%, about 3%, about 2%, about 5%, about 1%, about 0.5%, about 0.1%, about 0.05%, about 0.01%, less than 100%, less than 50%, less than 20%, less than 10%, less than 5%, less than 1%, less than 0.5%, less than 0.1%, less than 0.05%, less than 0.01%, greater than about 100%, greater than about 50%, greater than about 20%, greater than about 10%, greater than about 5%, greater than about 1%, greater than about 0.5%, greater than about 0.1%, greater than about 0.05%, and/or greater than about 0.01%. In some embodiments of the system, the digital processing device comprises on-board memory configured to: store an operating system or computer program configured to perform the instructions; and record a first set of data and a second set of data. In some embodiments, the first set of data comprises vaporization characteristics comprising one or more of: a first power reading of power delivered to the first heater, a second power reading of power delivered to the second heater, a first duration of energization delivered to the first heater, a second duration of energization delivered to the second heater, and a simple pulse signal profile or a pulse width modulation signal profile. In some embodiments of the system, the flow sensor analyzer is configured to detect and record a second set of data comprising one or more of: a date of each user puff; a time of each user puff; a duration of each user puff; an amount of nicotine released to a user;

a puff flow; a puff intensity; and an airflow rate within the vapor release mechanism. In some embodiments of the system, the digital processing device comprises on-board memory and wherein the second set of data is stored in the on-board memory. In some embodiments of the system, the vaporizer housing is configured to receive an attachable mouthpiece. In some embodiments, the mouthpiece is replaceable. In some embodiments, the vaporizer housing is replaceable. In some embodiments of the system, the digital processing device is configured to execute the instructions defined by the computer program based on the nicotine management plan wherein the vapor release mechanism produces the third vapor having a consistent characteristic regardless of the ratio of the first vapor to the second vapor. In some embodiments of the system, the nicotine management plan gradually diminishes the amount or percentage of nicotine in the third vapor over a specified period of time. In some embodiments, the characteristic comprises: measurable amounts of nicotine in the third vapor or measurable percentage of nicotine in the third vapor generated by the electronic vaporizing apparatus; and/or measurable amounts of flavorant in the third vapor or measurable percentage of flavorant in the third vapor generated by the electronic vaporizing apparatus. In some embodiments of the system, the vapor characteristic produced with each puff comprise: vapor intensity (measurable as vapor flow rate), vapor volume, vapor density (measured by spectrophotometry methods known to one of skill in the art), vapor flavor, and/or oral sensation, wherein the characteristic is consistent irrespective of nicotine levels. In some embodiments of the system and/or apparatus, the vapor characteristic produced with each puff comprises vapor intensity (measurable as vapor flow rate). In some embodiments of the system, the vapor characteristic produced with each puff comprises vapor volume. In some embodiments of the system, the vapor characteristic produced with each puff comprises vapor density (measured by spectrophotometry methods known to one of skill in the art). In some embodiments of the system, the vapor characteristic produced with each puff comprises vapor flavor, and/or oral sensation. In some embodiments, the system comprises an override feature, configurable to override the digital processing device to modify the amount or percentage of the nicotine dispensed. In some embodiments, the override feature is manual. In some embodiments, the override feature is automatic. In some embodiments of the system, the microprocessor is configured to control communication systems and input/output program functions for the apparatus. In some embodiments, the electronic communication system for communicating with one or more other electronic device comprises: a wireless communication link; and a wired communication link, wherein the other electronic device comprises: a computer; a mobile device; a computer network; and an electronic storage data device. In some embodiments of the system, the first cartridge chamber and the second chamber are in series arrangement, are in parallel arrangement, and/or comprise a central vapor flow path through a vaporization chamber common to the first cartridge and the second cartridge. In some embodiments of the system, the durable housing comprises at least one of: a power source; a connection interface configured to connect the durable housing to the vaporizer housing; an LED; a battery contact; and a charging interface circuit.

Provided herein is a programmable electronic vaporizing apparatus comprising: first liquid substance in a first cartridge chamber wherein the first liquid substance comprises nicotine, a second liquid substance in a second cartridge chamber and a vapor release mechanism configured to form a third vapor comprising a first vapor formed from the first liquid substance, a second vapor formed from the second liquid substance, or a combination thereof; and a digital processing device, wherein the apparatus changes the third vapor formed by the vapor release mechanism according to instructions provided to the digital processing device from a computer program based on a nicotine management plan. In some embodiments of the apparatus, in order to change the third vapor, the digital processing device is configured to modulate an amount of nicotine in the third vapor according to the nicotine management plan, an amount of nicotine in the first vapor according to the nicotine management plan, an amount of the first liquid substance in the third vapor according to the nicotine management plan, an amount of the first liquid substance in the first vapor according to the nicotine management plan, an amount of the second liquid substance in the third vapor according to the nicotine management plan, an amount of the second liquid substance in the second vapor according to the nicotine management plan, a percentage of the first liquid substance in the third vapor according to the nicotine management plan, a percentage of the second liquid substance in the third vapor according to the nicotine management plan, a percentage of nicotine in the third vapor according to the nicotine management plan, a ratio of the first liquid substance to the second substance in the third vapor according to the nicotine management plan, or a combination thereof. In some embodiments of the apparatus, the first liquid substance comprises a flavorant. In some embodiments, the second liquid substance comprises nicotine. In some embodiments, the second liquid substance comprises no nicotine. In some embodiments, the second liquid substance comprises a flavorant. In some embodiments, the second liquid substance comprises a non-nicotine liquid. In some embodiments, the non-nicotine liquid is a flavorant. In some embodiments, the apparatus comprises a first absorbent material in the first cartridge chamber, the second cartridge chamber, or both. In some embodiments of the apparatus, the vapor release mechanism is configured to independently or simultaneously vaporize variable amounts of the first liquid substance and the second liquid substance. In some embodiments of the apparatus, the vapor release mechanism comprises: a first heater coupled to a first wick, a second heater coupled to a second wick, a first control circuit coupled to the first heater, a second control circuit coupled to the second heater and a first vaporization chamber, wherein the first wick is configured to draw the first liquid substance in proximity to or in contact with the first heater, wherein the second wick is configured to draw the second liquid substance in proximity to or in contact with the second heater, and wherein the first heater and second heater are in fluid communication with the first vaporization chamber, wherein the first control circuit and the second control circuit are part of the digital processing device, and wherein the digital processing device is configured to modulate the amount of the first liquid substance drawn by the first wick to the first heater using the first control circuit and to modulate the amount of the second liquid substance drawn by the second wick to the second heater using the second control circuit. The first heater may comprise a first heater coil configured to heat the first liquid substance in the first wick to vaporize the first liquid substance. The second heater may comprise a second heater coil configured to heat the second liquid substance in the second wick to vaporize the second liquid substance. The first heater may comprise a first foil heater circuit configured to heat the first liquid substance in the first wick (alternatively called a first wicking surface) to vaporize the first liquid substance. The second heater may comprise a second foil heater circuit configured to heat the second liquid substance in the second wick (alternatively called a second wicking surface) to vaporize the second liquid substance. In some embodiments of the apparatus, the vapor release mechanism comprises a first sensor that detects a volume of the first liquid substance in the first cartridge chamber. In some embodiments, the vapor release mechanism comprises a second sensor that detects a volume of the second liquid substance in the second cartridge chamber. In some embodiments, the apparatus comprises a vaporizer housing comprising a first cartridge comprising the first cartridge chamber, a second cartridge comprising the second cartridge chamber, and the vapor release mechanism, or a third cartridge comprising the first cartridge chamber, the second cartridge chamber, and the vapor release mechanism. In some embodiments, the apparatus comprises a durable housing comprising the digital processing device or a portion thereof. In some embodiments of the apparatus, the durable housing is coupled integrally with or removably from the vaporizer housing. In some embodiments of the apparatus, the digital processing device comprises a printed circuit assembly comprising; an electronic interface connection, a flow sensor analyzer, an energy control circuit, and a memory for storing the computer program for providing instruction to the digital processing device. In some embodiments of the apparatus, the printed circuit assembly further comprises a microprocessor, an electronic communication system for communicating with other electronic devices, and an antenna. In some embodiments of the apparatus, the energy control circuit is configured to produce either a simple pulse or a Pulse Width Modulation output signal configured to: individually meter electrical power delivered to the first heater, the second heater, or both; control a first temperature of the first heater and/or a first coil or foil heater circuit thereof, a second temperature the second heater and/or a second coil or foil heater circuit thereof, or a combination thereof; and control a first rate of production of the first vapor, a second rate of production of the second vapor, or a third rate of production of the third vapor. In some embodiments, the apparatus is configured to change the third vapor for any given puff, according to the nicotine management plan. In some embodiments of the apparatus, a vaporization chamber volume of the vaporization chamber corresponds to a typical puff volume. In some embodiments, a typical puff volume is about 15 ml to about 175 ml, about 20 ml to about 150 ml, about 15 ml to about 100 ml, about 15 ml to about 75 ml, about 20 ml to about 75 ml, about 25 ml to about 50 ml, about 25 ml, about 35 ml, about 40 ml, about 45 ml, about 50 ml, about 60 ml, 15 ml to 175 ml, 20 ml to 150 ml, 15 ml to 100 ml, 15 ml to 75 ml, 20 ml to 75 ml, 25 ml to 50 ml, 25 ml, 35 ml, 40 ml, 45 ml, 50 ml, or 60 ml. In some embodiments, the user's own typical puff volume is determined by system, or the user's own typical puff volume is provided to the system and used to adjust the nicotine in the third vapor (as amount or percentage) over time according to the management plan. In some embodiments, the system and/or apparatus is configured to provide an amount of nicotine in the third vapor (i.e. in a given 100 ml volume of the third vapor), wherein the amount of nicotine in 100 ml of third vapor is from about 0.0 mcg to about 200.0 mcg, from 0.0 mcg to 200 mcg, about 0.0 mcg to about 100.0 mcg, from 0.0 mcg to 100 mcg, from about 0.1 mcg to about 199.9 mcg, from 0.1 mcg to 199.9 mcg, from about 0.1 mcg to about 99.9 mcg, from 0.1 mcg to 99.9 mcg, from about 0.5 mcg to about 99.5 mcg, from 0.5 mcg to 99.5 mcg, from about 1.0 mcg to about 99.0 mcg, from 1.0 mcg to 99.0 mcg, from about 5.0 mcg to about 95.0 mcg, from 5.0 mcg to 95.0 mcg, from about 0.5 mcg to about 90.0 mcg, from 0.5 mcg to 90.0 mcg, from about 0.0 mcg to about 90.0 mcg, from 0.0 ml to 90.0 ml, from about 0.0 mcg to about 80.0 mcg, from about 0.5 mcg to about 80.0 mcg, from 0.5 mcg to 80.0 mcg, from 0.0 mcg to 80.0 mcg, from about 0.0 mcg to about 70.0 mcg, from 0.0 mcg to 70.0 mcg, from about 0.0 mcg to about 60.0 mcg, from 0.0 ml to 60.0 ml, from about 1.0 mcg to about 60.0 mcg, from 1.0 ml to 60.0 ml, from about 0.5 mcg to about 60.0 mcg, from 0.5 mcg to 60.0 mcg, from about 0.0 mcg to about 50.0 mcg, from 0.0 mcg to 50.0 mcg, from about 0.5 mcg to about 50.0 mcg, from 0.5 mcg to 50.0 mcg, from about 0.0 mcg to about 20 mcg, or from 0.0 mcg to 20.0 mcg. In some embodiments, the system and/or apparatus is configured to adjust the amount of nicotine in the third vapor (per 100 ml volume of the third vapor) in increments of 0.01 mcg, 0.05 mcg, 0.1 mcg, 0.15 mcg, 0.2 mcg, 0.25 mcg, 0.3 mcg, 0.35 mcg, 0.4 mcg, 0.5 mcg, 0.6 mcg, 0.7 mcg, 0.75 mcg, 0.8 mcg, 0.9 mcg, 1.0 mcg, 2.0 mcg, 3.0 mcg, 4.0 mcg, 5.0 mcg, 6.0 mcg, 7.0 mcg, 8.0 mcg, 9.0 mcg, 10.0 mcg, 11.0 mcg, 12.0 mcg, 13.0 mcg, 14.0 mcg, 15.0 mcg, 16.0 mcg, 17.0 mcg, 18.0 mcg, 19.0 mcg, 20.0 mcg, 25.0 mcg, 30.0 mcg, 40.0 mcg, 50.0 mcg, about 0.01 mcg, about 0.05 mcg, about 0.1 mcg, about 0.15 mcg, about 0.2 mcg, about 0.25 mcg, about 0.3 mcg, about 0.35 mcg, about 0.4 mcg, about 0.5 mcg, about 0.6 mcg, about 0.7 mcg, about 0.75 mcg, about 0.8 mcg, about 0.9 mcg, about 1.0 mcg, about 2.0 mcg, about 3.0 mcg, about 4.0 mcg, about 5.0 mcg, about 6.0 mcg, about 7.0 mcg, about 8.0 mcg, about 9.0 mcg, about 10.0 mcg, about 11.0 mcg, about 12.0 mcg, about 13.0 mcg, about 14.0 mcg, about 15.0 mcg, about 16.0 mcg, about 17.0 mcg, about 18.0 mcg, about 19.0 mcg, about 20.0 mcg, about 25.0 mcg, about 30.0 mcg, about 40.0 mcg, or about 50.0 mcg. In some embodiments, the system and/or apparatus is configured to provide an amount of the nicotine in the third vapor based on a typical puff volume (as defined above) or based on the user's individual puff volume as measured by the apparatus or as provided to the system from about 0.0 mcg to about 250.0 mcg, from 0.0 mcg to 250.0 mcg, about 0.0 mcg to about 100.0 mcg, from 0.0 mcg to 100.0 mcg, from about 0.5 mcg to about 100.0 mcg, from 0.5 mcg to 100.0 mcg, from about 0.5 mcg to about 90.0 mcg, from 0.5 mcg to 90.0 mcg, from about 0.0 mcg to about 75.0 mcg, from 0.0 mcg to 75.0 mcg, 0.01 mcg, 0.05 mcg, 0.1 mcg, 0.15 mcg, 0.2 mcg, 0.25 mcg, 0.3 mcg, 0.35 mcg, 0.4 mcg, 0.5 mcg, 0.6 mcg, 0.7 mcg, 0.75 mcg, 0.8 mcg, 0.9 mcg, 1.0 mcg, 2.0 mcg, 3.0 mcg, 4.0 mcg, 5.0 mcg, 6.0 mcg, 7.0 mcg, 8.0 mcg, 9.0 mcg, 10.0 mcg, 11.0 mcg, 12.0 mcg, 13.0 mcg, 14.0 mcg, 15.0 mcg, 16.0 mcg, 17.0 mcg, 18.0 mcg, 19.0 mcg, 20.0 mcg, 21.0 mcg, 22.0 mcg, 23.0 mcg, 24.0 mcg, 25.0 mcg, 26.0 mcg, 27.0 mcg, 28.0 mcg, 29.0 mcg, 30.0 mcg, 31.0 mcg, 32.0 mcg, 33.0 mcg, 34.0 mcg, 35.0 mcg, 36.0 mcg, 37.0 mcg, 38.0 mcg, 39.0 mcg, 40.0 mcg, 41.0 mcg, 42.0 mcg, 43.0 mcg, 44.0 mcg, 45.0 mcg, 46.0 mcg, 47.0 mcg, 48.0 mcg, 49.0 mcg, 50.0 mcg, 51.0 mcg, 52.0 mcg, 53.0 mcg, 54.0 mcg, 55.0 mcg, 56.0 mcg, 57.0 mcg, 58.0 mcg, 59.0 mcg, 60.0 mcg, 61.0 mcg, 62.0 mcg, 63.0 mcg, 64.0 mcg, 65.0 mcg, 66.0 mcg, 67.0 mcg, 68.0 mcg, 69.0 mcg, 70.0 mcg, 71.0 mcg, 72.0 mcg, 73.0 mcg, 74.0 mcg, 75.0 mcg, 76.0 mcg, 77.0 mcg, 78.0 mcg, 79.0 mcg, 80.0 mcg, 81.0 mcg, 82.0 mcg, 83.0 mcg, 84.0 mcg, 85.0 mcg, 86.0 mcg, 87.0 mcg, 88.0 mcg, 89.0 mcg, 90.0 mcg, 91.0 mcg, 92.0 mcg, 93.0 mcg, 94.0 mcg, 95.0 mcg, 96.0 mcg, 97.0 mcg, 98.0 mcg, 99.0 mcg, 100.0 mcg, 0 mcg to 100 mcg in increments of 0.01 mcg, 0 mcg to 100 mcg in increments of 0.1 mcg, 0 mcg to 100 mcg in increments of 0.5 mcg, 0 mcg to 100 mcg in increments of 1 mcg, 0.5 mcg to 100 mcg in increments of 0.5-5 mcg, 0.0 mcg to 100 mcg in increments of 0.5 mcg to 5 mcg, 0.0 mcg to 150 mcg in increments of 0.5 mcg to 5 mcg, 0.0 mcg to 100 mcg in increments of 0.5 mcg to 25 mcg, about 0.01 mcg, about 0.05 mcg, about 0.1 mcg, about 0.15 mcg, about 0.2 mcg, about 0.25 mcg, about 0.3 mcg, about 0.35 mcg, about 0.4 mcg, about 0.5 mcg, about 0.6 mcg, about 0.7 mcg, about 0.75 mcg, about 0.8 mcg, about 0.9 mcg, about 1.0 mcg, about 2.0 mcg, about 3.0 mcg, about 4.0 mcg, about 5.0 mcg, about 6.0 mcg, about 7.0 mcg, about 8.0 mcg, about 9.0 mcg, about 10.0 mcg, about 11.0 mcg, about 12.0 mcg, about 13.0 mcg, about 14.0 mcg, about 15.0 mcg, about 16.0 mcg, about 17.0 mcg, about 18.0 mcg, about 19.0 mcg, about 20.0 mcg, about 21.0 mcg, about 22.0 mcg, about 23.0 mcg, about 24.0 mcg, about 25.0 mcg, about 26.0 mcg, about 27.0 mcg, about 28.0 mcg, about 29.0 mcg, about 30.0 mcg, about 31.0 mcg, about 32.0 mcg, about 33.0 mcg, about 34.0 mcg, about 35.0 mcg, about 36.0 mcg, about 37.0 mcg, about 38.0 mcg, about 39.0 mcg, about 40.0 mcg, about 41.0 mcg, about 42.0 mcg, about 43.0 mcg, about 44.0 mcg, about 45.0 mcg, about 46.0 mcg, about 47.0 mcg, about 48.0 mcg, about 49.0 mcg, about 50.0 mcg, about 51.0 mcg, about 52.0 mcg, about 53.0 mcg, about 54.0 mcg, about 55.0 mcg, about 56.0 mcg, about 57.0 mcg, about 58.0 mcg, about 59.0 mcg, about 60.0 mcg, about 61.0 mcg, about 62.0 mcg, about 63.0 mcg, about 64.0 mcg, about 65.0 mcg, about 66.0 mcg, about 67.0 mcg, about 68.0 mcg, about 69.0 mcg, about 70.0 mcg, about 71.0 mcg, about 72.0 mcg, about 73.0 mcg, about 74.0 mcg, about 75.0 mcg, about 76.0 mcg, about 77.0 mcg, about 78.0 mcg, about 79.0 mcg, about 80.0 mcg, about 81.0 mcg, about 82.0 mcg, about 83.0 mcg, about 84.0 mcg, about 85.0 mcg, about 86.0 mcg, about 87.0 mcg, about 88.0 mcg, about 89.0 mcg, about 90.0 mcg, about 91.0 mcg, about 92.0 mcg, about 93.0 mcg, about 94.0 mcg, about 95.0 mcg, about 96.0 mcg, about 97.0 mcg, about 98.0 mcg, about 99.0 mcg, about 100.0 mcg, about 0 mcg to about 100 mcg in increments of 0.01 mcg, about 0 mcg to about 100 mcg in increments of 0.1 mcg, about 0 mcg to about 100 mcg in increments of 0.5 mcg, about 0 mcg to about 100 mcg in increments of 1 mcg, about 0.5 mcg to about 100 mcg in increments of 0.5-5 mcg, about 0.0 mcg to about 100 mcg in increments of 0.5 mcg to 5 mcg, about 0.0 mcg to about 150 mcg in increments of 0.5 mcg to 5 mcg, or about 0.0 mcg to about 100 mcg in increments of 0.5 mcg to 25 mcg. In some embodiments, the system and/or apparatus is configured to modulate or adjust the amount of nicotine in the third vapor in increments of 1.0 mcg, 5.0 mcg, 10.0 mcg, 20.0 mcg, 25.0 mcg, 30.0 mcg, 40.0 mcg, 50.0 mcg, 75.0 mcg, 100.0 mcg, 150.0 mcg, 200.0 mcg, 250.0 mcg, about 1.0 mcg, about 5.0 mcg, about 10.0 mcg, about 20.0 mcg, about 25.0 mcg, about 30.0 mcg, about 40.0 mcg, about 50.0 mcg, about 75.0 mcg, about 100.0 mcg, about 150.0 mcg, about 200.0 mcg, about 250.0 mcg, less than 250.0 mcg, less than 200.0 mcg, less than 150.0 mcg, less than 100.0 mcg, less than 75.0 mcg, less than 50.0 mcg, less than 40.0 mcg, less than 30.0 mcg, less than 25.0 mcg, less than 20.0 mcg, less than 10.0 mcg, less than 5.0 mcg, greater than about 5.0 mcg, greater than about 10.0 mcg, greater than about 20.0 mcg, greater than about 25.0 mcg, greater than about 30.0 mcg, greater than about 40.0 mcg, greater than about 50.0 mcg, greater than about 75.0 mcg, greater than about 100.0 mcg, greater than about 150.0 mcg, greater than about 200.0 mcg and greater than about 250.0 mcg. In some embodiments, the system and/or apparatus is configured to modulate the percentage of nicotine in the third vapor from about 0% to about 100%, from 0% to 100%, from about 0.01% to about 99.99%, from 0.01% to 99.99%, from about 0.05% to about 99.95%, from about 0.1% to about 99.9%, from 0.1% to about 99.9%, from about 0.5% to about 99.5%, from 0.5% to 99.5%, from about 0% to about 90%, from 0% to 90%, from about 0% to about 80%, from 0% to 80%, from about 0% to about 75%, from 0% to 75%, from about 0% to about 10%, from 0% to 10%, from about 0.01% to about 10%, from 0.01% to 10%, from about 0% to about 25%, from 0% to 25%, from about 0.01% to about 25%, and/or from 0.01% to 25%. In some embodiments, the system and/or apparatus is configured to change the percentage of nicotine in the third vapor in increments of 100%, 50%, 40%, 35%, 30%, 25%, 20%, 15%, 10%, 9%, 8%, 7%, 7.5%, 6%, 5%, 4%, 3%, 2%, 1%, 0.5%, 0.1%, 0.05%, 0.01%, about 100%, about 50%, about 40%, about 35%, about 30%, about 25%, about 20%, about 15%, about 10%, about 9%, about 8%, about 7%, about 7.5%, about 6%, about 5%, about 4%, about 3%, about 2%, about 5%, about 1%, about 0.5%, about 0.1%, about 0.05%, about 0.01%, less than 100%, less than 50%, less than 20%, less than 10%, less than 5%, less than 1%, less than 0.5%, less than 0.1%, less than 0.05%, less than 0.01%, greater than about 100%, greater than about 50%, greater than about 20%, greater than about 10%, greater than about 5%, greater than about 1%, greater than about 0.5%, greater than about 0.1%, greater than about 0.05%, and/or greater than about 0.01%. In some embodiments of the apparatus, the digital processing device comprises on-board memory configured to store an operating system configured to perform the instructions for operating the vapor release mechanism; and record a first set of data and a second set of data. In some embodiments, the first set of data comprises vaporization characteristics comprising one or more of; a first power reading of power delivered to the first heater, a second power reading of power delivered to the second heater, a first duration of energization delivered to the first heater, a second duration of energization delivered to the second heater, and a simple pulse signal profile or a pulse width modulation signal profile. In some embodiments of the apparatus, the flow sensor analyzer is configured to detect and record a second set of data comprising one or more of: a date of each user puff, a time of each user puff, a duration of each user puff, an amount of nicotine released to a user, a puff flow, a puff intensity, and an airflow rate within the vapor release mechanism. In some embodiments of the apparatus, the digital processing device comprises on-board memory and wherein the second set of data is stored in the on-board memory. In some embodiments of the apparatus, the vaporizer housing is configured to receive an attachable mouthpiece. In some embodiments, the mouthpiece is replaceable. In some embodiments, the vaporizer housing is replaceable. In some embodiments of the apparatus, the digital processing device is configured to execute the instructions defined by the computer program based on the nicotine management plan wherein the vapor release mechanism produces the third vapor having a consistent characteristic regardless of the ratio of the first vapor to the second vapor. In some embodiments, the nicotine management plan gradually diminishes the amount or percentage of nicotine in the third vapor over a specified period of time. In some embodiments of the apparatus, the characteristic comprises measurable amounts of nicotine in the third vapor or measurable percentage of nicotine in the third vapor generated by the electronic vaporizing apparatus. In some embodiments of the apparatus, the vapor characteristic produced with each puff comprise: vapor intensity (measurable as vapor flow rate), vapor volume, vapor density (measured by spectrophotometry methods known to one of skill in the art), vapor flavor, and/or oral sensation, wherein the characteristic is consistent irrespective of nicotine levels. In some embodiments of the apparatus, the vapor characteristic produced with each puff comprises vapor intensity (measurable as vapor flow rate). In some embodiments of the apparatus, the vapor characteristic produced with each puff comprises vapor volume. In some embodiments of the apparatus, the vapor characteristic produced with each puff comprises vapor density (measured by spectrophotometry methods known to one of skill in the art). In some embodiments of the apparatus, the vapor characteristic produced with each puff comprises vapor flavor, and/or oral sensation. In some embodiments, the apparatus comprises an override feature, configurable to override the digital processing device to modify the amount or percentage of the nicotine dispensed. In some embodiments, the override feature is manual. In some embodiments, the override feature is automatic. In some embodiments of the apparatus, the override feature comprises: a button; a sensor; a touch pad; a microphone; an infrared (IR) device; and/or a Bluetooth device. In some embodiments of the apparatus, the microprocessor is configured to control communication systems and input/output program functions for the apparatus. In some embodiments of the apparatus, the electronic communication system for communicating with one or more other electronic device comprises a wireless communication link and/or a wired communication link, wherein the other electronic device comprises: a computer, a mobile device, a computer network and an electronic storage data device. In some embodiments of the apparatus, the first cartridge chamber and the second chamber are in series arrangement; are in parallel arrangement, and/or comprise a central vapor flow path through a vaporization chamber common to the first cartridge and the second cartridge. In some embodiments of the apparatus, the durable housing comprises at least one of: a power source, a connection interface configured to connect the durable housing circuit to the vaporizer housing circuit, an LED, a battery contact, and a charging interface circuit. In some embodiments of the apparatus, the power source comprises: a disposable battery a rechargeable battery, wherein said rechargeable battery is configured with an optional battery charging mechanism, an external charging station, and/or a solar cell. In some embodiments of the apparatus, the durable housing further comprises: a vaporization housing connection interface.

Provided herein is a method of using the system described above, comprising modulating over time and according to a nicotine management plan an amount of nicotine in the third vapor or percentage of nicotine in the third vapor generated by the electronic vaporizing apparatus, wherein a first concentration of nicotine in the first liquid substance is fixed. Provided herein is a method of using the apparatus described above, comprising modulating over time and according to a nicotine management plan an amount of nicotine in the third vapor or percentage of nicotine in the third vapor generated by the electronic vaporizing apparatus, wherein a first concentration of nicotine in the first liquid substance is fixed. In some embodiments of the method with the system or the apparatus, modulating comprises implementing a rate of nicotine reduction in the third vapor over time that is controlled by the computer program and the nicotine management plan in combination with the digital processing device, thereby changing a ratio of first vapor to second vapor in the third vapor over time. In some embodiments, the rate of nicotine reduction with the system comprises: a linear reduction, a logarithmic reduction, a stepped reduction, or a combination thereof, wherein the rate of nicotine reduction is measured in percentage of nicotine per time period. In some embodiments of the method of using the system the nicotine management plan comprises the steps: A1.) establishing a frequency for the number of puffs for a given amount or percentage of nicotine delivered over a first period of time multiplied by a second period of time, B1.) maintaining said frequency for the number of puffs and decrementing the amount or percentage of nicotine delivered by a specified amount for said first period of time multiplied by said second period of time, C1.) repeating step B1.) until the amount or percentage of nicotine delivered=0, and continuing to next step, D1.) maintaining the amount or percentage of 0 nicotine for a third period of time, or until the user stops using the system. In some embodiments of the method using the system, the nicotine management plan comprises the steps: A2.) establishing a frequency for the number of puffs for a given amount or percentage of nicotine delivered over a first period of time multiplied by a second period of time, B2.) changing said frequency for the number of puffs and decrementing the amount or percentage of nicotine delivered by a specified amount for said first period of time multiplied by said second period of time, C2.) repeating step B2.) until the amount or percentage of nicotine delivered=0, and continuing to next step, D2.) maintaining the amount or percentage of 0 nicotine for a third period of time, or until the user stops using the system. In some embodiments of the method with the apparatus, the rate of nicotine reduction comprises: a linear reduction, a logarithmic reduction, stepped reduction, or a combination thereof, wherein the rate of nicotine reduction is measured in percentage of nicotine per time period. In some embodiments of the method with the apparatus, the nicotine management plan comprises the steps: a1.) establishing a frequency for the number of puffs for a given amount or percentage of nicotine delivered over a first period of time multiplied by second period of time, b1.) maintaining said frequency for the number of puffs and decrementing the amount or percentage of nicotine delivered by a specified amount for said first period of time multiplied by said second period of time, c1.) repeating step b1.) until the amount or percentage of nicotine delivered=0, and continuing to next step, d1.) maintaining the amount or percentage of 0 nicotine for a third period of time, or until the user stops using the device. In some embodiments of the method with the apparatus, the nicotine management plan comprises the steps: a2.) establishing a frequency for the number of puffs for a given amount or percentage of nicotine delivered over a first period of time multiplied by second period of time, b2.) changing said frequency for the number of puffs and decrementing the amount or percentage of nicotine delivered by a specified amount for said first period of time multiplied by said second period of time, c2.) repeating step b2.) until the amount or percentage of nicotine delivered=0, and continuing to next step, d2.) maintaining the amount of 0 nicotine for a third period of time, or until the user stops using the device. In some embodiments of the method with the system or the apparatus, the apparatus comprises an override to allow an additional amount or percentage of nicotine to be dispersed. In some embodiments, usage of the override can be monitored and tracked. In some embodiments, the override can be disabled. In some embodiments, the override comprises a time delay. In still other embodiments, the override time delay can be: a fixed period of time; a variable period of time; a series of periods of time; a permanent period of time, or any combination thereof. In some embodiments, the nicotine management plan provides for disablement of the system after a defined period of time following the attainment of an amount or percentage of 0 nicotine delivered. In some embodiments, the nicotine management plan provides for disablement of the apparatus after a defined period of time following the attainment of an amount or percentage of 0 nicotine delivered. Provided herein is a method for smoking cessation comprising: providing any configuration of the system described above and providing a nicotine management plan; wherein the nicotine management plan modulates over time an amount of nicotine in the third vapor or percentage of nicotine in the third vapor generated by the electronic vaporizing apparatus, wherein a first concentration of nicotine in the first liquid substance is fixed. Provided herein is a method for smoking cessation comprising: providing the any configuration of the apparatus described above and providing a nicotine management plan, wherein the nicotine management plan modulates over time an amount of nicotine in the third vapor or percentage of nicotine in the third vapor generated by the electronic vaporizing apparatus, wherein a first concentration of nicotine in the first liquid substance is fixed. In some embodiments of the method using the system or the apparatus, modulating comprises implementing a rate of nicotine reduction in the third vapor over time that is controlled by the computer program and the nicotine management plan in combination with the digital processing device, thereby changing a ratio of first vapor to second vapor in the third vapor over time. In some embodiments of the method using the system, the rate of nicotine reduction comprises: a linear reduction, a logarithmic reduction, a stepped reduction, or a combination thereof, wherein the rate of nicotine reduction is measured in percentage of nicotine per time period. In some embodiments of the method using the system, the nicotine management plan comprises the steps: A1.) establishing a frequency for the number of puffs for a given amount or percentage of nicotine delivered over a first period of time multiplied by a second period of time, B1.) maintaining said frequency for the number of puffs and decrementing the amount or percentage of nicotine delivered by a specified amount for said first period of time multiplied by said second period of time; C1.) repeating step B1.) until the amount or percentage of nicotine delivered=0, and continuing to next step; D1.) maintaining the amount or percentage of 0 nicotine for a third period of time, or until the user stops using the system. In some embodiments of the method using the system, the nicotine management plan comprises the steps: A2.) establishing a frequency for the number of puffs for a given amount or percentage of nicotine delivered over a first period of time multiplied by a second period of time; B2.) changing said frequency for the number of puffs and decrementing the amount or percentage of nicotine delivered by a specified amount for said first period of time multiplied by said second period of time; C2.) repeating step B2.) until the amount or percentage of nicotine delivered=0, and continuing to next step; D2.) maintaining the amount or percentage of 0 nicotine for a third period of time, or until the user stops using the system. In some embodiments of the method using the apparatus, the nicotine management plan comprises the steps: a1.) establishing a frequency for the number of puffs for a given amount or percentage of nicotine delivered over a first period of time multiplied by second period of time; b1.) maintaining said frequency for the number of puffs and decrementing the amount or percentage of nicotine delivered by a specified amount for said first period of time multiplied by said second period of time; c1.) repeating step b1.) until the amount or percentage of nicotine delivered=0, and continuing to next step; d1.) maintaining the amount or percentage of 0 nicotine for a third period of time, or until the user stops using the device. In some embodiments of the method using the apparatus, the nicotine management plan comprises the steps: a2.) establishing a frequency for the number of puffs for a given amount or percentage of nicotine delivered over a first period of time multiplied by second period of time; b2.) changing said frequency for the number of puffs and decrementing the amount or percentage of nicotine delivered by a specified amount for said first period of time multiplied by said second period of time; c2.) repeating step b2.) until the amount or percentage of nicotine delivered=0, and continuing to next step; d2.) maintaining the amount of 0 nicotine for a third period of time, or until the user stops using the device.

Provided herein is an electronic vapor release mechanism for a vaporizing apparatus comprising a digital vaporizing chip configured to independently or simultaneously vaporize variable amounts of a first liquid substance and the second liquid substance. In some embodiments, the digital vaporizing chip comprises: a multi-layer circuit board comprising an outermost layer comprising a connecting interface and an inner layer of thermal and electrical insulating material; a wicking surface located on a portion of the outer-most layer; an airflow channel below the layer of thermal and electrical insulating material comprising a closed first closed end and a second open end comprising an airflow outlet; a plurality of wicking holes located about the wicking surface and in fluid communication with the airflow channel; a foil heater circuit on the wicking surface in fluid communication with the connecting interface; and an airflow inlet located on the outer-most layer and in fluid communication with the airflow channel; wherein the digital vaporizing chip is configured to interface with a digital processing device and power source configured to control the foil heater circuit which in combination with the wicking surface is in intimate contact with a chamber comprising a vaporizable fluid, wherein vaporization of the vaporizable fluid occurs at the interface between the foil heater circuit and the wicking surface when a current is applied to the foil heater circuit according to instructions provided by the digital processing device, and wherein the formed vapor is drawn through the wicking holes into the airflow channel by a vacuum created when air is drawn through the airflow inlet and pulled out through the airflow outlet. In some embodiments, the digital vaporizing chip is configured for a vaporizer cartridge. In some embodiments, the digital vaporizing chip is disposable. In some embodiments, the vaporizer cartridge is disposable. Provided herein is a programmable electronic vaporizing apparatus comprising: a first liquid substance in a first cartridge chamber wherein the first liquid substance comprises nicotine, a second liquid substance in a second cartridge chamber; and a vapor release mechanism comprising a digital vaporizing chip configured to form a third vapor comprising a first vapor formed from the first liquid substance, a second vapor formed from the second liquid substance, or a combination thereof; and a digital processing device, wherein the apparatus changes the third vapor formed by the vapor release mechanism according to instructions provided to the digital processing device from a computer program. In some embodiments of the apparatus, in order to change the third vapor, the digital processing device is configured to modulate an amount of nicotine in the third vapor according to the nicotine management plan, an amount of nicotine in the first vapor according to the nicotine management plan, an amount of the first liquid substance in the third vapor according to the nicotine management plan, an amount of the first liquid substance in the first vapor according to the nicotine management plan, an amount of the second liquid substance in the third vapor according to the nicotine management plan, an amount of the second liquid substance in the second vapor according to the nicotine management plan, a percentage of the first liquid substance in the third vapor according to the nicotine management plan, a percentage of the second liquid substance in the third vapor according to the nicotine management plan, a percentage of nicotine in the third vapor according to the nicotine management plan, a ratio of the first liquid substance to the second substance in the third vapor according to the nicotine management plan, or a combination thereof. In some embodiments, the first liquid substance comprises a flavorant. In some embodiments, the second liquid substance comprises nicotine. In some embodiments the second liquid substance comprises no nicotine. In some embodiments, the second liquid substance comprises a flavorant. In some embodiments, the second liquid substance comprises a non-nicotine liquid. In some embodiments, the non-nicotine liquid is a flavorant. In some embodiments, the apparatus comprises a first absorbent material in the first cartridge chamber, the second cartridge chamber, or both. In some embodiments of the apparatus, the vapor release mechanism is configured to independently or simultaneously vaporize variable amounts of the first liquid substance and the second liquid substance. In some embodiments of the apparatus, the digital vaporizing chip comprises a multi-layer circuit board comprising: a first outermost layer comprising a first connecting interface, a second outermost layer comprising a second connecting interface, a first inner layer comprising thermal and electrical insulating material, and a second inner layer comprising thermal and electrical insulating material; a first wicking surface located on a portion of the first outer-most layer, a second wicking surface located on a portion of the second outer-most layer; an airflow channel between the first inner layer and second inner layer comprising a closed first end and an open second end comprising an airflow outlet; a first plurality of wicking holes located about the first wicking surface in fluid communication with the airflow channel, a second plurality of wicking holes located about the second wicking surface in fluid communication with the airflow channel; a first foil heater circuit on the first wicking surface in fluid communication with the first connecting interface, a second foil heater circuit on the second wicking surface in fluid communication with the second connecting interface; a first airflow inlet located on the first outer-most layer in fluid communication with the airflow channel and a second airflow inlet located on the second outer-most layer in fluid communication with the airflow channel, wherein the first wicking surface is configured to draw the first liquid substance in proximity to or in contact with the first foil heater circuit, wherein the second wicking surface is configured to draw the second liquid substance in proximity to or in contact with the second foil heater circuit, and wherein the first foil heater circuit and second foil heater circuit are in fluid communication with the airflow channel, wherein the first connecting interface and the second connecting interface are part of the digital processing device, and wherein the digital processing device is configured to modulate the amount of the first liquid substance drawn by the first foil heater circuit using the first connecting interface and to modulate the amount of the second liquid substance drawn by the second foil heater circuit using the second connecting interface. In some embodiments of the apparatus, the vapor release mechanism comprises a first sensor that detects a volume of the first liquid substance in the first cartridge chamber. In some embodiments, the vapor release mechanism comprises a second sensor that detects a volume of the second liquid substance in the second cartridge chamber. In some embodiments, the apparatus comprises a vaporizer housing comprising a first cartridge comprising the first cartridge chamber, a second cartridge comprising the second cartridge chamber, and the vapor release mechanism, or a third cartridge comprising the first cartridge chamber, the second cartridge chamber, and the vapor release mechanism. In some embodiments, the apparatus comprises a durable housing comprising the digital processing device or a portion thereof. In some embodiments, the durable housing is coupled integrally with or removably from the vaporizer housing. In some embodiments of the apparatus, the digital processing device comprises a printed circuit assembly comprising: an electronic interface connection, a flow sensor analyzer, an energy control circuit, and a memory for storing the computer program. In some embodiments of the apparatus, the printed circuit assembly further comprises: a microprocessor, an electronic communication system for communicating with other electronic devices, and an antenna. In some embodiments of the apparatus, the energy control circuit is configured to produce either a simple pulse or a Pulse Width Modulation output signal configured to individually meter electrical power delivered to the first heater, the second heater, or both; control a first temperature of the first heater, a second temperature the second heater, or both; and control a first rate of production of the first vapor, a second rate of production of the second vapor, or a third rate of production of the third vapor. The first heater may comprise a first heater coil configured to heat the first liquid substance in the first wick to vaporize the first liquid substance. The second heater may comprise a second heater coil configured to heat the second liquid substance in the second wick to vaporize the second liquid substance. The first heater may comprise a first foil heater circuit configured to heat the first liquid substance in the first wick (alternatively called a first wicking surface) to vaporize the first liquid substance. The second heater may comprise a second foil heater circuit configured to heat the second liquid substance in the second wick (alternatively called a second wicking surface) to vaporize the second liquid substance. In some embodiments, the apparatus is configured to change the third vapor for any given puff, according to the nicotine management plan. In some embodiments of the apparatus, a vaporization chamber volume of the vaporization chamber corresponds to a typical puff volume. In some embodiments, a typical puff volume is about 15 ml to about 175 ml, about 20 ml to about 150 ml, about 15 ml to about 100 ml, about 15 ml to about 75 ml, about 20 ml to about 75 ml, about 25 ml to about 50 ml, about 25 ml, about 35 ml, about 40 ml, about 45 ml, about 50 ml, about 60 ml, 15 ml to 175 ml, 20 ml to 150 ml, 15 ml to 100 ml, 15 ml to 75 ml, 20 ml to 75 ml, 25 ml to 50 ml, 25 ml, 35 ml, 40 ml, 45 ml, 50 ml, or 60 ml. In some embodiments, the user's own typical puff volume is determined by system, or the user's own typical puff volume is provided to the system and used to adjust the nicotine in the third vapor (as amount or percentage) over time according to the management plan. In some embodiments, the system and/or apparatus is configured to provide an amount of nicotine in the third vapor (i.e. in a given 100 ml volume of the third vapor), wherein the amount of nicotine in 100 ml of third vapor is from about 0.0 mcg to about 200.0 mcg, from 0.0 mcg to 200 mcg, about 0.0 mcg to about 100.0 mcg, from 0.0 mcg to 100 mcg, from about 0.1 mcg to about 199.9 mcg, from 0.1 mcg to 199.9 mcg, from about 0.1 mcg to about 99.9 mcg, from 0.1 mcg to 99.9 mcg, from about 0.5 mcg to about 99.5 mcg, from 0.5 mcg to 99.5 mcg, from about 1.0 mcg to about 99.0 mcg, from 1.0 mcg to 99.0 mcg, from about 5.0 mcg to about 95.0 mcg, from 5.0 mcg to 95.0 mcg, from about 0.5 mcg to about 90.0 mcg, from 0.5 mcg to 90.0 mcg, from about 0.0 mcg to about 90.0 mcg, from 0.0 ml to 90.0 ml, from about 0.0 mcg to about 80.0 mcg, from about 0.5 mcg to about 80.0 mcg, from 0.5 mcg to 80.0 mcg, from 0.0 mcg to 80.0 mcg, from about 0.0 mcg to about 70.0 mcg, from 0.0 mcg to 70.0 mcg, from about 0.0 mcg to about 60.0 mcg, from 0.0 ml to 60.0 ml, from about 1.0 mcg to about 60.0 mcg, from 1.0 ml to 60.0 ml, from about 0.5 mcg to about 60.0 mcg, from 0.5 mcg to 60.0 mcg, from about 0.0 mcg to about 50.0 mcg, from 0.0 mcg to 50.0 mcg, from about 0.5 mcg to about 50.0 mcg, from 0.5 mcg to 50.0 mcg, from about 0.0 mcg to about 20 mcg, or from 0.0 mcg to 20.0 mcg. In some embodiments, the system and/or apparatus is configured to adjust the amount of nicotine in the third vapor (per 100 ml volume of the third vapor) in increments of 0.01 mcg, 0.05 mcg, 0.1 mcg, 0.15 mcg, 0.2 mcg, 0.25 mcg, 0.3 mcg, 0.35 mcg, 0.4 mcg, 0.5 mcg, 0.6 mcg, 0.7 mcg, 0.75 mcg, 0.8 mcg, 0.9 mcg, 1.0 mcg, 2.0 mcg, 3.0 mcg, 4.0 mcg, 5.0 mcg, 6.0 mcg, 7.0 mcg, 8.0 mcg, 9.0 mcg, 10.0 mcg, 11.0 mcg, 12.0 mcg, 13.0 mcg, 14.0 mcg, 15.0 mcg, 16.0 mcg, 17.0 mcg, 18.0 mcg, 19.0 mcg, 20.0 mcg, 25.0 mcg, 30.0 mcg, 40.0 mcg, 50.0 mcg, about 0.01 mcg, about 0.05 mcg, about 0.1 mcg, about 0.15 mcg, about 0.2 mcg, about 0.25 mcg, about 0.3 mcg, about 0.35 mcg, about 0.4 mcg, about 0.5 mcg, about 0.6 mcg, about 0.7 mcg, about 0.75 mcg, about 0.8 mcg, about 0.9 mcg, about 1.0 mcg, about 2.0 mcg, about 3.0 mcg, about 4.0 mcg, about 5.0 mcg, about 6.0 mcg, about 7.0 mcg, about 8.0 mcg, about 9.0 mcg, about 10.0 mcg, about 11.0 mcg, about 12.0 mcg, about 13.0 mcg, about 14.0 mcg, about 15.0 mcg, about 16.0 mcg, about 17.0 mcg, about 18.0 mcg, about 19.0 mcg, about 20.0 mcg, about 25.0 mcg, about 30.0 mcg, about 40.0 mcg, or about 50.0 mcg. In some embodiments, the system and/or apparatus is configured to provide an amount of the nicotine in the third vapor based on a typical puff volume (as defined above) or based on the user's individual puff volume as measured by the apparatus or as provided to the system from about 0.0 mcg to about 250.0 mcg, from 0.0 mcg to 250.0 mcg, about 0.0 mcg to about 100.0 mcg, from 0.0 mcg to 100.0 mcg, from about 0.5 mcg to about 100.0 mcg, from 0.5 mcg to 100.0 mcg, from about 0.5 mcg to about 90.0 mcg, from 0.5 mcg to 90.0 mcg, from about 0.0 mcg to about 75.0 mcg, from 0.0 mcg to 75.0 mcg, 0.01 mcg, 0.05 mcg, 0.1 mcg, 0.15 mcg, 0.2 mcg, 0.25 mcg, 0.3 mcg, 0.35 mcg, 0.4 mcg, 0.5 mcg, 0.6 mcg, 0.7 mcg, 0.75 mcg, 0.8 mcg, 0.9 mcg, 1.0 mcg, 2.0 mcg, 3.0 mcg, 4.0 mcg, 5.0 mcg, 6.0 mcg, 7.0 mcg, 8.0 mcg, 9.0 mcg, 10.0 mcg, 11.0 mcg, 12.0 mcg, 13.0 mcg, 14.0 mcg, 15.0 mcg, 16.0 mcg, 17.0 mcg, 18.0 mcg, 19.0 mcg, 20.0 mcg, 21.0 mcg, 22.0 mcg, 23.0 mcg, 24.0 mcg, 25.0 mcg, 26.0 mcg, 27.0 mcg, 28.0 mcg, 29.0 mcg, 30.0 mcg, 31.0 mcg, 32.0 mcg, 33.0 mcg, 34.0 mcg, 35.0 mcg, 36.0 mcg, 37.0 mcg, 38.0 mcg, 39.0 mcg, 40.0 mcg, 41.0 mcg, 42.0 mcg, 43.0 mcg, 44.0 mcg, 45.0 mcg, 46.0 mcg, 47.0 mcg, 48.0 mcg, 49.0 mcg, 50.0 mcg, 51.0 mcg, 52.0 mcg, 53.0 mcg, 54.0 mcg, 55.0 mcg, 56.0 mcg, 57.0 mcg, 58.0 mcg, 59.0 mcg, 60.0 mcg, 61.0 mcg, 62.0 mcg, 63.0 mcg, 64.0 mcg, 65.0 mcg, 66.0 mcg, 67.0 mcg, 68.0 mcg, 69.0 mcg, 70.0 mcg, 71.0 mcg, 72.0 mcg, 73.0 mcg, 74.0 mcg, 75.0 mcg, 76.0 mcg, 77.0 mcg, 78.0 mcg, 79.0 mcg, 80.0 mcg, 81.0 mcg, 82.0 mcg, 83.0 mcg, 84.0 mcg, 85.0 mcg, 86.0 mcg, 87.0 mcg, 88.0 mcg, 89.0 mcg, 90.0 mcg, 91.0 mcg, 92.0 mcg, 93.0 mcg, 94.0 mcg, 95.0 mcg, 96.0 mcg, 97.0 mcg, 98.0 mcg, 99.0 mcg, 100.0 mcg, 0 mcg to 100 mcg in increments of 0.01 mcg, 0 mcg to 100 mcg in increments of 0.1 mcg, 0 mcg to 100 mcg in increments of 0.5 mcg, 0 mcg to 100 mcg in increments of 1 mcg, 0.5 mcg to 100 mcg in increments of 0.5-5 mcg, 0 mcg to 100 mcg in increments of 0.5 mcg to 5 mcg, 0.0 mcg to 150 mcg in increments of 0.5 mcg to 5 mcg, 0.0 mcg to 100 mcg in increments of 0.5 mcg to 25 mcg, about 0.01 mcg, about 0.05 mcg, about 0.1 mcg, about 0.15 mcg, about 0.2 mcg, about 0.25 mcg, about 0.3 mcg, about 0.35 mcg, about 0.4 mcg, about 0.5 mcg, about 0.6 mcg, about 0.7 mcg, about 0.75 mcg, about 0.8 mcg, about 0.9 mcg, about 1.0 mcg, about 2.0 mcg, about 3.0 mcg, about 4.0 mcg, about 5.0 mcg, about 6.0 mcg, about 7.0 mcg, about 8.0 mcg, about 9.0 mcg, about 10.0 mcg, about 11.0 mcg, about 12.0 mcg, about 13.0 mcg, about 14.0 mcg, about 15.0 mcg, about 16.0 mcg, about 17.0 mcg, about 18.0 mcg, about 19.0 mcg, about 20.0 mcg, about 21.0 mcg, about 22.0 mcg, about 23.0 mcg, about 24.0 mcg, about 25.0 mcg, about 26.0 mcg, about 27.0 mcg, about 28.0 mcg, about 29.0 mcg, about 30.0 mcg, about 31.0 mcg, about 32.0 mcg, about 33.0 mcg, about 34.0 mcg, about 35.0 mcg, about 36.0 mcg, about 37.0 mcg, about 38.0 mcg, about 39.0 mcg, about 40.0 mcg, about 41.0 mcg, about 42.0 mcg, about 43.0 mcg, about 44.0 mcg, about 45.0 mcg, about 46.0 mcg, about 47.0 mcg, about 48.0 mcg, about 49.0 mcg, about 50.0 mcg, about 51.0 mcg, about 52.0 mcg, about 53.0 mcg, about 54.0 mcg, about 55.0 mcg, about 56.0 mcg, about 57.0 mcg, about 58.0 mcg, about 59.0 mcg, about 60.0 mcg, about 61.0 mcg, about 62.0 mcg, about 63.0 mcg, about 64.0 mcg, about 65.0 mcg, about 66.0 mcg, about 67.0 mcg, about 68.0 mcg, about 69.0 mcg, about 70.0 mcg, about 71.0 mcg, about 72.0 mcg, about 73.0 mcg, about 74.0 mcg, about 75.0 mcg, about 76.0 mcg, about 77.0 mcg, about 78.0 mcg, about 79.0 mcg, about 80.0 mcg, about 81.0 mcg, about 82.0 mcg, about 83.0 mcg, about 84.0 mcg, about 85.0 mcg, about 86.0 mcg, about 87.0 mcg, about 88.0 mcg, about 89.0 mcg, about 90.0 mcg, about 91.0 mcg, about 92.0 mcg, about 93.0 mcg, about 94.0 mcg, about 95.0 mcg, about 96.0 mcg, about 97.0 mcg, about 98.0 mcg, about 99.0 mcg, about 100.0 mcg, about 0 mcg to about 100 mcg in increments of 0.01 mcg, about 0 mcg to about 100 mcg in increments of 0.1 mcg, about 0 mcg to about 100 mcg in increments of 0.5 mcg, about 0 mcg to about 100 mcg in increments of 1 mcg, about 0.5 mcg to about 100 mcg in increments of 0.5-5 mcg, about 0.0 mcg to about 100 mcg in increments of 0.5 mcg to 5 mcg, about 0.0 mcg to about 150 mcg in increments of 0.5 mcg to 5 mcg, or about 0.0 mcg to about 100 mcg in increments of 0.5 mcg to 25 mcg. In some embodiments, the system and/or apparatus is configured to modulate or adjust the amount of nicotine in the third vapor in increments of 1.0 mcg, 5.0 mcg, 10.0 mcg, 20.0 mcg, 25.0 mcg, 30.0 mcg, 40.0 mcg, 50.0 mcg, 75.0 mcg, 100.0 mcg, 150.0 mcg, 200.0 mcg, 250.0 mcg, about 1.0 mcg, about 5.0 mcg, about 10.0 mcg, about 20.0 mcg, about 25.0 mcg, about 30.0 mcg, about 40.0 mcg, about 50.0 mcg, about 75.0 mcg, about 100.0 mcg, about 150.0 mcg, about 200.0 mcg, about 250.0 mcg, less than 250.0 mcg, less than 200.0 mcg, less than 150.0 mcg, less than 100.0 mcg, less than 75.0 mcg, less than 50.0 mcg, less than 40.0 mcg, less than 30.0 mcg, less than 25.0 mcg, less than 20.0 mcg, less than 10.0 mcg, less than 5.0 mcg, greater than about 5.0 mcg, greater than about 10.0 mcg, greater than about 20.0 mcg, greater than about 25.0 mcg, greater than about 30.0 mcg, greater than about 40.0 mcg, greater than about 50.0 mcg, greater than about 75.0 mcg, greater than about 100.0 mcg, greater than about 150.0 mcg, greater than about 200.0 mcg and greater than about 250.0 mcg. In some embodiments, the system and/or apparatus is configured to modulate the percentage of nicotine in the third vapor from about 0% to about 100%, from 0% to 100%, from about 0.01% to about 99.99%, from 0.01% to 99.99%, from about 0.05% to about 99.95%, from about 0.1% to about 99.9%, from 0.1% to about 99.9%, from about 0.5% to about 99.5%, from 0.5% to 99.5%, from about 0% to about 90%, from 0% to 90%, from about 0% to about 80%, from 0% to 80%, from about 0% to about 75%, from 0% to 75%, from about 0% to about 10%, from 0% to 10%, from about 0.01% to about 10%, from 0.01% to 10%, from about 0% to about 25%, from 0% to 25%, from about 0.01% to about 25%, and/or from 0.01% to 25%. In some embodiments, the system and/or apparatus is configured to change the percentage of nicotine in the third vapor in increments of 100%, 50%, 40%, 35%, 30%, 25%, 20%, 15%, 10%, 9%, 8%, 7%, 7.5%, 6%, 5%, 4%, 3%, 2%, 1%, 0.5%, 0.1%, 0.05%, 0.01%, about 100%, about 50%, about 40%, about 35%, about 30%, about 25%, about 20%, about 15%, about 10%, about 9%, about 8%, about 7%, about 7.5%, about 6%, about 5%, about 4%, about 3%, about 2%, about 5%, about 1%, about 0.5%, about 0.1%, about 0.05%, about 0.01%, less than 100%, less than 50%, less than 20%, less than 10%, less than 5%, less than 1%, less than 0.5%, less than 0.1%, less than 0.05%, less than 0.01%, greater than about 100%, greater than about 50%, greater than about 20%, greater than about 10%, greater than about 5%, greater than about 1%, greater than about 0.5%, greater than about 0.1%, greater than about 0.05%, and greater than about 0.01%. In some embodiments of the apparatus, the digital processing device comprises on-board memory configured to: store an operating system configured to perform the instructions; and record a first set of data and a second set of data. In some embodiments of the apparatus, the first set of data comprises vaporization characteristics comprising one or more of: a first power reading of power delivered to the first heater, a second power reading of power delivered to the second heater, a first duration of energization delivered to the first heater, a second duration of energization delivered to the second heater, and a simple pulse signal profile or a pulse width modulation signal profile. In some embodiments of the apparatus, the flow sensor analyzer is configured to detect and record a second set of data comprising one or more of: a date of each user puff, a time of each user puff, a duration of each user puff, an amount of nicotine released to a user, a puff flow, a puff intensity, and an airflow rate within the vapor release mechanism. In some embodiments of the apparatus, the digital processing device comprises on-board memory and wherein the second set of data is stored in the on-board memory. In some embodiments of the apparatus, the vaporizer housing is configured to receive an attachable mouthpiece. In some embodiments, the mouthpiece is replaceable. In some embodiments, the vaporizer housing is replaceable. In some embodiments of the apparatus, the digital processing device is configured to execute the instructions defined by the computer program based on the nicotine management plan wherein the vapor release mechanism produces the third vapor having a consistent characteristic regardless of the ratio of the first vapor to the second vapor. In some embodiments of the apparatus, the nicotine management plan gradually diminishes the amount or percentage of nicotine in the third vapor over a specified period of time. In some embodiments of the apparatus, the characteristic comprises measurable amounts of nicotine in the third vapor or measurable percentage of nicotine in the third vapor generated by the electronic vaporizing apparatus. In some embodiments, the apparatus an override feature, configurable to override the digital processing device to modify the amount or percentage of the nicotine dispensed. In some embodiments, the override feature is manual. In some embodiments, the override feature is automatic. In some embodiments of the apparatus, the override feature comprises: a button, a sensor, a touch pad, a microphone, an infrared (IR) device, and/or a Bluetooth device. In some embodiments of the apparatus, the microprocessor is configured to control communication systems and input/output program functions for the apparatus. In some embodiments of the apparatus, the electronic communication system for communicating with one or more other electronic device comprises: a wireless communication link; and a wired communication link, wherein the other electronic device comprises: a computer, a mobile device, a computer network, and an electronic storage data device. In some embodiments of the apparatus, the first cartridge chamber and the second chamber are in series arrangement, are in parallel arrangement, and/or comprise a central vapor flow path through a vaporization chamber common to the first cartridge and the second cartridge. In some embodiments of the apparatus, the durable housing comprises at least one of: a power source, a connection interface configured to connect the durable housing to the vaporizer housing, an LED, a battery contact, and a charging interface circuit. In some embodiments of the apparatus, the power source comprises: a disposable battery, a rechargeable battery, wherein said rechargeable battery is configured with an optional battery charging mechanism, an external charging station, and/or a solar cell. In some embodiments of the apparatus, the durable housing further comprises: a vaporization housing connection interface; and a removable end cap.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6B-1 is an illustrative ISO detail end view of the digital vaporizing chip with a foil heater circuit and interconnect feature of FIG. 6A.

FIG. 6B-2 is an illustrative ISO view of an embodiment digital vaporizing chip with a foil heater circuit of an embodiment apparatus and/or system.

FIG. 6C-1 is an illustrative reverse angle ISO view of an embodiment digital vaporizing chip with a foil heater circuit of FIG. 6B-2.

FIG. 6C-2 is an illustrative ISO view of the opposite side of the digital vaporizing chip with a foil heater circuit of FIG. 6C-1.

FIG. 6D-1 is an illustrative end ISO detail view of the digital vaporizing chip of FIG. 6B-2 with a foil heater circuit showing the airflow channel between the layers of the digital vaporizing chip.

FIG. 6D-2 is a second illustrative end ISO detail view of the a digital vaporizing chip of FIG. 6B-2 with a foil heater circuit showing the airflow channel between the layers of the a digital vaporizing chip and the various wick holes in contact with their respective foil heater circuit.

FIG. 6D-3 is an illustrative ISO cross-section detail view of the digital vaporizing chip of FIG. 6B-2 with a foil heater circuit through the airflow channel.

DETAILED DESCRIPTION OF THE INVENTION

Figure 1A:
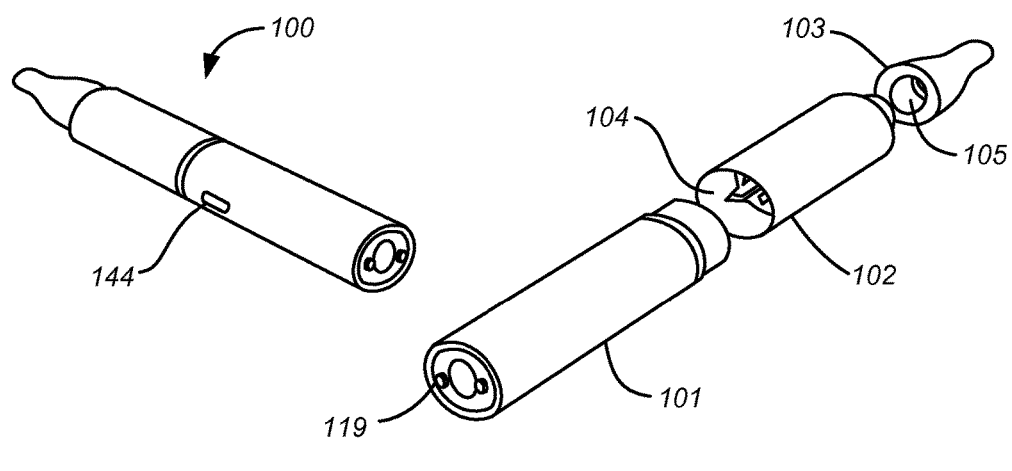
FIG. 1A is an illustrative isometric view of an exemplary electronic vaporizing apparatus assembly and exploded sub-assembly thereof.

Provided herein are systems, methods, and devices (apparatuses) for the reduction of nicotine consumption based on a nicotine management plan to reduce or eliminate nicotine dependence. The systems, apparatuses and methods described herein utilize a digital processing device in combination with a vapor release mechanism to vaporize and blend nicotine and non-nicotine liquid substances from cartridge chambers to produce vapors configured to reduce nicotine consumption and dependence at a modulated rate over a specified period of time based on the nicotine management plan. The system and apparatus are configurable to track and report data acquired during use and provide feedback to a user and/or a clinical professional. The combination of the apparatus configuration and the management plan allows for fine control of the nicotine delivered to a user over time.

The nicotine management plan utilizes a electronic vaporizing apparatus system comprising an electronic controller, software and a multi-chamber cartridge or multiple cartridges to multiple vapors (nicotine based and nicotine-free; either of which could include flavorants or without flavorants), so that as a nicotine amount or percentage is decreased over time, the user senses no changes in a vapor characteristic or flavor (or both), while simultaneously reducing physical dependence on nicotine.

Further, the nicotine management plan uses a software application or applications in the apparatus or in a device (computer or smart device, for example) to establish or record or allow for input of a user's baseline nicotine behavior and usage. The software application or applications automatically or allow a user or caregiver to develop the nicotine management plan or choose a pre-set nicotine management plan. The user then uses the electronic cigarette apparatus according to the nicotine management plan. The apparatus controls the experience for the user according to the nicotine management plan, which limits the amount or rate or percent of nicotine the user can intake for a given time, for example. The apparatus is configured to allow fine control of the nicotine deliverable or delivered to a user, thus the nicotine management plan may subtly reduce the amount of nicotine delivered to the user with little noticeable change in user experience from one day to the next, or one use to the next. The software application or applications is configured to track, record and report progress back to the user and/or a clinician (i.e. caregiver) to assist in the reinforcement of the nicotine management plan and achievement of a goal of reduction or cessation of nicotine dependence. While the ultimate goal may be cessation of nicotine dependence, another alternative goal may simply be reduction of nicotine usage. Thus, as used herein the systems are described as "cessation system" or "cessation systems", however, they could alternatively be called a "reduction system" or "reduction systems" in any embodiment described herein.

While nicotine is used throughout this specification, the systems, apparatuses, methods, and management plans described herein may be used with other drugs as described with regard to nicotine herein, with or without adjustment to the apparatus, systems, methods, or managements as one of skill in the art would know to do without undue experimentation upon reading the disclosure herein.

The embodiments of the disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar parts throughout the several views of the drawings.

Unless otherwise defined, all technical terms used herein have the same meaning as commonly understood by one of ordinary skill in the art to which the inventions herein belongs. As used in this specification and the appended claims, the singular forms "a," "an," and "the" include plural references unless the context clearly dictates otherwise. Any reference to "or" herein is intended to encompass "and/or" unless otherwise stated.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

Provided herein is a programmable smoking cessation system comprising an electronic vaporizing apparatus comprising: a first liquid substance in a first cartridge chamber wherein the first liquid substance comprises nicotine; a second liquid substance in a second cartridge chamber; a vapor release mechanism configured to form a third vapor comprising a first vapor formed from the first liquid substance, a second vapor formed from the second liquid substance, or a combination thereof; and a digital processing device, and a nicotine management plan, wherein the system changes the third vapor formed by the vapor release mechanism according to instructions provided to the digital processing device from a computer program based on the nicotine management plan. Provided herein is a programmable electronic vaporizing apparatus comprising: first liquid substance in a first cartridge chamber wherein the first liquid substance comprises nicotine, a second liquid substance in a second cartridge chamber and a vapor release mechanism configured to form a third vapor comprising a first vapor formed from the first liquid substance, a second vapor formed from the second liquid substance, or a combination thereof; and a digital processing device, wherein the apparatus changes the third vapor formed by the vapor release mechanism according to instructions provided to the digital processing device from a computer program based on a nicotine management plan.

In some embodiments in which the programmable electronic vaporizing apparatus and/or nicotine cessation system described herein includes a digital processing device, the digital processing device includes one or more hardware central processing units (CPU) that carry out the device's functions. In some embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft Xbox 360®, Microsoft Xbox One, Nintendo® Wii®, Nintendo® Wii U®, and Ouya®.

In some embodiments, the apparatus includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

In some embodiments, electronic vaporizing apparatuses and programmable smoking cessation system disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the electronic vaporizing apparatuses and programmable smoking cessation system disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™ PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

In some embodiments, the programmable smoking cessation system and/or electronic vaporizing apparatus includes software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the electronic vaporizing apparatuses (apparatuses) and/or programmable smoking cessation system disclosed herein include one or more databases, or use of the same. In view of the disclosure provided herein, those of skill in the art will recognize that many databases are suitable for storage and retrieval of user compliance and device (or apparatus) performance information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

As used herein, "digital processing device" (DPD) refers to "a programmable electronic controller'. In some embodiments, a programmable electronic controller comprises a flex circuit wherein assembled electronic circuits comprise electronic devices mounted on flexible plastic substrates. Additionally the DPD may be a digital processing device comprising a printed circuit assembly (PCA).

As used herein, "computer program" and "software" are synonymous and meaning configured to provide instructions for components of the system and/or apparatus. Additionally the computer program may comprise software modules or packets of instructions for components of the system or apparatus.

In some embodiments of the system and/or apparatus, in order to change the third vapor, the digital processing device is configured to modulate an amount of nicotine in the third vapor according to the nicotine management plan, an amount of nicotine in the first vapor according to the nicotine management plan, an amount of the first liquid substance in the third vapor according to the nicotine management plan, an amount of the first liquid substance in the first vapor according to the nicotine management plan, an amount of the second liquid substance in the third vapor according to the nicotine management plan, an amount of the second liquid substance in the second vapor according to the nicotine management plan, a percentage of the first liquid substance in the third vapor according to the nicotine management plan, a percentage of the second liquid substance in the third vapor according to the nicotine management plan, a percentage of nicotine in the third vapor according to the nicotine management plan, a ratio of the first liquid substance to the second substance in the third vapor according to the nicotine management plan, or a combination thereof. In some embodiments of the apparatus, in order to change the third vapor, the digital processing device is configured to modulate an amount of nicotine in the third vapor according to the nicotine management plan, an amount of nicotine in the first vapor according to the nicotine management plan, an amount of the first liquid substance in the third vapor according to the nicotine management plan, an amount of the first liquid substance in the first vapor according to the nicotine management plan, an amount of the second liquid substance in the third vapor according to the nicotine management plan, an amount of the second liquid substance in the second vapor according to the nicotine management plan, a percentage of the first liquid substance in the third vapor according to the nicotine management plan, a percentage of the second liquid substance in the third vapor according to the nicotine management plan, a percentage of nicotine in the third vapor according to the nicotine management plan, a ratio of the first liquid substance to the second substance in the third vapor according to the nicotine management plan, or a combination thereof. In some embodiments of the system and/or apparatus, in order to change the third vapor, the digital processing device is configured to modulate an amount of nicotine in the third vapor according to the nicotine management plan.

In some embodiments of the system and/or apparatus, in order to change the third vapor, the digital processing device is configured to modulate an amount of nicotine in the first vapor according to the nicotine management plan. The amount of nicotine in the first vapor may be based on a standard volume of third vapor, such as per 100 ml of the third vapor, or based on a typical puff volume, or based on the user's own typical puff volume, for non-limiting example. In some embodiments, the system and/or apparatus is configured to provide an amount of nicotine in the third vapor (i.e. in a given 100 ml volume of the third vapor), wherein the amount of nicotine in 100 ml of third vapor is from about 0.0 mcg to about 200.0 mcg, from 0.0 mcg to 200 mcg, about 0.0 mcg to about 100.0 mcg, from 0.0 mcg to 100 mcg, from about 0.1 mcg to about 199.9 mcg, from 0.1 mcg to 199.9 mcg, from about 0.1 mcg to about 99.9 mcg, from 0.1 mcg to 99.9 mcg, from about 0.5 mcg to about 99.5 mcg, from 0.5 mcg to 99.5 mcg, from about 1.0 mcg to about 99.0 mcg, from 1.0 mcg to 99.0 mcg, from about 5.0 mcg to about 95.0 mcg, from 5.0 mcg to 95.0 mcg, from about 0.5 mcg to about 90.0 mcg, from 0.5 mcg to 90.0 mcg, from about 0.0 mcg to about 90.0 mcg, from 0.0 ml to 90.0 ml, from about 0.0 mcg to about 80.0 mcg, from about 0.5 mcg to about 80.0 mcg, from 0.5 mcg to 80.0 mcg, from 0.0 mcg to 80.0 mcg, from about 0.0 mcg to about 70.0 mcg, from 0.0 mcg to 70.0 mcg, from about 0.0 mcg to about 60.0 mcg, from 0.0 ml to 60.0 ml, from about 1.0 mcg to about 60.0 mcg, from 1.0 ml to 60.0 ml, from about 0.5 mcg to about 60.0 mcg, from 0.5 mcg to 60.0 mcg, from about 0.0 mcg to about 50.0 mcg, from 0.0 mcg to 50.0 mcg, from about 0.5 mcg to about 50.0 mcg, from 0.5 mcg to 50.0 mcg, from about 0.0 mcg to about 20 mcg, or from 0.0 mcg to 20.0 mcg. In some embodiments, the system and/or apparatus is configured to adjust the amount of nicotine in the third vapor (per 100 ml volume of the third vapor) in increments of 0.01 mcg, 0.05 mcg, 0.1 mcg, 0.15 mcg, 0.2 mcg, 0.25 mcg, 0.3 mcg, 0.35 mcg, 0.4 mcg, 0.5 mcg, 0.6 mcg, 0.7 mcg, 0.75 mcg, 0.8 mcg, 0.9 mcg, 1.0 mcg, 2.0 mcg, 3.0 mcg, 4.0 mcg, 5.0 mcg, 6.0 mcg, 7.0 mcg, 8.0 mcg, 9.0 mcg, 10.0 mcg, 11.0 mcg, 12.0 mcg, 13.0 mcg, 14.0 mcg, 15.0 mcg, 16.0 mcg, 17.0 mcg, 18.0 mcg, 19.0 mcg, 20.0 mcg, 25.0 mcg, 30.0 mcg, 40.0 mcg, 50.0 mcg, about 0.01 mcg, about 0.05 mcg, about 0.1 mcg, about 0.15 mcg, about 0.2 mcg, about 0.25 mcg, about 0.3 mcg, about 0.35 mcg, about 0.4 mcg, about 0.5 mcg, about 0.6 mcg, about 0.7 mcg, about 0.75 mcg, about 0.8 mcg, about 0.9 mcg, about 1.0 mcg, about 2.0 mcg, about 3.0 mcg, about 4.0 mcg, about 5.0 mcg, about 6.0 mcg, about 7.0 mcg, about 8.0 mcg, about 9.0 mcg, about 10.0 mcg, about 11.0 mcg, about 12.0 mcg, about 13.0 mcg, about 14.0 mcg, about 15.0 mcg, about 16.0 mcg, about 17.0 mcg, about 18.0 mcg, about 19.0 mcg, about 20.0 mcg, about 25.0 mcg, about 30.0 mcg, about 40.0 mcg, or about 50.0 mcg. In some embodiments, the system and/or apparatus is configured to provide an amount of the nicotine in the third vapor based on a typical puff volume (as defined above) or based on the user's individual puff volume as measured by the apparatus or as provided to the system, wherein the amount of nicotine is from about 0.0 mcg to about 250.0 mcg, from 0.0 mcg to 250.0 mcg, about 0.0 mcg to about 100.0 mcg, from 0.0 mcg to 100.0 mcg, from about 0.5 mcg to about 100.0 mcg, from 0.5 mcg to 100.0 mcg, from about 0.5 mcg to about 90.0 mcg, from 0.5 mcg to 90.0 mcg, from about 0.0 mcg to about 75.0 mcg, from 0.0 mcg to 75.0 mcg, 0.01 mcg, 0.05 mcg, 0.1 mcg, 0.15 mcg, 0.2 mcg, 0.25 mcg, 0.3 mcg, 0.35 mcg, 0.4 mcg, 0.5 mcg, 0.6 mcg, 0.7 mcg, 0.75 mcg, 0.8 mcg, 0.9 mcg, 1.0 mcg, 2.0 mcg, 3.0 mcg, 4.0 mcg, 5.0 mcg, 6.0 mcg, 7.0 mcg, 8.0 mcg, 9.0 mcg, 10.0 mcg, 11.0 mcg, 12.0 mcg, 13.0 mcg, 14.0 mcg, 15.0 mcg, 16.0 mcg, 17.0 mcg, 18.0 mcg, 19.0 mcg, 20.0 mcg, 21.0 mcg, 22.0 mcg, 23.0 mcg, 24.0 mcg, 25.0 mcg, 26.0 mcg, 27.0 mcg, 28.0 mcg, 29.0 mcg, 30.0 mcg, 31.0 mcg, 32.0 mcg, 33.0 mcg, 34.0 mcg, 35.0 mcg, 36.0 mcg, 37.0 mcg, 38.0 mcg, 39.0 mcg, 40.0 mcg, 41.0 mcg, 42.0 mcg, 43.0 mcg, 44.0 mcg, 45.0 mcg, 46.0 mcg, 47.0 mcg, 48.0 mcg, 49.0 mcg, 50.0 mcg, 51.0 mcg, 52.0 mcg, 53.0 mcg, 54.0 mcg, 55.0 mcg, 56.0 mcg, 57.0 mcg, 58.0 mcg, 59.0 mcg, 60.0 mcg, 61.0 mcg, 62.0 mcg, 63.0 mcg, 64.0 mcg, 65.0 mcg, 66.0 mcg, 67.0 mcg, 68.0 mcg, 69.0 mcg, 70.0 mcg, 71.0 mcg, 72.0 mcg, 73.0 mcg, 74.0 mcg, 75.0 mcg, 76.0 mcg, 77.0 mcg, 78.0 mcg, 79.0 mcg, 80.0 mcg, 81.0 mcg, 82.0 mcg, 83.0 mcg, 84.0 mcg, 85.0 mcg, 86.0 mcg, 87.0 mcg, 88.0 mcg, 89.0 mcg, 90.0 mcg, 91.0 mcg, 92.0 mcg, 93.0 mcg, 94.0 mcg, 95.0 mcg, 96.0 mcg, 97.0 mcg, 98.0 mcg, 99.0 mcg, 100.0 mcg, 0 mcg to 100 mcg in increments of 0.01 mcg, 0 mcg to 100 mcg in increments of 0.1 mcg, 0 mcg to 100 mcg in increments of 0.5 mcg, 0 mcg to 100 mcg in increments of 1 mcg, 0.5 mcg to 100 mcg in increments of 0.5-5 mcg, 0.0 mcg to 100 mcg in increments of 0.5 mcg to 5 mcg, 0.0 mcg to 150 mcg in increments of 0.5 mcg to 5 mcg, 0.0 mcg to 100 mcg in increments of 0.5 mcg to 25 mcg, about 0.01 mcg, about 0.05 mcg, about 0.1 mcg, about 0.15 mcg, about 0.2 mcg, about 0.25 mcg, about 0.3 mcg, about 0.35 mcg, about 0.4 mcg, about 0.5 mcg, about 0.6 mcg, about 0.7 mcg, about 0.75 mcg, about 0.8 mcg, about 0.9 mcg, about 1.0 mcg, about 2.0 mcg, about 3.0 mcg, about 4.0 mcg, about 5.0 mcg, about 6.0 mcg, about 7.0 mcg, about 8.0 mcg, about 9.0 mcg, about 10.0 mcg, about 11.0 mcg, about 12.0 mcg, about 13.0 mcg, about 14.0 mcg, about 15.0 mcg, about 16.0 mcg, about 17.0 mcg, about 18.0 mcg, about 19.0 mcg, about 20.0 mcg, about 21.0 mcg, about 22.0 mcg, about 23.0 mcg, about 24.0 mcg, about 25.0 mcg, about 26.0 mcg, about 27.0 mcg, about 28.0 mcg, about 29.0 mcg, about 30.0 mcg, about 31.0 mcg, about 32.0 mcg, about 33.0 mcg, about 34.0 mcg, about 35.0 mcg, about 36.0 mcg, about 37.0 mcg, about 38.0 mcg, about 39.0 mcg, about 40.0 mcg, about 41.0 mcg, about 42.0 mcg, about 43.0 mcg, about 44.0 mcg, about 45.0 mcg, about 46.0 mcg, about 47.0 mcg, about 48.0 mcg, about 49.0 mcg, about 50.0 mcg, about 51.0 mcg, about 52.0 mcg, about 53.0 mcg, about 54.0 mcg, about 55.0 mcg, about 56.0 mcg, about 57.0 mcg, about 58.0 mcg, about 59.0 mcg, about 60.0 mcg, about 61.0 mcg, about 62.0 mcg, about 63.0 mcg, about 64.0 mcg, about 65.0 mcg, about 66.0 mcg, about 67.0 mcg, about 68.0 mcg, about 69.0 mcg, about 70.0 mcg, about 71.0 mcg, about 72.0 mcg, about 73.0 mcg, about 74.0 mcg, about 75.0 mcg, about 76.0 mcg, about 77.0 mcg, about 78.0 mcg, about 79.0 mcg, about 80.0 mcg, about 81.0 mcg, about 82.0 mcg, about 83.0 mcg, about 84.0 mcg, about 85.0 mcg, about 86.0 mcg, about 87.0 mcg, about 88.0 mcg, about 89.0 mcg, about 90.0 mcg, about 91.0 mcg, about 92.0 mcg, about 93.0 mcg, about 94.0 mcg, about 95.0 mcg, about 96.0 mcg, about 97.0 mcg, about 98.0 mcg, about 99.0 mcg, about 100.0 mcg, about 0 mcg to about 100 mcg in increments of 0.01 mcg, about 0 mcg to about 100 mcg in increments of 0.1 mcg, about 0 mcg to about 100 mcg in increments of 0.5 mcg, about 0 mcg to about 100 mcg in increments of 1 mcg, about 0.5 mcg to about 100 mcg in increments of 0.5-5 mcg, about 0.0 mcg to about 100 mcg in increments of 0.5 mcg to 5 mcg, about 0.0 mcg to about 150 mcg in increments of 0.5 mcg to 5 mcg, or about 0.0 mcg to about 100 mcg in increments of 0.5 mcg to 25 mcg. In some embodiments, the system and/or apparatus is configured to modulate or adjust the amount of nicotine in the third vapor in increments of 1.0 mcg, 5.0 mcg, 10.0 mcg, 20.0 mcg, 25.0 mcg, 30.0 mcg, 40.0 mcg, 50.0 mcg, 75.0 mcg, 100.0 mcg, 150.0 mcg, 200.0 mcg, 250.0 mcg, about 1.0 mcg, about 5.0 mcg, about 10.0 mcg, about 20.0 mcg, about 25.0 mcg, about 30.0 mcg, about 40.0 mcg, about 50.0 mcg, about 75.0 mcg, about 100.0 mcg, about 150.0 mcg, about 200.0 mcg, about 250.0 mcg, less than 250.0 mcg, less than 200.0 mcg, less than 150.0 mcg, less than 100.0 mcg, less than 75.0 mcg, less than 50.0 mcg, less than 40.0 mcg, less than 30.0 mcg, less than 25.0 mcg, less than 20.0 mcg, less than 10.0 mcg, less than 5.0 mcg, greater than about 5.0 mcg, greater than about 10.0 mcg, greater than about 20.0 mcg, greater than about 25.0 mcg, greater than about 30.0 mcg, greater than about 40.0 mcg, greater than about 50.0 mcg, greater than about 75.0 mcg, greater than about 100.0 mcg, greater than about 150.0 mcg, greater than about 200.0 mcg and greater than about 250.0 mcg.

In some embodiments of the system and/or apparatus, in order to change the third vapor, the digital processing device is configured to modulate an amount of the first liquid substance in the third vapor according to the nicotine management plan. Generally, speaking, the first liquid substance comprises nicotine, or some form thereof, referred to generally as "nicotine" herein. Additionally the first liquid substance has an unchanging formulation (i.e. composition and/or concentration of nicotine in the first liquid substance)

in a given first cartridge chamber. Thus, changing the amount of first liquid substance in the third vapor, or the amount that is formed into first vapor to become part of the third vapor, will change the amount of nicotine delivered to a user. The amount of first liquid substance may be measured as an amount of first liquid substance formed into the first vapor, or as an amount of first vapor in the third vapor. In some embodiments, the amount of first liquid substance is measured as a volume of first vapor in a typical puff volume, in a standardized volume (e.g. per 100 ml of third vapor), or in a user's typical puff volume, as elsewhere described herein. In some embodiments, the amount of first liquid substance is about 0 ml to about 175 ml, about 0 ml to about 150 ml, about 0 ml to about 100 ml, about 0 ml to about 75 ml, about 0 ml to about 50 ml, about 0 ml to about 40 ml, about 0 ml, about 0.1 ml, about 1 ml, about 2 ml, about 3 ml, about 4 ml, about 5 ml, about 6 ml, about 7 ml, about 8 ml, about 9 ml, about 10 ml, about 11 ml, about 12 ml, about 13 ml, about 14 ml, about 15 ml, about 16 ml, about 17 ml, about 18 ml, about 19 ml, about 20 ml, about 21 ml, about 22 ml, about 23 ml, about 24 ml, about 25 ml, about 26 ml, about 27 ml, about 28 ml, about 29 ml, about 30 ml, about 31 ml, about 32 ml, about 33 ml, about 34 ml, about 35 ml, about 36 ml, about 37 ml, about 38 ml, about 39 ml, about 30 ml, about 41 ml, about 42 ml, about 43 ml, about 44 ml, about 45 ml, about 46 ml, about 47 ml, about 48 ml, about 49 ml, about 50 ml, about 1 ml to about 100 ml, about 1 ml to about 99 ml, about 1 ml to about 50 ml, about 1 ml to about 35 ml, about 2 ml to about 50 ml, about 5 ml to about 25 ml, 0 ml to 175 ml, 0 ml to 150 ml, 0 ml to 100 ml, 0 ml to 75 ml, 0 ml to 50 ml, 0 ml to 40 ml, 0 ml, 1 ml, 2 ml, 3 ml, 4 ml, 5 ml, 6 ml, 7 ml, 8 ml, 9 ml, 10 ml, 11 ml, 12 ml, 13 ml, 14 ml, 15 ml, 16 ml, 17 ml, 18 ml, 19 ml, 20 ml, 21 ml, 22 ml, 23 ml, 24 ml, 25 ml, 26 ml, 27 ml, 28 ml, 29 ml, 30 ml, 31 ml, 32 ml, 33 ml, 34 ml, 35 ml, 36 ml, 37 ml, 38 ml, 39 ml, 30 ml, 41 ml, 42 ml, 43 ml, 44 ml, 45 ml, 46 ml, 47 ml, 48 ml, 49 ml, 50 ml, 1 ml to 100 ml, 1 ml to 99 ml, 1 ml to 50 ml, 1 ml to 35 ml, 2 ml to 50 ml, or 5 ml to 25 ml. In some embodiments, the amount of first vapor can be modulated using the digital processing device according to the management plan in increments of about 0.1 ml to about 25 ml, about 0.1 ml to about 10 ml, 0.1 ml to 25 ml, 0.1 ml to 10 ml, about 0.1 ml, about 0.2 ml, about 0.3 ml, about 0.4 ml, about 0.5 ml, about 0.6 ml, about 0.7 ml, about 0.8 ml, about 0.9 ml, about 1.0 ml, about 2 ml, about 5 ml, about 7.5 ml, about 10 ml, about 15 ml, about 20 ml, about 25 ml, 0.1 ml to 10 ml, 0.1 ml, 0.2 ml, 0.3 ml, 0.4 ml, 0.5 ml, 0.6 ml, 0.7 ml, 0.9 ml, 1.0 ml, 2 ml, 5 ml, 7.5 ml, 10 ml, 15 ml, 20 ml, or 25 ml.

In some embodiments of the system and/or apparatus, in order to change the third vapor, the digital processing device is configured to modulate an amount of the second liquid substance in the third vapor according to the nicotine management plan. Another way to change the amount of nicotine delivered to a user is to make the amount of first vapor produced constant, but change the amount of second vapor formed by the apparatus. This is effective, for example, when a puff volume is less than the volume of third vapor produced by the apparatus, such that although the nicotine amount is constant in the third vapor (because the first vapor amount is constant), the amount delivered by a puff is lower depending on the amount of second vapor added to the first vapor. For non-limiting example, for a given puff (having a typical puff volume, a user's puff volume, or a standard volume as described elsewhere herein), the amount of third vapor may be greater than the volume of the puff. The amount of second vapor in the third vapor may be about 0 ml to about 175 ml, about 0 ml to about 150 ml, about 0 ml to about 100 ml, about 0 ml to about 75 ml, about 0 ml to about 50 ml, about 0 ml to about 40 ml, about 0 ml, about 1 ml, about 2 ml, about 3 ml, about 4 ml, about 5 ml, about 6 ml, about 7 ml, about 8 ml, about 9 ml, about 10 ml, about 11 ml, about 12 ml, about 13 ml, about 14 ml, about 15 ml, about 16 ml, about 17 ml, about 18 ml, about 19 ml, about 20 ml, about 21 ml, about 22 ml, about 23 ml, about 24 ml, about 25 ml, about 26 ml, about 27 ml, about 28 ml, about 29 ml, about 30 ml, about 31 ml, about 32 ml, about 33 ml, about 34 ml, about 35 ml, about 36 ml, about 37 ml, about 38 ml, about 39 ml, about 30 ml, about 41 ml, about 42 ml, about 43 ml, about 44 ml, about 45 ml, about 46 ml, about 47 ml, about 48 ml, about 49 ml, about 50 ml, about 1 ml to about 100 ml, about 1 ml to about 99 ml, about 1 ml to about 50 ml, about 1 ml to about 35 ml, about 2 ml to about 50 ml, about 5 ml to about 25 ml, 0 ml to 175 ml, 0 ml to 150 ml, 0 ml to 100 ml, 0 ml to 75 ml, 0 ml to 50 ml, 0 ml to 40 ml, 0 ml, 1 ml, 2 ml, 3 ml, 4 ml, 5 ml, 6 ml, 7 ml, 8 ml, 9 ml, 10 ml, 11 ml, 12 ml, 13 ml, 14 ml, 15 ml, 16 ml, 17 ml, 18 ml, 19 ml, 20 ml, 21 ml, 22 ml, 23 ml, 24 ml, 25 ml, 26 ml, 27 ml, 28 ml, 29 ml, 30 ml, 31 ml, 32 ml, 33 ml, 34 ml, 35 ml, 36 ml, 37 ml, 38 ml, 39 ml, 30 ml, 41 ml, 42 ml, 43 ml, 44 ml, 45 ml, 46 ml, 47 ml, 48 ml, 49 ml, 50 ml, 1 ml to 100 ml, 1 ml to 99 ml, 1 ml to 50 ml, 1 ml to 35 ml, 2 ml to 50 ml, or 5 ml to 25 ml. In some embodiments, the amount of second vapor can be modulated using the digital processing device according to the management plan in increments of about 0.1 ml to about 25 ml, about 0.1 ml to about 10 ml, 0.1 ml to 25 ml, 0.1 ml to 10 ml, about 0.1 ml, about 0.2 ml, about 0.3 ml, about 0.4 ml, about 0.5 ml, about 0.6 ml, about 0.7 ml, about 0.8 ml, about 0.9 ml, about 1.0 ml, about 2 ml, about 5 ml, about 7.5 ml, about 10 ml, about 15 ml, about 20 ml, about 25 ml, 0.1 ml to 10 ml, 0.1 ml, 0.2 ml, 0.3 ml, 0.4 ml, 0.5 ml, 0.6 ml, 0.7 ml, 0.9 ml, 1.0 ml, 2 ml, 5 ml, 7.5 ml, 10 ml, 15 ml, 20 ml, or 25 ml. In some embodiments of the system and/or apparatus, in order to change the third vapor, the digital processing device is configured to modulate an amount of the second liquid substance in the second vapor according to the nicotine management plan. Modulating the second liquid substance amount as a proxy for the amount of second vapor may also be employed as a method of changing the amount of nicotine in a puff of the third vapor, or the percent of nicotine in the third vapor. As with the prior example of modulating the amount of second vapor in the third vapor, modulating the second liquid substance in the third vapor is effective, for example, when a puff volume is less than the volume of third vapor produced by the apparatus, such that although the nicotine amount is constant in the third vapor (because the first vapor amount is constant), the amount delivered by a puff is lower depending on the amount of second liquid substance added to the first vapor (in the form of a second vapor). For non-limiting example, for a given puff (having a typical puff volume, a user's puff volume, or a standard volume as described elsewhere herein), the amount of third vapor may be greater than the volume of the puff. The amount of second liquid substance in the third vapor may be about 0 ml to about 175 ml, about 0 ml to about 150 ml, about 0 ml to about 100 ml, about 0 ml to about 75 ml, about 0 ml to about 50 ml, about 0 ml to about 40 ml, about 0 ml, about 1 ml, about 2 ml, about 3 ml, about 4 ml, about 5 ml, about 6 ml, about 7 ml, about 8 ml, about 9 ml, about 10 ml, about 11 ml, about 12 ml, about 13 ml, about 14 ml, about 15 ml, about 16 ml, about 17 ml, about 18 ml, about 19 ml, about 20 ml, about 21 ml, about 22 ml, about 23 ml, about 24 ml, about 25 ml, about 26 ml, about 27 ml, about 28 ml, about 29 ml, about 30 ml, about 31 ml, about 32 ml, about 33 ml, about 34 ml, about 35 ml, about 36 ml, about 37 ml, about 38 ml, about 39 ml, about 30 ml, about 41 ml, about 42 ml, about 43 ml, about 44 ml, about 45 ml, about 46 ml, about 47 ml, about 48 ml, about 49 ml, about 50 ml, about 1 ml to about 100 ml, about 1 ml to about 99 ml, about 1 ml to about 50 ml, about 1 ml to about 35 ml, about 2 ml to about 50 ml, about 5 ml to about 25 ml, 0 ml to 175 ml, 0 ml to 150 ml, 0 ml to 100 ml, 0 ml to 75 ml, 0 ml to 50 ml, 0 ml to 40 ml, 0 ml, 1 ml, 2 ml, 3 ml, 4 ml, 5 ml, 6 ml, 7 ml, 8 ml, 9 ml, 10 ml, 11 ml, 12 ml, 13 ml, 14 ml, 15 ml, 16 ml, 17 ml, 18 ml, 19 ml, 20 ml, 21 ml, 22 ml, 23 ml, 24 ml, 25 ml, 26 ml, 27 ml, 28 ml, 29 ml, 30 ml, 31 ml, 32 ml, 33 ml, 34 ml, 35 ml, 36 ml, 37 ml, 38 ml, 39 ml, 30 ml, 41 ml, 42 ml, 43 ml, 44 ml, 45 ml, 46 ml, 47 ml, 48 ml, 49 ml, 50 ml, 1 ml to 100 ml, 1 ml to 99 ml, 1 ml to 50 ml, 1 ml to 35 ml, 2 ml to 50 ml, or 5 ml to 25 ml. In some embodiments, the amount of second liquid substance can be modulated using the digital processing device according to the management plan in increments of about 0.1 ml to about 25 ml, about 0.1 ml to about 10 ml, 0.1 ml to 25 ml, 0.1 ml to 10 ml, about 0.1 ml, about 0.2 ml, about 0.3 ml, about 0.4 ml, about 0.5 ml, about 0.6 ml, about 0.7 ml, about 0.8 ml, about 0.9 ml, about 1.0 ml, about 2 ml, about 5 ml, about 7.5 ml, about 10 ml, about 15 ml, about 20 ml, about 25 ml, 0.1 ml to 10 ml, 0.1 ml, 0.2 ml, 0.3 ml, 0.4 ml, 0.5 ml, 0.6 ml, 0.7 ml, 0.9 ml, 1.0 ml, 2 ml, 5 ml, 7.5 ml, 10 ml, 15 ml, 20 ml, or 25 ml.

In some embodiments of the system and/or apparatus, in order to change the third vapor, the digital processing device is configured to modulate a percentage of the first liquid substance in the third vapor according to the nicotine management plan. The system and/or apparatus may be configured to control the nicotine in the third vapor by determining a percentage of first liquid substance in the third substance. In some embodiments, the system and/or apparatus is configured to modulate the percentage of first liquid substance in the third vapor from about 0% to about 100%, from 0% to 100%, from about 0.01% to about 99.99%, from 0.01% to 99.99%, from about 0.05% to about 99.95%, from about 0.1% to about 99.9%, from 0.1% to about 99.9%, from about 0.5% to about 99.5%, from 0.5% to 99.5%, from about 0% to about 90%, from 0% to 90%, from about 0% to about 80%, from 0% to 80%, from about 0% to about 75%, from 0% to 75%, from about 0% to about 10%, from 0% to 10%, from about 0.01% to about 10%, from 0.01% to 10%, from about 0% to about 25%, from 0% to 25%, from about 0.01% to about 25%, and/or from 0.01% to 25%. In some embodiments, the system and/or apparatus is configured to change the percentage of first liquid substance in the third vapor in increments of 100%, 50%, 40%, 35%, 30%, 25%, 20%, 15%, 10%, 9%, 8%, 7%, 7.5%, 6%, 5%, 4%, 3%, 2%, 1%, 0.5%, 0.1%, 0.05%, 0.01%, about 100%, about 50%, about 40%, about 35%, about 30%, about 25%, about 20%, about 15%, about 10%, about 9%, about 8%, about 7%, about 7.5%, about 6%, about 5%, about 4%, about 3%, about 2%, about 5%, about 1%, about 0.5%, about 0.1%, about 0.05%, about 0.01%, less than 100%, less than 50%, less than 20%, less than 10%, less than 5%, less than 1%, less than 0.5%, less than 0.1%, less than 0.05%, less than 0.01%, greater than about 50%, greater than about 20%, greater than about 10%, greater than about 5%, greater than about 1%, greater than about 0.5%, greater than about 0.1%, greater than about 0.05%, and/or greater than about 0.01%.

In some embodiments of the system and/or apparatus, in order to change the third vapor, the digital processing device is configured to modulate a percentage of the second liquid substance in the third vapor according to the nicotine management plan. The system and/or apparatus may be configured to control the nicotine in the third vapor by modulating a percentage of second liquid substance in the third substance. In some embodiments, the system and/or apparatus is configured to modulate the percentage of second liquid substance in the third vapor from about 0% to about 100%, from 0% to 100%, from about 0.01% to about 99.99%, from 0.01% to 99.99%, from about 0.05% to about 99.95%, from about 0.1% to about 99.9%, from 0.1% to about 99.9%, from about 0.5% to about 99.5%, from 0.5% to 99.5%, from about 10% to about 100%, from 10% to 90%, from about 20% to about 100%, from 20% to 90%, from about 25% to about 95%, from 20% to 95%, from about 0% to about 80%, from 0% to 75%, from about 10% to about 100%, from 50% to 100%, from about 60% to about 95%, from 50% to 25%, from about 50% to about 99.5%, and/or from 0.01% to 99.5%. In some embodiments, the system and/or apparatus is configured to change the percentage of second liquid substance in the third vapor in increments of 100%, 50%, 40%, 35%, 30%, 25%, 20%, 15%, 10%, 9%, 8%, 7%, 7.5%, 6%, 5%, 4%, 3%, 2%, 1%, 0.5%, 0.1%, 0.05%, 0.01%, about 100%, about 50%, about 40%, about 35%, about 30%, about 25%, about 20%, about 15%, about 10%, about 9%, about 8%, about 7%, about 7.5%, about 6%, about 5%, about 4%, about 3%, about 2%, about 5%, about 1%, about 0.5%, about 0.1%, about 0.05%, about 0.01%, less than 100%, less than 50%, less than 20%, less than 10%, less than 5%, less than 1%, less than 0.5%, less than 0.1%, less than 0.05%, less than 0.01%, greater than about 50%, greater than about 20%, greater than about 10%, greater than about 5%, greater than about 1%, greater than about 0.5%, greater than about 0.1%, greater than about 0.05%, and/or greater than about 0.01%.

In some embodiments of the system and/or apparatus, in order to change the third vapor, the digital processing device is configured to modulate a percentage of nicotine in the third vapor according to the nicotine management plan. In some embodiments, the system and/or apparatus is configured to modulate the percentage of nicotine in the third vapor from about 0% to about 100%, from 0% to 100%, from about 0.01% to about 99.99%, from 0.01% to 99.99%, from about 0.05% to about 99.95%, from about 0.1% to about 99.9%, from 0.1% to about 99.9%, from about 0.5% to about 99.5%, from 0.5% to 99.5%, from about 0% to about 90%, from 0% to 90%, from about 0% to about 80%, from 0% to 80%, from about 0% to about 75%, from 0% to 75%, from about 0% to about 10%, from 0% to 10%, from about 0.01% to about 10%, from 0.01% to 10%, from about 0% to about 25%, from 0% to 25%, from about 0.01% to about 25%, and/or from 0.01% to 25%. In some embodiments, the system and/or apparatus is configured to change the percentage of nicotine in the third vapor in increments of 100%, 50%, 40%, 35%, 30%, 25%, 20%, 15%, 10%, 9%, 8%, 7%, 7.5%, 6%, 5%, 4%, 3%, 2%, 1%, 0.5%, 0.1%, 0.05%, 0.01%, about 100%, about 50%, about 40%, about 35%, about 30%, about 25%, about 20%, about 15%, about 10%, about 9%, about 8%, about 7%, about 7.5%, about 6%, about 5%, about 4%, about 3%, about 2%, about 5%, about 1%, about 0.5%, about 0.1%, about 0.05%, about 0.01%, less than 100%, less than 50%, less than 20%, less than 10%, less than 5%, less than 1%, less than 0.5%, less than 0.1%, less than 0.05%, less than 0.01%, greater than about 100%, greater than about 50%, greater than about 20%, greater than about 10%, greater than about 5%, greater than about 1%, greater than about 0.5%, greater than about 0.1%, greater than about 0.05%, and/or greater than about 0.01%.

In some embodiments of the system and/or apparatus, in order to change the third vapor, the digital processing device is configured to modulate a ratio of the first liquid substance to the second substance in the third vapor according to the nicotine management plan. In some embodiments, the ratio of first vapor to second vapor in the third vapor is 0.01:99.9, or from 0:100 to 100:0, 1:99, 2:98, 3:97, 4:96, 5:95, 6:94, 7:93, 8:92, 8:91, 10:90, 11:89, 12:88, 13:87, 14:86, 15:85, 16:84, 17:83, 18:82, 19:81, 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, and/or about 100:0. The system and/or apparatus is configured to adjust the ratio in fine increments, modulating the ratio from, for nonlimiting example 85:15 to 84:16 to 83:17, etc based on the management plan, or even finer increments of 85:15 to 84.5:15.5, etc., at least.

The system and/or apparatus is configured to adjust the amount of nicotine in the third vapor delivered or deliverable to a user with fine control. There are multiple ways this could be achieved, as noted herein, and as is available to one using the dual chamber device that controls the release of the first vapor comprising nicotine and/or second vapor in order to deliver the third vapor.

In some embodiments of the system and/or apparatus, the first vapor comprises nicotine freebase, and the second vapor comprises pyruvic acid, wherein a chemical reaction occurs between the first vapor and the second vapor to form the third vapor comprising nicotine pyruvate. In some embodiments of the system and/or apparatus, the first vapor comprises nicotine freebase, and the second vapor comprises lactic acid, wherein a chemical reaction occurs between the first vapor and the second vapor to form the third vapor comprising nicotine lactate.

In some embodiments the first vapor comprises 1,2-propanediol (propylene glycol) and nicotine. In some embodiments the first vapor comprises 1,3-propanediol and nicotine. In some embodiments the second vapor comprises 1,2-propanediol (propylene glycol). In some embodiments the first vapor comprises 1,3-propanediol. In some embodiments the second vapor comprises 1,2-propanediol (propylene glycol) and a flavorant. In some embodiments the first vapor comprises 1,3-propanediol and a flavorant. In some embodiments the first vapor comprises 1,2-propanediol (propylene glycol) and 1,3-propanediol and nicotine. In some embodiments the second vapor comprises 1,2-propanediol (propylene glycol) and 1,3-propanediol. In some embodiments the second vapor comprises 1,2-propanediol (propylene glycol) and 1,3-propanediol and a flavorant.

In some embodiments the flavorant is chosen to impart a smoke, mint, fruit, clove, coffee, tobacco, tea, vanilla, cinnamon, nut, caramel, chocolate, cola, or other flavor to the third vapor. In some embodiments the flavorant comprises a smoke flavor, a mint flavor, a fruit flavor, a clove flavor, a coffee flavor, a tobacco flavor, a tea flavor, a vanilla flavor, a cinnamon flavor, a nut flavor, a caramel flavor, a chocolate flavor, a cola flavor, a or other flavor to the third vapor.

In some embodiments of the system and/or apparatus, the digital processing device comprises on-board memory configured to: store an operating system or computer program configured to perform the instructions; and record a first set of data and a second set of data. In some embodiments, the first set of data comprises vaporization characteristics comprising one or more of: a first power reading of power delivered to the first heater, a second power reading of power delivered to the second heater, a first duration of energization delivered to the first heater, a second duration of energization delivered to the second heater, and a simple pulse signal profile or a pulse width modulation signal profile. In some embodiments of the system, the flow sensor analyzer is configured to detect and record a second set of data comprising one or more of: a date of each user puff; a time of each user puff; a duration of each user puff; an amount of nicotine released to a user; a puff flow; a puff intensity; and an airflow rate within the vapor release mechanism. In some embodiments of the system, the digital processing device comprises on-board memory and wherein the second set of data is stored in the on-board memory.

Some embodiments comprise a third chamber comprising a third liquid substance that is configured to generate a fourth vapor in a third chamber that is part of the third vapor along with the first vapor and/or the second vapor.

In any of the above embodiments, the second liquid substance may also or alternatively comprise nicotine, and one of skill in the art may apply the same principles without departing from the disclosure herein, in order to finely control the amount of nicotine delivered to a user over time and in accordance with a management plan.

In some embodiments, the first liquid substance comprises a flavorant. In some embodiments, the second liquid substance comprises nicotine. In some embodiments, the second liquid substance comprises no nicotine.

In other embodiments, the second liquid substance comprises a flavorant. In some embodiments, the second liquid substance comprises a non-nicotine liquid. In still other embodiments, the non-nicotine liquid is a flavorant.

In some embodiments the flavorant is chosen to impart a smoke, mint, fruit, clove, coffee, tobacco, tea, vanilla, cinnamon, nut, caramel, chocolate, cola, or other flavor to the third vapor. In some embodiments the flavorant comprises a smoke flavor, a mint flavor, a fruit flavor, a clove flavor, a coffee flavor, a tobacco flavor, a tea flavor, a vanilla flavor, a cinnamon flavor, a nut flavor, a caramel flavor, a chocolate flavor, a cola flavor, a or other flavor to the third vapor.

In some embodiments of the system and/or apparatus, the vaporizer housing is configured to receive an attachable mouthpiece. In some embodiments, the mouthpiece is replaceable. In some embodiments, the vaporizer housing is replaceable.

In some embodiments of the system and/or apparatus the digital processing device is configured to execute the instructions defined by the computer program based on the nicotine management plan wherein the vapor release mechanism produces the third vapor having a consistent characteristic regardless of the ratio of the first vapor to the second vapor. In some embodiments of the system and/or apparatus, the nicotine management plan gradually diminishes the amount or percentage of nicotine in the third vapor over a specified period of time. In some embodiments, the characteristic comprises: measurable amounts of nicotine in the third vapor or measurable percentage of nicotine in the third vapor generated by the electronic vaporizing apparatus; and/or measurable amounts of flavorant in the third vapor or measurable percentage of flavorant in the third vapor generated by the electronic vaporizing apparatus. In some embodiments of the system and/or apparatus, the vapor characteristic produced with each puff comprise: vapor intensity (measurable as vapor flow rate), vapor volume, vapor density (measured by spectrophotometry methods known to one of skill in the art), vapor flavor, and/or oral sensation, wherein the characteristic is consistent irrespective of nicotine levels. In some embodiments of the system and/or apparatus, the vapor characteristic produced with each puff comprises vapor intensity (measurable as vapor flow rate). In some embodiments of the system and/or apparatus, the vapor characteristic produced with each puff comprises vapor volume. In some embodiments of the system and/or apparatus, the vapor characteristic produced with each puff comprises vapor density (measured by spectrophotometry methods known to one of skill in the art). In some embodiments of the system and/or apparatus, the vapor characteristic produced with each puff comprises vapor flavor, and/or oral sensation. In some embodiments the flavorant is chosen to impart a smoke, mint, fruit, clove, coffee, tobacco, tea, vanilla, cinnamon, nut, caramel, chocolate, cola, or other flavor to the third vapor. In some embodiments the flavorant comprises a smoke flavor, a mint flavor, a fruit flavor, a clove flavor, a coffee flavor, a tobacco flavor, a tea flavor, a vanilla flavor, a cinnamon flavor, a nut flavor, a caramel flavor, a chocolate flavor, a cola flavor, a or other flavor to the third vapor.

In some embodiments, the system and/or apparatus comprises an override feature, configurable to override the digital processing device to modify the amount or percentage of the nicotine dispensed. In some embodiments, the override feature is manual. In some embodiments, the override feature is automatic.

In some embodiments of the system, the microprocessor is configured to control communication systems and input/output program functions for the apparatus. In some embodiments, the electronic communication system for communicating with one or more other electronic device comprises: a wireless communication link; and a wired communication link, wherein the other electronic device comprises: a computer; a mobile device; a computer network; and an electronic storage data device. In some embodiments of the system, the first cartridge chamber and the second chamber are in series arrangement, are in parallel arrangement, and/or comprise a central vapor flow path through a vaporization chamber common to the first cartridge and the second cartridge. In some embodiments of the system, the durable housing comprises at least one of: a power source; a connection interface configured to connect the durable housing to the vaporizer housing; an LED; a battery contact; and a charging interface circuit.

FIG. 1A shows an illustrative isometric view of an exemplary electronic vaporizing apparatus assembly and exploded sub-assembly thereof 100 constructed according to the principles of the disclosure. The vaporizing apparatus 100 may be disposable or reusable. The vaporizing apparatus 100 may have a multi-body construction including two or more bodies. For example, the vaporizing apparatus 100 may comprise an attachable durable housing 101 and a vaporizer housing 102 with or without a mouthpiece 103 and/or the like, that may be easily connected to and disconnected from each other anytime without using any special tools. For example, each housing may include threaded, press fit, bayonette or snap-feature connections 104, 105. Each housing may be covered by a different housing casing 111, 220. The vaporizer housing 102 may contain consumable liquids in separate cartridge chambers, such as, e.g., a first liquid substance, a second liquid substance, another vaporizing liquid. When the consumable liquid is fully, substantially, or partially consumed by vaporization by the apparatus, the vaporizer housing 102 may be disconnected from the first durable housing 101 and replaced with a new one. Alternatively, the vaporizer housing 102 may be disconnected from the first durable housing 101 and replaced with a new one regardless of consumption level. Also, the vaporizer housing 102 may be replaced with another one having a different flavor=in its cartridge chamber. Regardless of the construction type, the vaporizing apparatus 100 may have an elongated shape with a first end and a second end, as shown in FIG. 1A, which may be similar to a conventional cigarette shape. Other non-conventional shapes are also contemplated. For example, the vaporizing apparatus 100 may have a cigar or smoking pipe shape. The apparatus shown in FIG. 1A may also have a wired communication link, such as a micro USB 144.

In some embodiments of the system, the vapor release mechanism is configured to independently or simultaneously vaporize variable amounts of the first liquid substance and the second liquid substance.

Figure 1B:
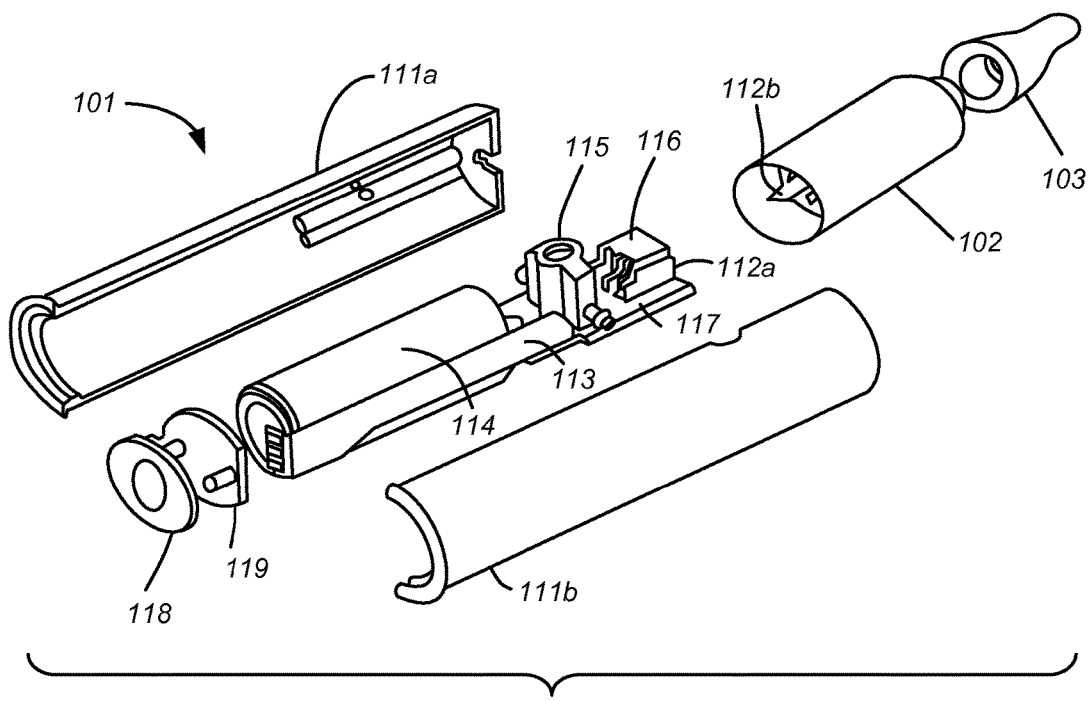
FIG. 1B is an illustrative exploded sub-assembly arrangement of FIG. 1A.
Figure 1C:
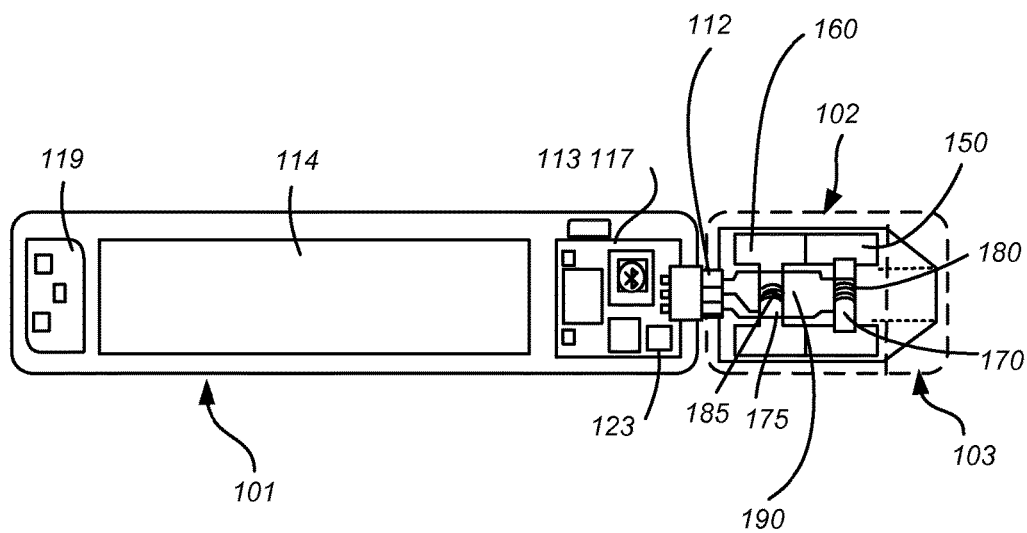
FIG. 1C is an illustrative general vaporizer assembly schematic of FIG. 1A
Figure 4A:
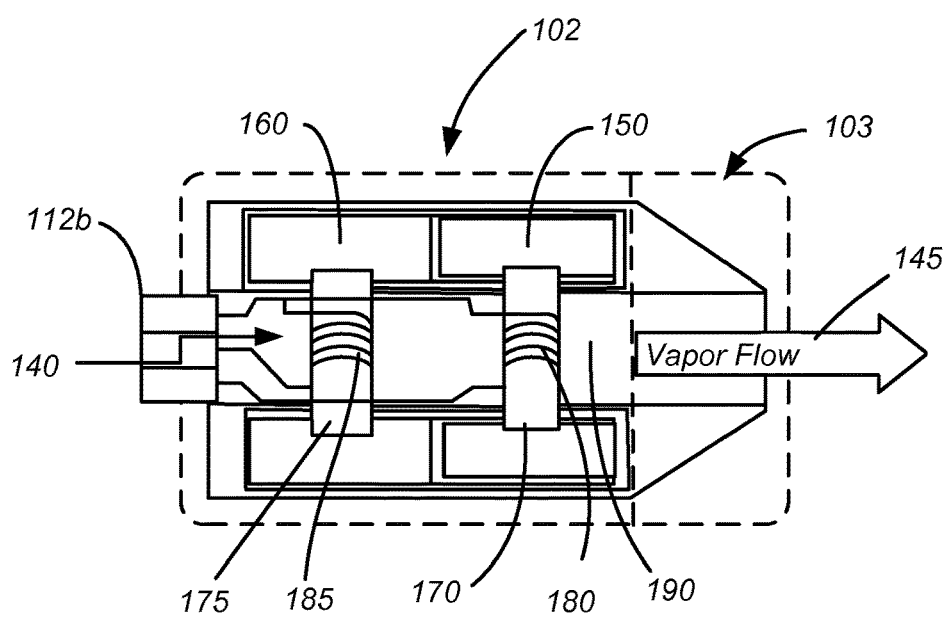
FIG. 4A is an illustrative general simplified schematic view of an exemplary dual cartridge chamber, series arrangement reservoir, vaporization housing and mouthpiece of an embodiment apparatus and/or system.
Figure 4B:
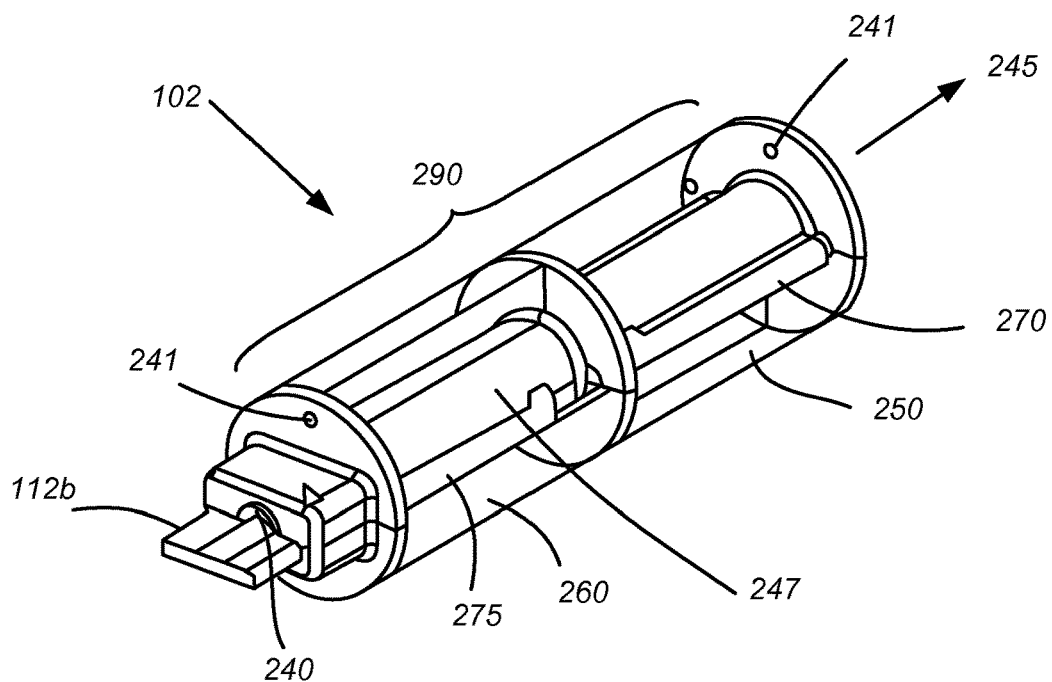
FIG. 4B is an illustrative ISO view of an exemplary dual cartridge chamber, series arrangement reservoir, vaporization housing with the cover removed of an embodiment apparatus and/or system.
Figure 4C:
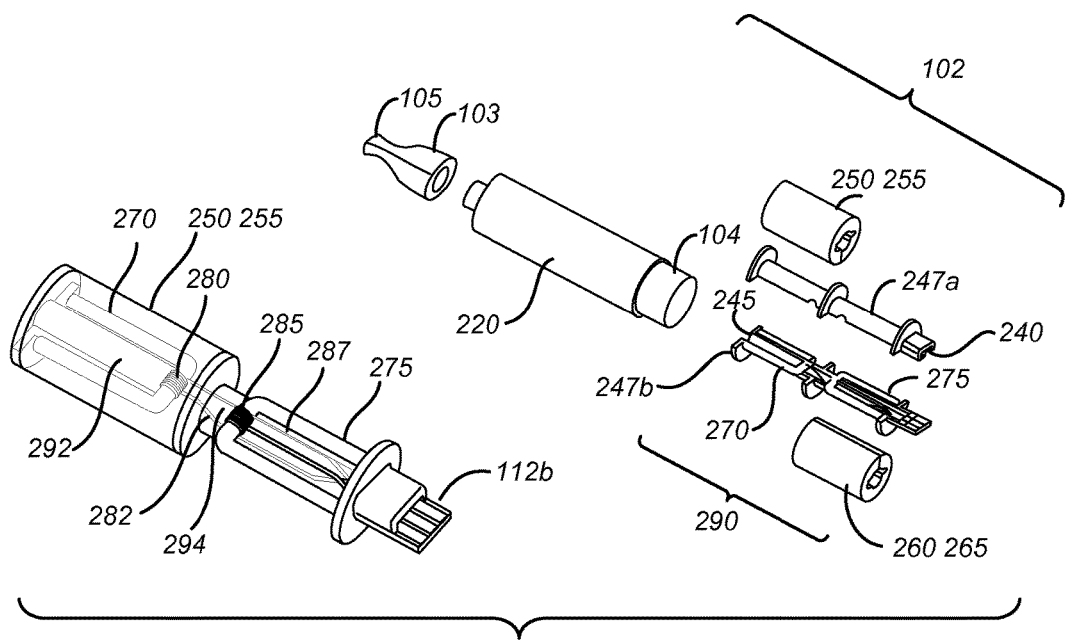
FIG. 4C is an illustrative ISO view of an exemplary dual cartridge chamber, series arrangement reservoir, vaporization housing and mouthpiece exploded assembly and cut-away partial section view of the series arrangement reservoir, vaporization housing with the cover removed of an embodiment apparatus and/or system.

In some embodiments of the system as illustrated in FIG. 4C, the vapor release mechanism 290 comprises: a first heater 285 coupled to a first wick 275, a second heater 280 coupled to a second wick 270, a first control circuit 287 coupled to the first heater 285, a second control circuit 282 coupled to the second heater 280, and a first vaporization chamber 294, wherein the first wick 275 is configured to draw the first liquid substance in proximity to or in contact with the first heater 285, wherein the second wick 270 is configured to draw the second liquid substance in proximity to or in contact with the second heater 280, and wherein the first heater and second heater are in fluid communication with the first vaporization chamber 294, wherein the first control circuit and the second control circuit are part of the digital processing device 113/117 as illustrated in FIG. 1C, and wherein the digital processing device is configured to modulate the amount of the first liquid substance drawn by the first wick to the first heater using the first control circuit and to modulate the amount of the second liquid substance drawn by the second wick to the second heater using the second control circuit. The first heater may comprise a first heater coil configured to heat the first liquid substance in the first wick to vaporize the first liquid substance. The second heater may comprise a second heater coil configured to heat the second liquid substance in the second wick to vaporize the second liquid substance. The first heater may comprise a first foil heater circuit configured to heat the first liquid substance in the first wick (alternatively called a first wicking surface) to vaporize the first liquid substance. The second heater may comprise a second foil heater circuit configured to heat the second liquid substance in the second wick (alternatively called a second wicking surface) to vaporize the second liquid substance.

In some embodiments, the vapor release mechanism comprises a first sensor (not shown) that detects a volume of the first liquid substance in the first cartridge chamber 260. In some embodiments, the vapor release mechanism comprises a second sensor (not shown) that detects a volume of the second liquid substance in the second cartridge chamber 250.

As illustrated in FIG. 4C, the systems disclosed herein may comprise a connection interface (e.g. 104, 105, 112b), a housing casing (e.g. 220), an air flow inlet 240, a vapor flow path 245 and/or a multi-chamber release mechanism core 247.

In some embodiments, the system comprises a vaporizer housing 102 comprising a first cartridge 260 comprising the first cartridge chamber 265, a second cartridge 250 comprising the second cartridge chamber 255, and the vapor release mechanism that includes a first heater 280 and/or a second heater 285, or a third cartridge 290 comprising the first cartridge chamber 265, the second cartridge chamber 255, and the vapor release mechanism that includes a first heater 280 and/or a second heater 285. The first heater may comprise a first heater coil configured to heat the first liquid substance in the first wick to vaporize the first liquid substance. The second heater may comprise a second heater coil configured to heat the second liquid substance in the second wick to vaporize the second liquid substance. The first heater may comprise a first foil heater circuit configured to heat the first liquid substance in the first wick (alternatively called a first wicking surface) to vaporize the first liquid substance. The second heater may comprise a second foil heater circuit configured to heat the second liquid substance in the second wick (alternatively called a second wicking surface) to vaporize the second liquid substance.

In some embodiments, the system comprises a durable housing 101 as illustrated in FIG. 1C, comprising the digital processing device 113/117 or a portion thereof. In some embodiments, the durable housing 101 is coupled integrally with or removably from the vaporizer housing 102. In some embodiments of the system, the durable housing comprises at least one of: a power source; a connection interface configured to connect the durable housing to the vaporizer housing; an LED; a battery contact; and a charging interface circuit. In some embodiments, the system comprises a second cartridge chamber 150, a first cartridge chamber 160, a first wick 175, first heater 185, a second wick 170, a second heater 180, a vaporization chamber 190 or any combination thereof.

Figure 3A:
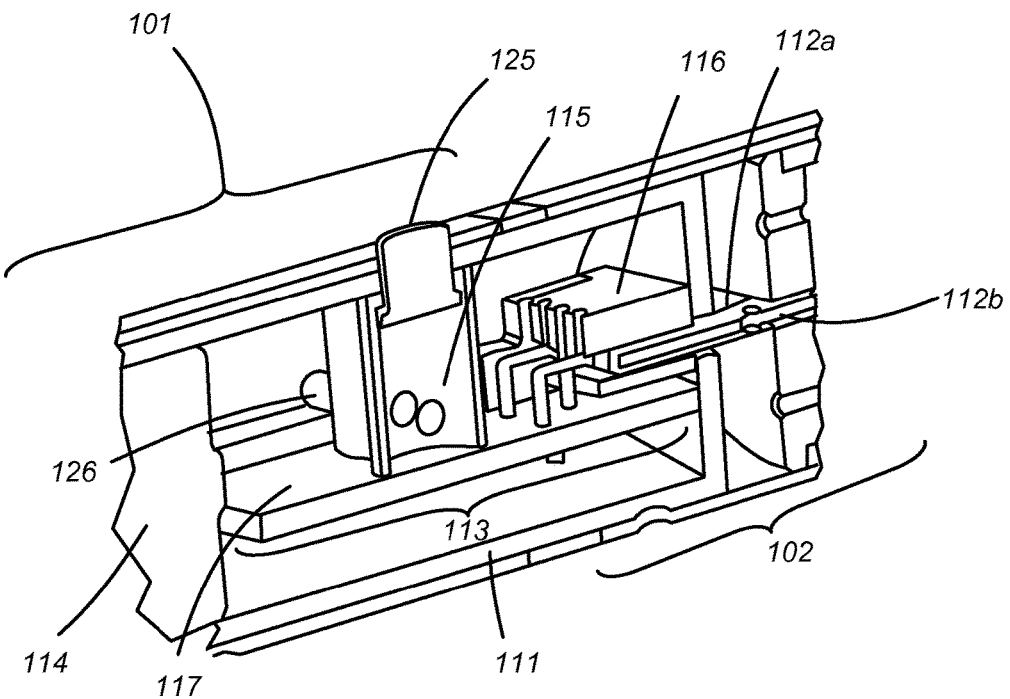
FIG. 3A is a side ISO view of an example configuration for a printed circuit assembly of an embodiment apparatus and/or system.
Figure 3B:
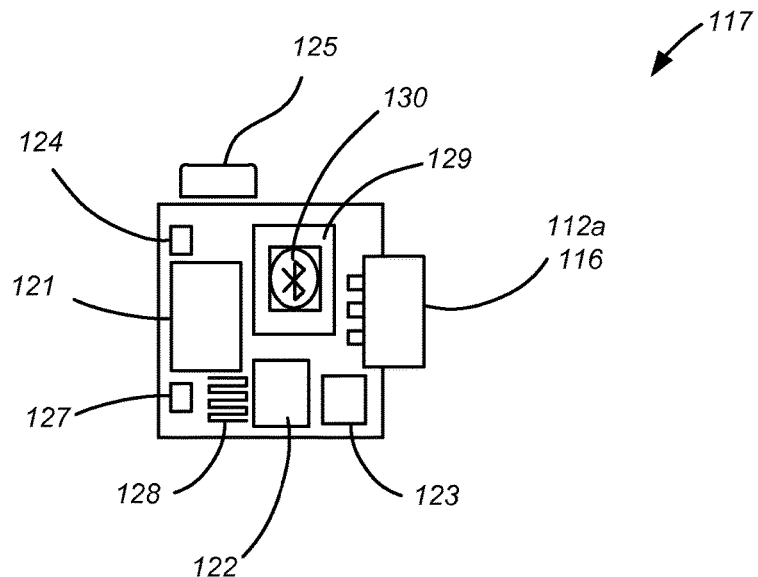
FIG. 3B is a plan view of an example configuration for a printed circuit assembly of an embodiment apparatus and/or system.

In some embodiments of the system as illustrated in FIG. 3A or 3B, the digital processing device 113 comprises a printed circuit assembly (PCA) 117 (see also FIG. 3C) comprising an electronic interface connection 112a, a flow sensor analyzer 123, an energy control circuit 121, a mounting interface 115, and a memory 122 for storing the computer program for providing instruction to the digital processing device 113.

In some embodiments of the system, the printed circuit assembly 117 further comprises: a microprocessor 129, an electronic communication system 130 for communicating with other electronic devices, and an antenna 128. In some embodiments of the system, the microprocessor is configured to control the communication and program input/output functions of the system. In some embodiments, the communication platform for communicating with other electronic devices comprises: wireless communication links such as Bluetooth 130 and Infrared (IR), (not shown), wired communication links such as micro-USB 144 (among others), and combinations thereof, wherein the other electronic devices comprise: computers, mobile devices, computer networks, and electronic storage data devices. Additionally, in some embodiments, the apparatus is configured with software for a variety of intranet, internet/web applications.

Figure 3C:
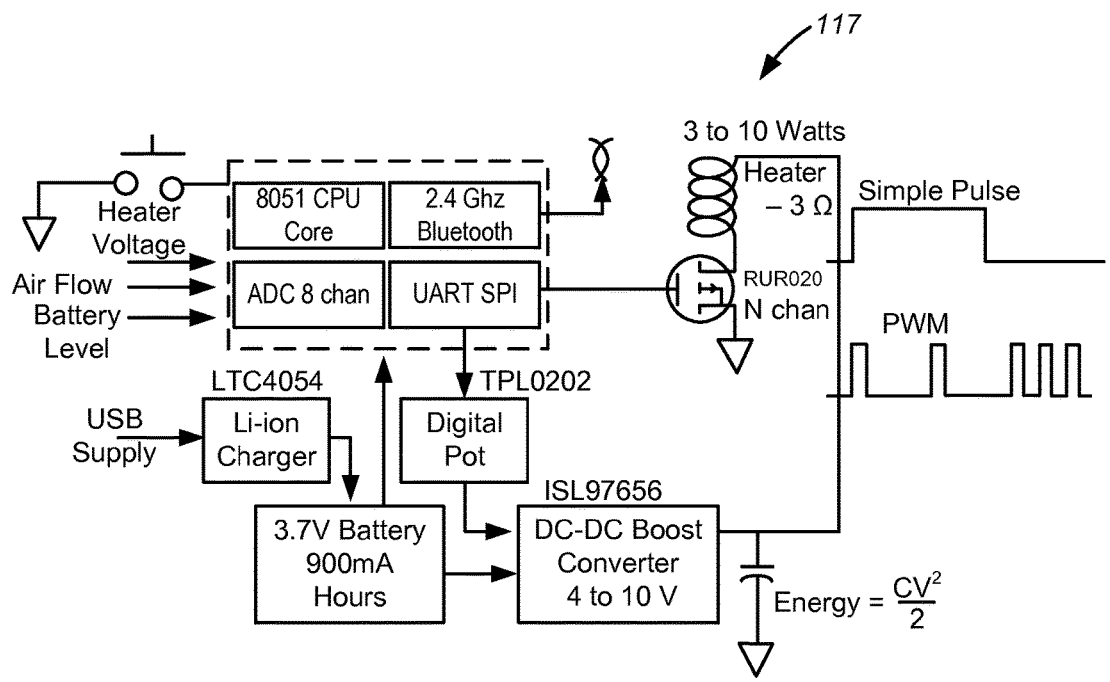
FIG. 3C is a wiring schematic for the printed circuit assembly illustrating a variable voltage block diagram for a simple pulse or pulse width modulation output of an embodiment apparatus and/or system.

In some embodiments of the system, the energy control circuit 121 is configured to produce either a simple pulse or a Pulse Width Modulation output signal as illustrated in FIG. 3C configured to individually meter electrical power delivered to the first heater 185, the second heater 180, or both; control a first temperature of the first heater 185, a second temperature of the second heater 180, or both; and control a first rate of production of the first vapor, a second rate of production of the second vapor, or a third rate of production of the third vapor. The first heater may comprise a first heater coil configured to heat the first liquid substance in the first wick to vaporize the first liquid substance. The second heater may comprise a second heater coil configured to heat the second liquid substance in the second wick to vaporize the second liquid substance. The first heater may comprise a first foil heater circuit configured to heat the first liquid substance in the first wick (alternatively called a first wicking surface) to vaporize the first liquid substance. The second heater may comprise a second foil heater circuit configured to heat the second liquid substance in the second wick (alternatively called a second wicking surface) to vaporize the second liquid substance.

In some embodiments, the system is configured to change the third vapor for any given puff, according to the nicotine management plan.

In some embodiments, a vaporization chamber volume of the vaporization chamber corresponds to a typical puff volume. In some embodiments the vaporization chamber volume is greater than the puff volume. In some embodiments, a typical puff volume is about 15 ml to about 175 ml, about 20 ml to about 150 ml, about 15 ml to about 100 ml, about 15 ml to about 75 ml, about 20 ml to about 75 ml, about 25 ml to about 50 ml, about 25 ml, about 35 ml, about 40 ml, about 45 ml, about 50 ml, about 60 ml, 15 ml to 175 ml, 20 ml to 150 ml, 15 ml to 100 ml, 15 ml to 75 ml, 20 ml to 75 ml, 25 ml to 50 ml, 25 ml, 35 ml, 40 ml, 45 ml, 50 ml, or 60 ml. In some embodiments, the user's own typical puff volume is determined by system, or the user's own typical puff volume is provided to the system and used to adjust the nicotine in the third vapor (as amount or percentage) over time according to the management plan. In some embodiments, the system and/or apparatus is configured to provide an amount of nicotine in the third vapor (i.e. in a given 100 ml volume of the third vapor), wherein the amount of nicotine in 100 ml of third vapor is from about 0.0 mcg to about 200.0 mcg, from 0.0 mcg to 200 mcg, about 0.0 mcg to about 100.0 mcg, from 0.0 mcg to 100 mcg, from about 0.1 mcg to about 199.9 mcg, from 0.1 mcg to 199.9 mcg, from about 0.1 mcg to about 99.9 mcg, from 0.1 mcg to 99.9 mcg, from about 0.5 mcg to about 99.5 mcg, from 0.5 mcg to 99.5 mcg, from about 1.0 mcg to about 99.0 mcg, from 1.0 mcg to 99.0 mcg, from about 5.0 mcg to about 95.0 mcg, from 5.0 mcg to 95.0 mcg, from about 0.5 mcg to about 90.0 mcg, from 0.5 mcg to 90.0 mcg, from about 0.0 mcg to about 90.0 mcg, from 0.0 ml to 90.0 ml, from about 0.0 mcg to about 80.0 mcg, from about 0.5 mcg to about 80.0 mcg, from 0.5 mcg to 80.0 mcg, from 0.0 mcg to 80.0 mcg, from about 0.0 mcg to about 70.0 mcg, from 0.0 mcg to 70.0 mcg, from about 0.0 mcg to about 60.0 mcg, from 0.0 ml to 60.0 ml, from about 1.0 mcg to about 60.0 mcg, from 1.0 ml to 60.0 ml, from about 0.5 mcg to about 60.0 mcg, from 0.5 mcg to 60.0 mcg, from about 0.0 mcg to about 50.0 mcg, from 0.0 mcg to 50.0 mcg, from about 0.5 mcg to about 50.0 mcg, from 0.5 mcg to 50.0 mcg, from about 0.0 mcg to about 20 mcg, or from 0.0 mcg to 20.0 mcg. In some embodiments, the system and/or apparatus is configured to adjust the amount of nicotine in the third vapor (per 100 ml volume of the third vapor) in increments of 0.01 mcg, 0.05 mcg, 0.1 mcg, 0.15 mcg, 0.2 mcg, 0.25 mcg, 0.3 mcg, 0.35 mcg, 0.4 mcg, 0.5 mcg, 0.6 mcg, 0.7 mcg, 0.75 mcg, 0.8 mcg, 0.9 mcg, 1.0 mcg, 2.0 mcg, 3.0 mcg, 4.0 mcg, 5.0 mcg, 6.0 mcg, 7.0 mcg, 8.0 mcg, 9.0 mcg, 10.0 mcg, 11.0 mcg, 12.0 mcg, 13.0 mcg, 14.0 mcg, 15.0 mcg, 16.0 mcg, 17.0 mcg, 18.0 mcg, 19.0 mcg, 20.0 mcg, 25.0 mcg, 30.0 mcg, 40.0 mcg, 50.0 mcg, about 0.01 mcg, about 0.05 mcg, about 0.1 mcg, about 0.15 mcg, about 0.2 mcg, about 0.25 mcg, about 0.3 mcg, about 0.35 mcg, about 0.4 mcg, about 0.5 mcg, about 0.6 mcg, about 0.7 mcg, about 0.75 mcg, about 0.8 mcg, about 0.9 mcg, about 1.0 mcg, about 2.0 mcg, about 3.0 mcg, about 4.0 mcg, about 5.0 mcg, about 6.0 mcg, about 7.0 mcg, about 8.0 mcg, about 9.0 mcg, about 10.0 mcg, about 11.0 mcg, about 12.0 mcg, about 13.0 mcg, about 14.0 mcg, about 15.0 mcg, about 16.0 mcg, about 17.0 mcg, about 18.0 mcg, about 19.0 mcg, about 20.0 mcg, about 25.0 mcg, about 30.0 mcg, about 40.0 mcg, or about 50.0 mcg. In some embodiments, the system and/or apparatus is configured to provide an amount of the nicotine in the third vapor based on a typical puff volume (as defined above) or based on the user's individual puff volume as measured by the apparatus or as provided to the system, the amount of nicotine for example being from about 0.0 mcg to about 250.0 mcg, from 0.0 mcg to 250.0 mcg, about 0.0 mcg to about 100.0 mcg, from 0.0 mcg to 100.0 mcg, from about 0.5 mcg to about 100.0 mcg, from 0.5 mcg to 100.0 mcg, from about 0.5 mcg to about 90.0 mcg, from 0.5 mcg to 90.0 mcg, from about 0.0 mcg to about 75.0 mcg, from 0.0 mcg to 75.0 mcg, 0.01 mcg, 0.05 mcg, 0.1 mcg, 0.15 mcg, 0.2 mcg, 0.25 mcg, 0.3 mcg, 0.35 mcg, 0.4 mcg, 0.5 mcg, 0.6 mcg, 0.7 mcg, 0.75 mcg, 0.8 mcg, 0.9 mcg, 1.0 mcg, 2.0 mcg, 3.0 mcg, 4.0 mcg, 5.0 mcg, 6.0 mcg, 7.0 mcg, 8.0 mcg, 9.0 mcg, 10.0 mcg, 11.0 mcg, 12.0 mcg, 13.0 mcg, 14.0 mcg, 15.0 mcg, 16.0 mcg, 17.0 mcg, 18.0 mcg, 19.0 mcg, 20.0 mcg, 21.0 mcg, 22.0 mcg, 23.0 mcg, 24.0 mcg, 25.0 mcg, 26.0 mcg, 27.0 mcg, 28.0 mcg, 29.0 mcg, 30.0 mcg, 31.0 mcg, 32.0 mcg, 33.0 mcg, 34.0 mcg, 35.0 mcg, 36.0 mcg, 37.0 mcg, 38.0 mcg, 39.0 mcg, 40.0 mcg, 41.0 mcg, 42.0 mcg, 43.0 mcg, 44.0 mcg, 45.0 mcg, 46.0 mcg, 47.0 mcg, 48.0 mcg, 49.0 mcg, 50.0 mcg, 51.0 mcg, 52.0 mcg, 53.0 mcg, 54.0 mcg, 55.0 mcg, 56.0 mcg, 57.0 mcg, 58.0 mcg, 59.0 mcg, 60.0 mcg, 61.0 mcg, 62.0 mcg, 63.0 mcg, 64.0 mcg, 65.0 mcg, 66.0 mcg, 67.0 mcg, 68.0 mcg, 69.0 mcg, 70.0 mcg, 71.0 mcg, 72.0 mcg, 73.0 mcg, 74.0 mcg, 75.0 mcg, 76.0 mcg, 77.0 mcg, 78.0 mcg, 79.0 mcg, 80.0 mcg, 81.0 mcg, 82.0 mcg, 83.0 mcg, 84.0 mcg, 85.0 mcg, 86.0 mcg, 87.0 mcg, 88.0 mcg, 89.0 mcg, 90.0 mcg, 91.0 mcg, 92.0 mcg, 93.0 mcg, 94.0 mcg, 95.0 mcg, 96.0 mcg, 97.0 mcg, 98.0 mcg, 99.0 mcg, 100.0 mcg, 0 mcg to 100 mcg in increments of 0.01 mcg, 0 mcg to 100 mcg in increments of 0.1 mcg, 0 mcg to 100 mcg in increments of 0.5 mcg, 0 mcg to 100 mcg in increments of 1 mcg, 0.5 mcg to 100 mcg in increments of 0.5-5 mcg, 0.0 mcg to 100 mcg in increments of 0.5 mcg to 5 mcg, 0.0 mcg to 150 mcg in increments of 0.5 mcg to 5 mcg, 0.0 mcg to 100 mcg in increments of 0.5 mcg to 25 mcg, about 0.01 mcg, about 0.05 mcg, about 0.1 mcg, about 0.15 mcg, about 0.2 mcg, about 0.25 mcg, about 0.3 mcg, about 0.35 mcg, about 0.4 mcg, about 0.5 mcg, about 0.6 mcg, about 0.7 mcg, about 0.75 mcg, about 0.8 mcg, about 0.9 mcg, about 1.0 mcg, about 2.0 mcg, about 3.0 mcg, about 4.0 mcg, about 5.0 mcg, about 6.0 mcg, about 7.0 mcg, about 8.0 mcg, about 9.0 mcg, about 10.0 mcg, about 11.0 mcg, about 12.0 mcg, about 13.0 mcg, about 14.0 mcg, about 15.0 mcg, about 16.0 mcg, about 17.0 mcg, about 18.0 mcg, about 19.0 mcg, about 20.0 mcg, about 21.0 mcg, about 22.0 mcg, about 23.0 mcg, about 24.0 mcg, about 25.0 mcg, about 26.0 mcg, about 27.0 mcg, about 28.0 mcg, about 29.0 mcg, about 30.0 mcg, about 31.0 mcg, about 32.0 mcg, about 33.0 mcg, about 34.0 mcg, about 35.0 mcg, about 36.0 mcg, about 37.0 mcg, about 38.0 mcg, about 39.0 mcg, about 40.0 mcg, about 41.0 mcg, about 42.0 mcg, about 43.0 mcg, about 44.0 mcg, about 45.0 mcg, about 46.0 mcg, about 47.0 mcg, about 48.0 mcg, about 49.0 mcg, about 50.0 mcg, about 51.0 mcg, about 52.0 mcg, about 53.0 mcg, about 54.0 mcg, about 55.0 mcg, about 56.0 mcg, about 57.0 mcg, about 58.0 mcg, about 59.0 mcg, about 60.0 mcg, about 61.0 mcg, about 62.0 mcg, about 63.0 mcg, about 64.0 mcg, about 65.0 mcg, about 66.0 mcg, about 67.0 mcg, about 68.0 mcg, about 69.0 mcg, about 70.0 mcg, about 71.0 mcg, about 72.0 mcg, about 73.0 mcg, about 74.0 mcg, about 75.0 mcg, about 76.0 mcg, about 77.0 mcg, about 78.0 mcg, about 79.0 mcg, about 80.0 mcg, about 81.0 mcg, about 82.0 mcg, about 83.0 mcg, about 84.0 mcg, about 85.0 mcg, about 86.0 mcg, about 87.0 mcg, about 88.0 mcg, about 89.0 mcg, about 90.0 mcg, about 91.0 mcg, about 92.0 mcg, about 93.0 mcg, about 94.0 mcg, about 95.0 mcg, about 96.0 mcg, about 97.0 mcg, about 98.0 mcg, about 99.0 mcg, about 100.0 mcg, about 0 mcg to about 100 mcg in increments of 0.01 mcg, about 0 mcg to about 100 mcg in increments of 0.1 mcg, about 0 mcg to about 100 mcg in increments of 0.5 mcg, about 0 mcg to about 100 mcg in increments of 1 mcg, about 0.5 mcg to about 100 mcg in increments of 0.5-5 mcg, about 0.0 mcg to about 100 mcg in increments of 0.5 mcg to 5 mcg, about 0.0 mcg to about 150 mcg in increments of 0.5 mcg to 5 mcg, or about 0.0 mcg to about 100 mcg in increments of 0.5 mcg to 25 mcg. In some embodiments, the system and/or apparatus is configured to modulate or adjust the amount of nicotine in the third vapor in increments of 1.0 mcg, 5.0 mcg, 10.0 mcg, 20.0 mcg, 25.0 mcg, 30.0 mcg, 40.0 mcg, 50.0 mcg, 75.0 mcg, 100.0 mcg, 150.0 mcg, 200.0 mcg, 250.0 mcg, about 1.0 mcg, about 5.0 mcg, about 10.0 mcg, about 20.0 mcg, about 25.0 mcg, about 30.0 mcg, about 40.0 mcg, about 50.0 mcg, about 75.0 mcg, about 100.0 mcg, about 150.0 mcg, about 200.0 mcg, about 250.0 mcg, less than 250.0 mcg, less than 200.0 mcg, less than 150.0 mcg, less than 100.0 mcg, less than 75.0 mcg, less than 50.0 mcg, less than 40.0 mcg, less than 30.0 mcg, less than 25.0 mcg, less than 20.0 mcg, less than 10.0 mcg, less than 5.0 mcg, greater than about 5.0 mcg, greater than about 10.0 mcg, greater than about 20.0 mcg, greater than about 25.0 mcg, greater than about 30.0 mcg, greater than about 40.0 mcg, greater than about 50.0 mcg, greater than about 75.0 mcg, greater than about 100.0 mcg, greater than about 150.0 mcg, greater than about 200.0 mcg and greater than about 250.0 mcg. In some embodiments, the system and/or apparatus is configured to modulate the percentage of nicotine in the third vapor from about 0% to about 100%, from 0% to 100%, from about 0.01% to about 99.99%, from 0.01% to 99.99%, from about 0.05% to about 99.95%, from about 0.1% to about 99.9%, from 0.1% to about 99.9%, from about 0.5% to about 99.5%, from 0.5% to 99.5%, from about 0% to about 90%, from 0% to 90%, from about 0% to about 80%, from 0% to 80%, from about 0% to about 75%, from 0% to 75%, from about 0% to about 10%, from 0% to 10%, from about 0.01% to about 10%, from 0.01% to 10%, from about 0% to about 25%, from 0% to 25%, from about 0.01% to about 25%, and/or from 0.01% to 25%. In some embodiments, the system and/or apparatus is configured to change the percentage of nicotine in the third vapor in increments of 100%, 50%, 40%, 35%, 30%, 25%, 20%, 15%, 10%, 9%, 8%, 7%, 7.5%, 6%, 5%, 4%, 3%, 2%, 1%, 0.5%, 0.1%, 0.05%, 0.01%, about 100%, about 50%, about 40%, about 35%, about 30%, about 25%, about 20%, about 15%, about 10%, about 9%, about 8%, about 7%, about 7.5%, about 6%, about 5%, about 4%, about 3%, about 2%, about 5%, about 1%, about 0.5%, about 0.1%, about 0.05%, about 0.01%, less than 100%, less than 50%, less than 20%, less than 10%, less than 5%, less than 1%, less than 0.5%, less than 0.1%, less than 0.05%, less than 0.01%, greater than about 100%, greater than about 50%, greater than about 20%, greater than about 10%, greater than about 5%, greater than about 1%, greater than about 0.5%, greater than about 0.1%, greater than about 0.05%, and/or greater than about 0.01%.

Figure 2A:
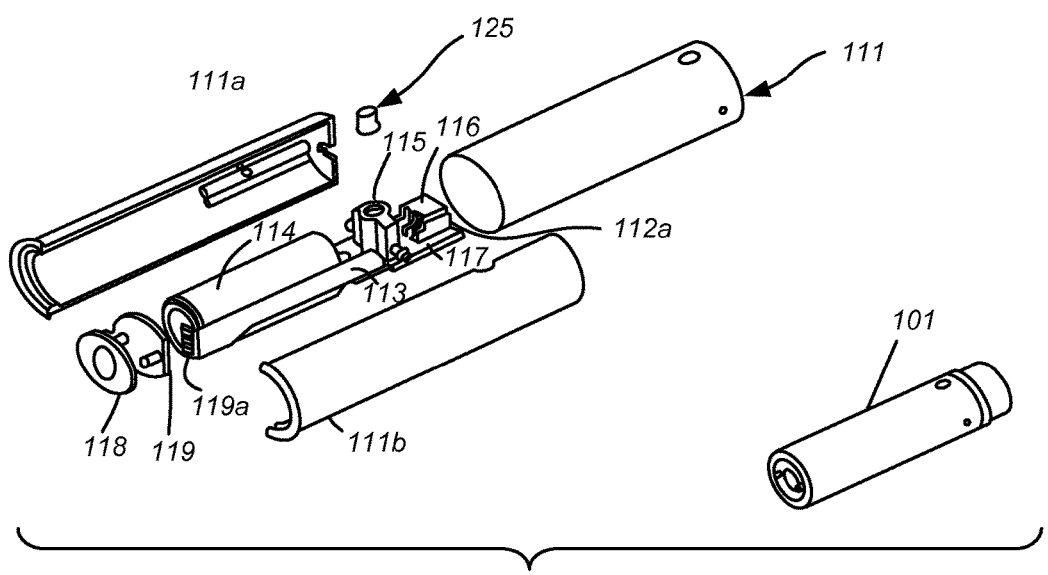
FIG. 2A is an illustrative exploded sub-assembly arrangement of a durable housing of an embodiment apparatus and/or system.
Figure 2B:
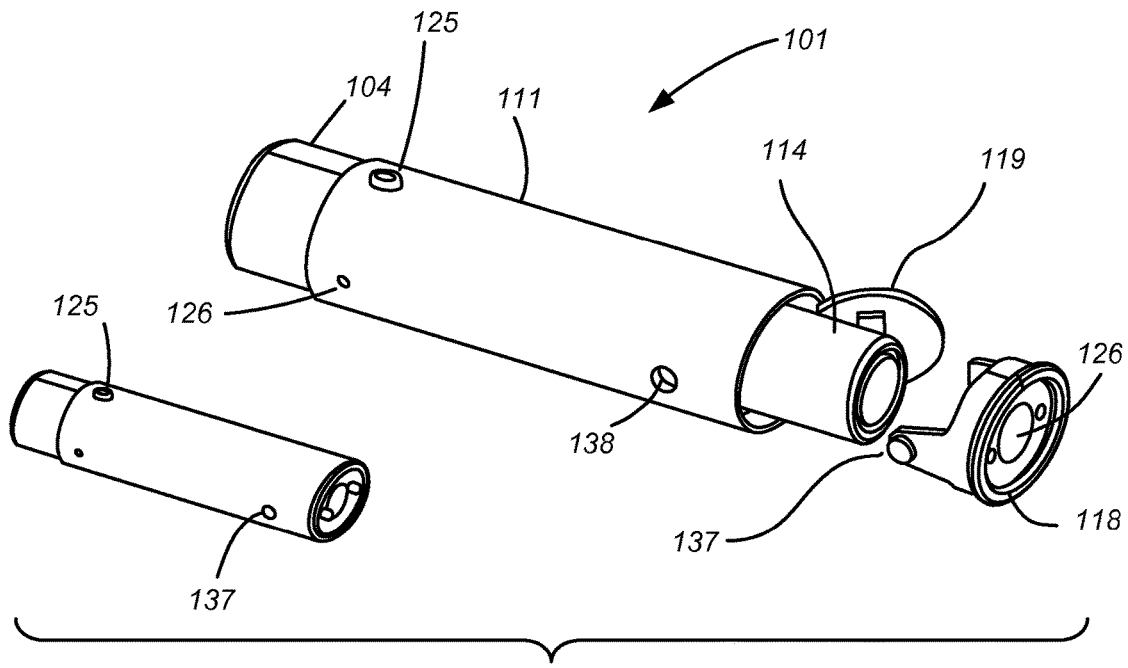
FIG. 2B is an illustrative partially exploded sub-assembly arrangement of a durable housing of an embodiment apparatus and/or system, showing a removable end cap, retractable charging contact circuit and removable battery.

In some embodiments of the system the durable housing component 101 may have alternate internal configurations, as illustrated in FIGS. 1B/2B,1C and 3A. FIG. 1B is an illustrative exploded sub-assembly arrangement of FIG. 1A. FIG. 2B is an illustrative partially exploded sub-assembly arrangement of a durable housing of an embodiment apparatus and/or system, showing a removable end cap, retractable charging contact circuit and removable battery. As shown in FIGS. 1B and 2B, the durable housing comprises an outer housing (101) and an inner casing 111 to provided added protection of the battery/power source 114. Alternatively, the inner casing may be of a one-piece (111) or multi-piece (111a/111b) construction, as illustrated in FIG. 2A. The programmable electronic controller, also known as a programmable electronic controller 113 can be comprise a series of assembled components such as a flex circuit connecting the battery 114, LED indicators 126 and charging circuit 119 to the remaining electronic components, or it may comprise a single printed circuit assembly (PCA) 117 with individual mounting features 115 for select features such as LED indicators 126 or override buttons 125 and Molex connectors 116 to accommodate interface connections 112.

As noted in any one of FIG. 1B, 1C, 2A, 3A or 3B, in some embodiments of the system, the printed circuit assembly 117 comprises: an electronic interface connection 112 (112a+112b), a flow sensor analyzer 123, an energy control circuit 121, and a memory 122 for storing a programmable logic. In some embodiments, connectors such as Molex connectors 116 are employed to provide interface connections between components.

In some embodiments of the system, the digital processing device (DPD), 113 or the PCA 117, or the combined DPD with a PCA, further comprises a microprocessor 129 configured to control communication platforms and input/output program functions for the apparatus; an electronic communication platform 130 for communicating with other electronic devices and an antenna 128.

In some embodiments, the programmable electronic controller or DPD is further configured with an energy control circuit 121 configured to produce either a simple pulse or a Pulse Width Modulation (PWM) output signal, as illustrated in FIG. 3C to individually meter the electrical power delivered to the two or more heating elements 180, 185 (alternatively called heater(s), herein) in the multi-chamber release mechanism, thus controlling the heating element temperature and the rate of vapor production, wherein the simple pulse or PWM output signal is capable of controlling the amount of nicotine dispensed into a first vapor for any given puff, over a period of time. As noted elsewhere herein, while the amount of nicotine delivered to a user is an ultimate goal, there are many options for how to control this nicotine amount. The first heater may comprise a first heater coil configured to heat the first liquid substance in the first wick to vaporize the first liquid substance. The second heater may comprise a second heater coil configured to heat the second liquid substance in the second wick to vaporize the second liquid substance. The first heater may comprise a first foil heater circuit configured to heat the first liquid substance in the first wick (alternatively called a first wicking surface) to vaporize the first liquid substance. The second heater may comprise a second foil heater circuit configured to heat the second liquid substance in the second wick (alternatively called a second wicking surface) to vaporize the second liquid substance. For example the system and/or apparatus, using the controller or DPD is able to modulate an amount of nicotine in the third vapor according to the nicotine management plan, an amount of nicotine in the first vapor according to the nicotine management plan, an amount of the first liquid substance in the third vapor according to the nicotine management plan, an amount of the first liquid substance in the first vapor according to the nicotine management plan, an amount of the second liquid substance in the third vapor according to the nicotine management plan, an amount of the second liquid substance in the second vapor according to the nicotine management plan, a percentage of the first liquid substance in the third vapor according to the nicotine management plan, a percentage of the second liquid substance in the third vapor according to the nicotine management plan, a percentage of nicotine in the third vapor according to the nicotine management plan, a ratio of the first liquid substance to the second substance in the third vapor according to the nicotine management plan, or a combination thereof, as disclosed elsewhere herein. Variables of the simple pulse or PWM output signal that can be used in these modulations include pulse duration, pulse frequency, number of pulses in a given duration, pulse voltage, temperature of the heater for example the temperature of the heater coil or of the foil heater circuit within limits so as to remain within a temperature range appropriate for the vaporization of the first liquid substance and/or the second liquid substance. The temperature of the heater may be limited and so as to not to degrade or burn the first liquid substance and/or the second liquid substance. The dose (amount of nicotine in the third vapor per typical puff or per user's own actual puff or per 100 ml of third vapor) of nicotine from the apparatus is controlled by a regulated and constant voltage circuit that supplies constant power to each of the heater(s). The duration of on-time and frequency of on-time of the heater(s) is supplied from a pre-determined sequence (according to the management plan) to enable the heater(s) to reach and maintain a temperature that provides vapor. The dose of nicotine in the first vapor is proportional to the temperature of the heater coil (or foil heater circuit) and length of time the coil (or foil heater circuit) is at or above the vapor-generating temperature which is based on the constituents and proportion of constituents of the first liquid substance being heated. Similarly, the amount of second vapor is proportional to the temperature of the heater coil (or foil heater circuit) and length of time the coil (or foil heater circuit) is at or above the vapor-generating temperature of the second liquid substance. Coil temperature (or foil heater circuit temperature) is proportional to the duration as well as frequency that power is supplied. The dose of nicotine in a puff is determined by the total time the vaporizer coil (or foil heater circuit) is at or above the vapor-generating temperature based on a known value that has been correlated to 1) know nicotine dose from experiments and/or 2) amount of nicotine-containing liquid being consumed. Within a puff event, both the nicotine vaporizer (first vapor) and flavor-only vaporizer (second vapor) can be energized. For example, in the case of mixing during a puff event, the first vapor may energized for a period of time proportional to a known amount dose of nicotine for a given set of conditions and the second vaporizer is energized for the remainder of the puff event. In the case of optimal power management, it is possible to utilize the "inter-puff" dosing scheme: the first vaporizer may be energized only for a set number of puff events that correspond to the dose program for a given "smoking session". Once the allotted total dose has been reached, then the second vapor only is energized for the remaining smoking session. In this method only one vaporize is energized per puff event which eliminates both first and second vapor units being energized for a single puff event. In addition, the power circuit may have a current monitor as a proxy for heater temperature (heater temperature is related to the amount of current supplied at a constant voltage). In some embodiments of the system, the durable housing 101 comprises at least one of: a power source 114; a connection interface 112/112a configured to connect the durable housing 102 to the vaporizer housing 102; an LED 126; a battery contact 119a; and a charging interface circuit 119 as illustrated in FIGS. 2A and 2B.

In some embodiments, the system is configured to change the percentage of nicotine in the third vapor from about 0% to about 100%, from 0% to 100%, from about 0.01% to about 99.99%, from 0.01% to 99.99%, from about 0.05% to about 99.95%, from about 0.1% to about 99.9%, from 0.1% to 99.9%, from about 0.5% to about 99.5%, from 0.5% to 99.5%, from about 0% to about 90%, from 0% to 90%, from about 0% to about 80%, from 0% to 80%, from about 0% to about 75%, from 0% to 75%, from about 0% to about 10%, from 0% to 10%, from about 0.01% to about 10%, from 0.01% to 10%, from about 0% to about 25%, from 0% to 25%, from about 0.01% to about 25%, and/or from 0.01% to 25%.

In some embodiments, the percentage of nicotine in the third vapor can be adjusted in increments of 100%, 50%, 40%, 35%, 30%, 25%, 20%, 15%, 10%, 9%, 8%, 7%, 7.5%, 6%, 5%, 4%, 3%, 2%, 1%, 0.5%, 0.1%, 0.05%, 0.01%, about 100%, about 50%, about 40%, about 35%, about 30%, about 25%, about 20%, about 15%, about 10%, about 9%, about 8%, about 7%, about 7.5%, about 6%, about 5%, about 4%, about 3%, about 2%, about 5%, about 1%, about 0.5%, about 0.1%, about 0.05%, about 0.01%, less than 100%, less than 50%, less than 20%, less than 10%, less than 5%, less than 1%, less than 0.5%, less than 0.1%, less than 0.05%, less than 0.01%, greater than about 100%, greater than about 50%, greater than about 20%, greater than about 10%, greater than about 5%, greater than about 1%, greater than about 0.5%, greater than about 0.1%, greater than about 0.05%, and greater than about 0.01%.

In some embodiments of the system, the digital processing device 113/117 comprises on-board memory 122 configured to: store an operating system or computer program configured to perform the instructions; and record a first set of data and a second set of data.

In some embodiments, the first set of data comprises vaporization characteristics comprising one or more of: a first power reading of power delivered to the first heater, a second power reading of power delivered to the second heater, a first duration of energization delivered to the first heater, a second duration of energization delivered to the second heater, and a simple pulse signal profile or a pulse width modulation signal profile.

In some embodiments of the system, the flow sensor analyzer 123 is configured to detect and record a second set of data comprising one or more of: a date of each user puff; a time of each user puff; a duration of each user puff; an amount of nicotine released to a user; a puff flow; a puff intensity; and an airflow rate within the vapor release mechanism 290.

In some embodiments of the system, the digital processing device 113/117 comprises on-board memory 122 and wherein the second set of data is stored in the on-board memory.

In some embodiments of the system, the vaporizer housing 102 is configured to receive an attachable mouthpiece 103. In some embodiments, the mouthpiece 103 is replaceable. In some embodiments, the vaporizer housing 102 is replaceable.

In some embodiments of the system, the digital processing device 113/117 is configured to execute the instructions defined by the computer program based on the nicotine management plan wherein the vapor release mechanism 290 produces the third vapor having a consistent characteristic regardless of the ratio of the first vapor to the second vapor.

Figure 8A:
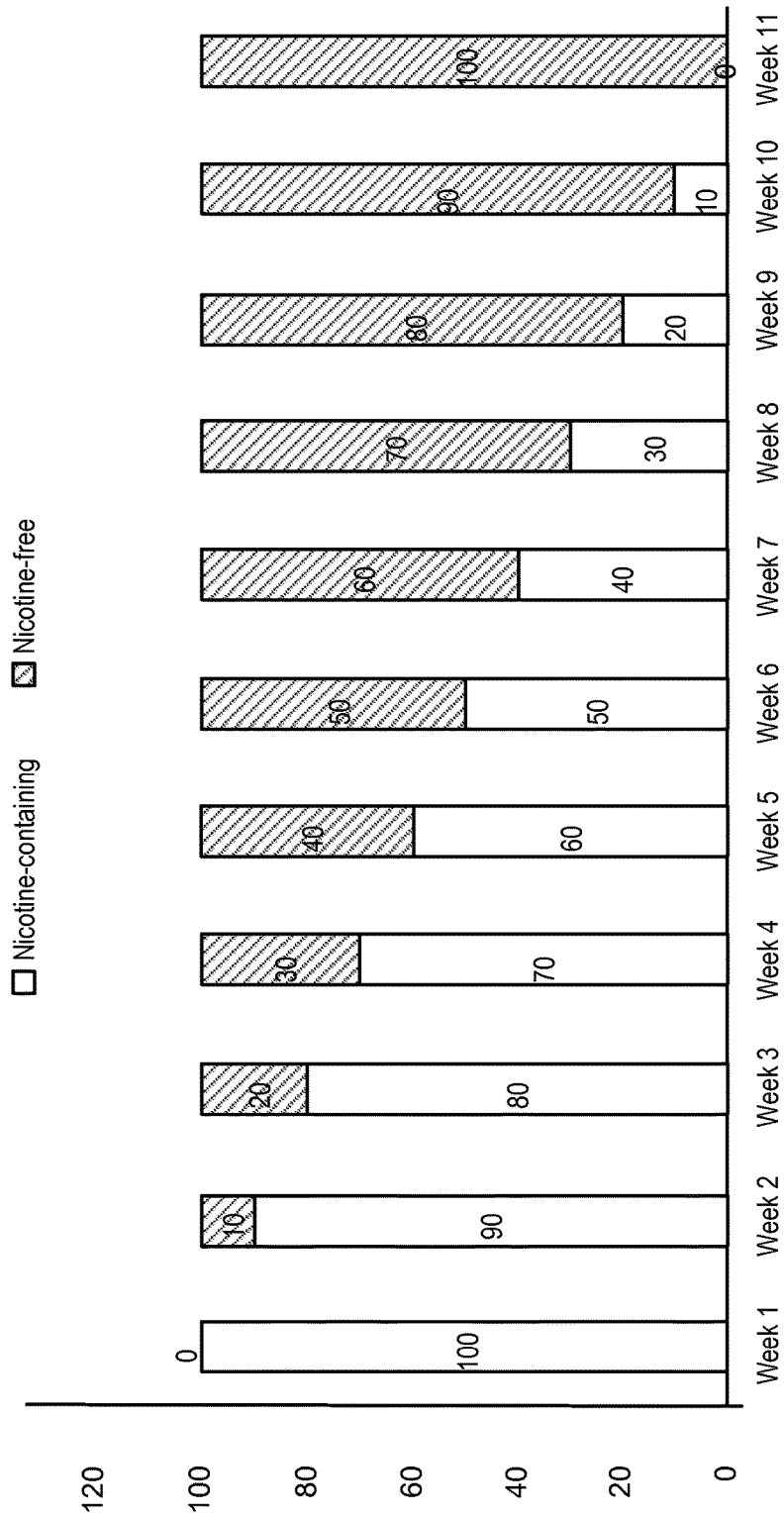
FIG. 8A is an illustrative example of nicotine modulation that can occur with an embodiment nicotine management plan over a specified duration period of an embodiment system.
Figure 8B:
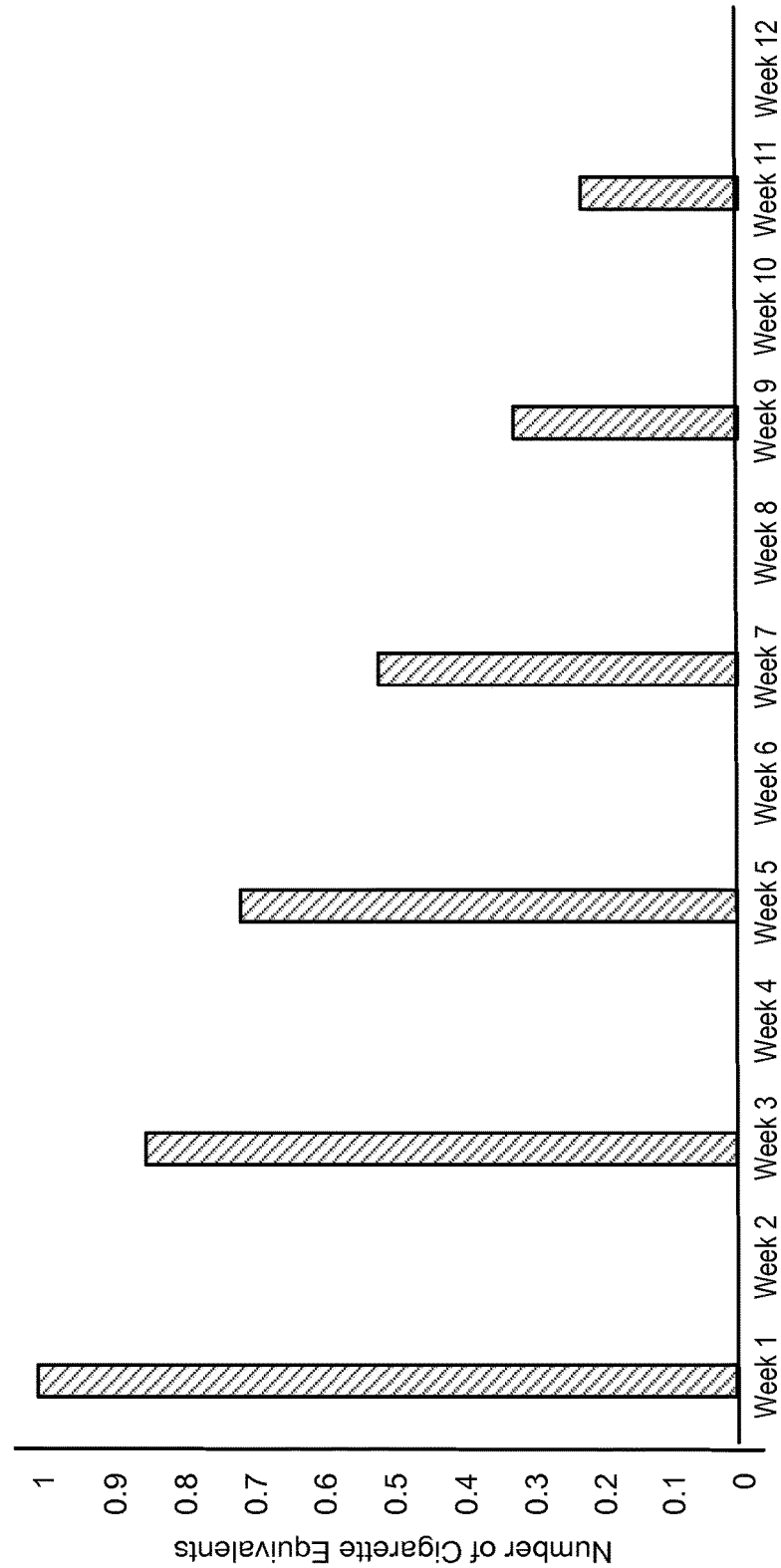
FIG. 8B is an illustrative of a sample nicotine equivalence delivered to a user of the system with an embodiment nicotine management plan over a specified duration period.

In some embodiments of the system, the nicotine management plan gradually diminishes the amount or percentage of nicotine in the third vapor over a specified period of time. In some embodiments, the characteristic comprises; measurable amounts of nicotine in the third vapor or measurable percentage of nicotine in the third vapor generated by the electronic vaporizing apparatus; and/or measurable amounts of flavorant in the third vapor or measurable percentage of flavorant in the third vapor generated by the electronic vaporizing apparatus. FIGS. 8A and 8B represent examples of the modulating effect of an illustrative management plan utilized with the system and apparatus.

In some embodiments of the system and/or apparatus, the vapor characteristic produced with each puff comprise: vapor intensity (measurable as vapor flow rate), vapor volume, vapor density (measured by spectrophotometry methods known to one of skill in the art), vapor flavor, and/or oral sensation, wherein the characteristic is consistent irrespective of nicotine levels. In some embodiments of the system and/or apparatus, the vapor characteristic produced with each puff comprises vapor intensity (measurable as vapor flow rate). In some embodiments of the system and/or apparatus, the vapor characteristic produced with each puff comprises vapor volume. In some embodiments of the system and/or apparatus, the vapor characteristic produced with each puff comprises vapor density (measured by spectrophotometry methods known to one of skill in the art). In some embodiments of the system and/or apparatus, the vapor characteristic produced with each puff comprises vapor flavor, and/or oral sensation.

In some embodiments, the system comprises an override feature 125, configurable to override the digital processing device 113/117 to modify the amount or percentage of the nicotine dispensed. In some embodiments, the override feature 125 is manual. In some embodiments, the override feature is automatic.

Figure 11:
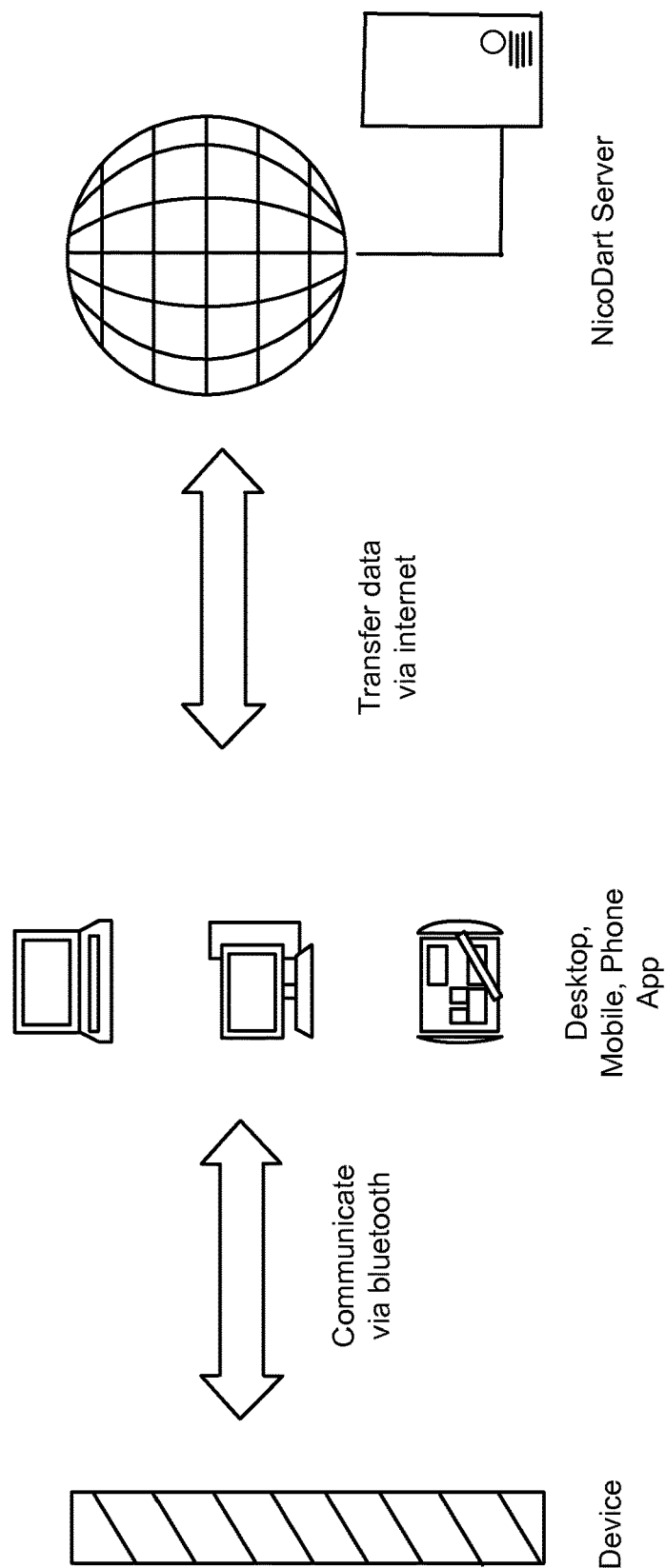
FIG. 11 is an illustrative example of the data transfer scheme capability for the system, using the apparatus, management plan, software, associated applications and hardware of an embodiment apparatus and/or system.

In some embodiments of the system, the microprocessor 129 is configured to control communication systems 130 and input/output program functions for the apparatus. In some embodiments, the electronic communication system 130 for communicating with one or more other electronic device comprises: a wireless communication link 128; and a wired communication link 144, wherein the other electronic device comprises: a computer; a mobile device; a computer network; and an electronic storage data device, as illustrated in FIG. 11.

Figure 6A:
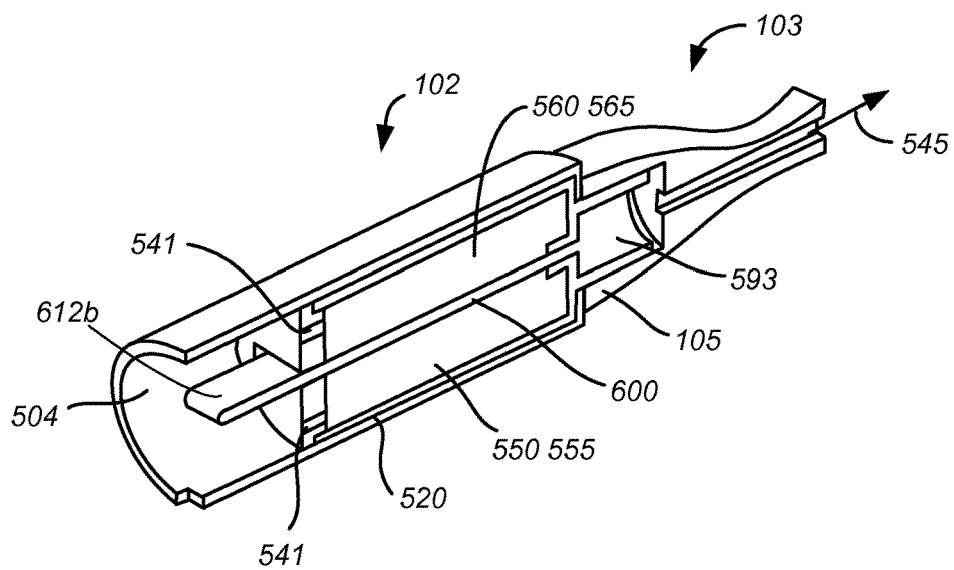
FIG. 6A is an illustrative cut-away partial section ISO view of a configuration of an exemplary dual cartridge chamber, parallel arrangement reservoir, vaporization housing and mouthpiece assembly and a digital vaporizing chip with a foil heater circuit of an embodiment apparatus and/or system.

In some embodiments of the system 100, the first cartridge chamber 260 and the second chamber 250 are in series arrangement as illustrated in FIG. 4B, are in parallel arrangement as illustrated in FIG. 6A, and/or comprise a central vapor flow path 145 through a vaporization chamber 190 common to the first cartridge 160 and the second cartridge 150 as illustrated in FIG. 4A.

FIG. 4A is an illustrative general simplified schematic view of an exemplary dual cartridge chamber, series arrangement reservoir, vaporization housing 112b and mouthpiece 103 of an embodiment apparatus and/or system. As shown in FIG. 4A, the cartridge chambers for the vaporizer housing 102 illustrate a dual cartridge, series arrangement with a first cartridge chamber 150 comprising a first liquid substance comprising nicotine and a first cartridge chamber 160 comprising a first liquid non-nicotine substance, a first wick 170, a second wick 175 and a first heater 180, a second heater 185 aligned in a series arrangement, with a vaporization chamber 190 arranged therebetween and in fluid communication with an airflow inlet 140 and vapor flow outlet path 145 to a mouthpiece 103. The apparatus also illustrates an electrical connector 112b by which electrical current may be selectively transmitted to the individual heaters to provide precise control over the vaporization temperature applied to each wick. In this arrangement, the chamber can be circumferential and stacked on top of each other. The order of the chambers does not matter. The nicotine chamber 150 could be on top or bottom, as could the non-nicotine chamber 160. An illustrative example of such an arrangement is shown in FIG. 4B. The first heater may comprise a first heater coil configured to heat the first liquid substance in the first wick to vaporize the first liquid substance. The second heater may comprise a second heater coil configured to heat the second liquid substance in the second wick to vaporize the second liquid substance. The first heater may comprise a first foil heater circuit configured to heat the first liquid substance in the first wick (alternatively called a first wicking surface) to vaporize the first liquid substance. The second heater may comprise a second foil heater circuit configured to heat the second liquid substance in the second wick (alternatively called a second wicking surface) to vaporize the second liquid substance.

In some embodiments, the multi-chamber vapor release mechanism is configured to independently or simultaneously provide the dispensation and vaporization of variable amounts of the nicotine and a flavorant and non-nicotine flavorant each from a separate cartridge chamber 250, 260 as illustrated in FIG. 4C. FIG. 4C is an illustrative ISO view of an exemplary dual cartridge chamber, series arrangement reservoir, vaporization housing 102 and mouthpiece 103 exploded assembly and cut-away partial section view of the series arrangement reservoir, vaporization housing with the cover removed of an embodiment apparatus and/or system. A feature of the system and the apparatus in particular is the ability to independently or simultaneously activate the heating elements (alternatively called heaters herein) of the cartridge chambers in order to provide variable amounts of combined vapor containing nicotine to the user, thus providing the ability to slowly modulate the dispensation of nicotine without altering the vapor characteristic. Vapor generated from one or both heating elements would expand and mix in the vaporization chamber before travelling down the vapor path to the user.

In some embodiments, the multi-chamber release mechanism is configured to independently or simultaneously provide dispensation and vaporization of variable amounts of a nicotine solution and a non-nicotine solution, each from a separate carrier chamber 250, 260, without a flavorant added to either chamber. In some embodiments the flavorant is chosen to impart a smoke, mint, fruit, clove, coffee, tobacco, tea, vanilla, cinnamon, nut, caramel, chocolate, cola, or other flavor to the third vapor. In some embodiments the flavorant comprises a smoke flavor, a mint flavor, a fruit flavor, a clove flavor, a coffee flavor, a tobacco flavor, a tea flavor, a vanilla flavor, a cinnamon flavor, a nut flavor, a caramel flavor, a chocolate flavor, a cola flavor, a or other flavor to the third vapor.

Figure 4D:
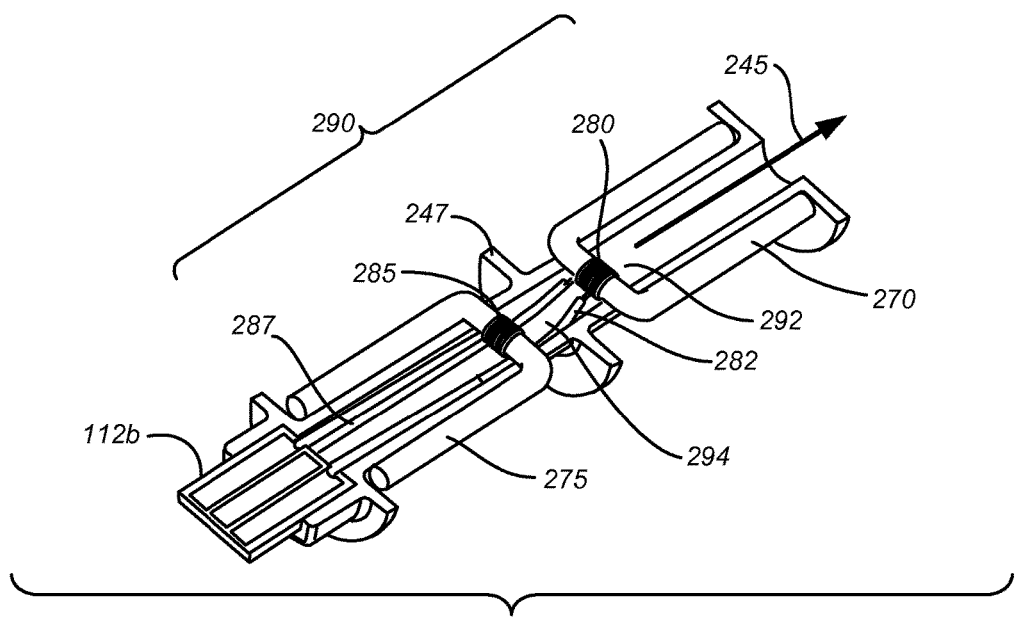
FIG. 4D is an illustrative ISO view of a cut-away section of the series arrangement reservoir, vaporization housing with the cartridge chambers and cover removed of an embodiment apparatus and/or system.
Figure 4E:
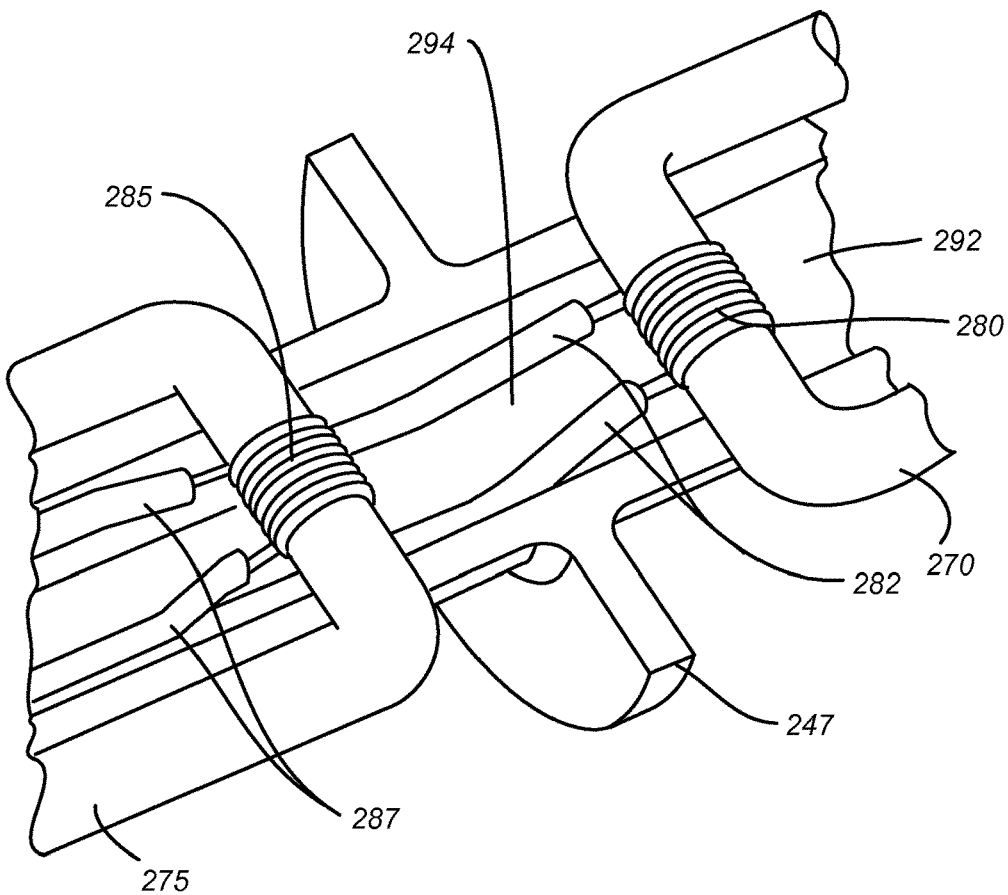
FIG. 4E is an illustrative view of a heater circuit for the series arrangement reservoir, vaporization housing of an embodiment apparatus and/or system.
Figure 4F:
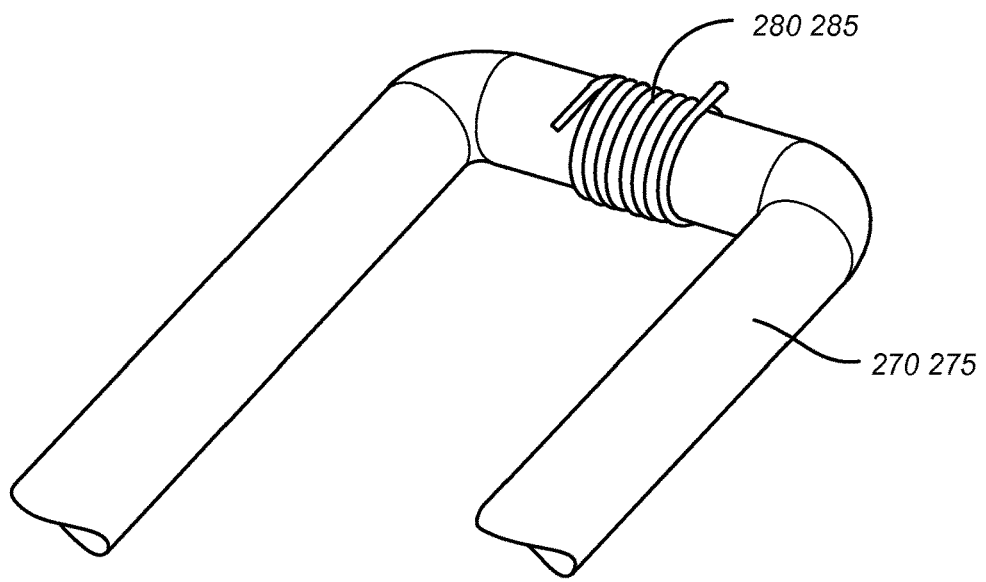
FIG. 4F is an illustrative ISO view of an exemplary heater element and wick for a series arrangement reservoir, vaporization housing of an embodiment apparatus and/or system.

FIG. 4B is an illustrative ISO view of an exemplary dual cartridge chamber, series arrangement reservoir, vaporization housing with the cover removed of an embodiment apparatus and/or system. FIG. 4D is an illustrative ISO view of a cut-away section of the series arrangement reservoir, vaporization housing with the cartridge chambers and cover removed of an embodiment apparatus and/or system. FIG. 4E is an illustrative view of a heater circuit for the series arrangement reservoir, vaporization housing of an embodiment apparatus and/or system. FIG. 4F is an illustrative ISO view of an exemplary heater element (e.g. heater coil in the present figure, but an alternate embodiment could employ a foil heater circuit as the heater element) and wick for a series arrangement reservoir, vaporization housing of an embodiment apparatus and/or system. As illustrated in one or more of FIG. 4B, 4D, 4E or 4F, in some embodiments, the multi-chamber release mechanism 290 of a vaporizer housing 102 comprises, two or more heating elements 280, 285, two or more heating element control circuits 282, 287, two or more wicking elements 270, 275 (alternatively called wick(s) herein); at least one vaporization chamber 292, 294; and at least one vapor flow channel 245. In some embodiments, each one of the two or more wicking elements are in fluid communication with each one of the two or more carrier chambers 250, 260. Each one of the two or more heating elements may be controlled by one of the two or more heating element control circuits attached to a connecting interface 112b and in contact with each wick and in fluid communication with the at least one vaporization chamber wherein formed vapor flows through at least one vaporization chamber to the mouthpiece through the at least one vapor flow channel. The entire chamber release mechanism may be wholly or partially contained in a core 247, wherein the core may be a one-piece construction or a fabricated assembly 247a/247b. In some embodiments, the release mechanism further comprises capacity sensors (not shown) to detect volumes in the carrier chambers.

Provided herein is a programmable electronic vaporizing apparatus 100 comprising: first liquid substance in a first cartridge chamber 160, 260, 360, 460, 560 wherein the first liquid substance comprises nicotine, a second liquid substance in a second cartridge chamber 150, 250, 350, 450, 550 and a vapor release mechanism 290, 390, 490 configured to form a third vapor comprising a first vapor formed from the first liquid substance, a second vapor formed from the second liquid substance, or a combination thereof; and a digital processing device 113, wherein the apparatus changes the third vapor formed by the vapor release mechanism according to instructions provided to the digital processing device 113 from a computer program based on a nicotine management plan.

In some embodiments of the apparatus 100, in order to change the third vapor, the digital processing device 113 is configured to modulate an amount of nicotine in the third vapor according to the nicotine management plan, an amount of nicotine in the first vapor according to the nicotine management plan, an amount of the first liquid substance in the third vapor according to the nicotine management plan, an amount of the first liquid substance in the first vapor according to the nicotine management plan, an amount of the second liquid substance in the third vapor according to the nicotine management plan, an amount of the second liquid substance in the second vapor according to the nicotine management plan, a percentage of the first liquid substance in the third vapor according to the nicotine management plan, a percentage of the second liquid substance in the third vapor according to the nicotine management plan, a percentage of nicotine in the third vapor according to the nicotine management plan, a ratio of the first liquid substance to the second substance in the third vapor according to the nicotine management plan, or a combination thereof.

In some embodiments of the apparatus, the first liquid substance comprises a flavorant. In some embodiments, the second liquid substance comprises nicotine. In some embodiments, the second liquid substance comprises no nicotine. In some embodiments, the second liquid substance comprises a flavorant. In some embodiments, the second liquid substance comprises a non-nicotine liquid. In some embodiments, the non-nicotine liquid is a flavorant. In some embodiments, the non-nicotine liquid is propylene glycol, or 1,3 propanediol. In some embodiments the flavorant is chosen to impart a smoke, mint, fruit, clove, coffee, tobacco, tea, vanilla, cinnamon, nut, caramel, chocolate, cola, or other flavor to the third vapor. In some embodiments the flavorant comprises a smoke flavor, a mint flavor, a fruit flavor, a clove flavor, a coffee flavor, a tobacco flavor, a tea flavor, a vanilla flavor, a cinnamon flavor, a nut flavor, a caramel flavor, a chocolate flavor, a cola flavor, a or other flavor to the third vapor.

FIG. 1A shows an illustrative isometric view of an exemplary electronic vaporizing apparatus assembly and exploded sub-assembly thereof 100 constructed according to the principles of the disclosure. The vaporizing apparatus 100 may be disposable or reusable. The vaporizing apparatus 100 may have a multi-body construction including two or more bodies. For example, the vaporizing apparatus 100 may comprise an attachable durable housing 101 and a second vaporizer housing 102 with or without a mouthpiece 103 and/or the like, that may be easily connected to and disconnected from each other anytime without using any special tools. For example, each housing may include threaded, press fit, bayonette or snap-feature connections 104, 105. Each housing may be covered by a different housing casing 111, 220, 320. The vaporizer housing 102 may contain consumable liquids in separate cartridge chambers, such as, e.g., vaporizing liquid and/or the like. When the consumable liquid is fully consumed, the vaporizer housing 102 may be disconnected from the first durable housing 101 and replaced with a new one. Also, the vaporizer housing 102 may be replaced with another one with a different flavorant and/or the like. Regardless of the construction type, the vaporizing apparatus 100 may have an elongated shape with a first end and a second end, as shown in FIG. 1A, which may be similar to a conventional cigarette shape. Other non-conventional shapes are also contemplated. For example, the vaporizing apparatus 100 may have a cigar or smoking pipe shape or the like.

In some embodiments, the apparatus comprises a first absorbent material (255, 265, 355, 365, 455, 465, 555, 565) in the first cartridge chamber 260, 360, 460, 560, the second cartridge chamber 250, 350, 450, 550, or both.

In some embodiments of the apparatus, the vapor release mechanism 290, 390 is configured to independently or simultaneously vaporize variable amounts of the first liquid substance and the second liquid substance.

In some embodiments of the apparatus, as illustrated in one or more of FIGS. 4B, 4C, 5A & 5B the vapor release mechanism 290, 390 comprises: a first heater 185, 285, 385, 485, coupled to a first wick 175, 275, 375, 475, a second heater 180, 280, 380, 480 coupled to a second wick 170, 270, 370, 470, a first control circuit 287, 387, 487 coupled to the first heater, a second control circuit coupled 282, 382, 482 to the second heater and a first vaporization chamber 190, 292, 294, 393, wherein the first wick is configured to draw the first liquid substance in proximity to or in contact with the first heater, wherein the second wick is configured to draw the second liquid substance in proximity to or in contact with the second heater, and wherein the first heater and second heater are in fluid communication with the first vaporization chamber 190, 294, wherein the first control circuit and the second control circuit are part of the digital processing device 113/117, and wherein the digital processing device is configured to modulate the amount of the first liquid substance drawn by the first wick to the first heater using the first control circuit and to modulate the amount of the second liquid substance drawn by the second wick to the second heater using the second control circuit. The first heater may comprise a first heater coil configured to heat the first liquid substance in the first wick to vaporize the first liquid substance. The second heater may comprise a second heater coil configured to heat the second liquid substance in the second wick to vaporize the second liquid substance. The first heater may comprise a first foil heater circuit configured to heat the first liquid substance in the first wick (alternatively called a first wicking surface) to vaporize the first liquid substance. The second heater may comprise a second foil heater circuit configured to heat the second liquid substance in the second wick (alternatively called a second wicking surface) to vaporize the second liquid substance.

In some embodiments of the apparatus, the vapor release mechanism 290, 390 comprises a first sensor (not shown) that detects a volume of the first liquid substance in the first cartridge chamber. In some embodiments, the vapor release mechanism comprises a second sensor (not shown) that detects a volume of the second liquid substance in the second cartridge chamber.

In some embodiments, the apparatus comprises a vaporizer housing 290, 390 comprising a first cartridge chamber 260, 360, 460, 560 comprising the first cartridge chamber 265, 365, 465, 565 a second cartridge 250, 350, 450, 550 comprising the second cartridge chamber 255, 355, 455, 555, and the vapor release mechanism 290, 390, 490, or a third cartridge comprising the first cartridge chamber 160, the second cartridge chamber 150, and the vapor release mechanism 190.

Figure 5A:
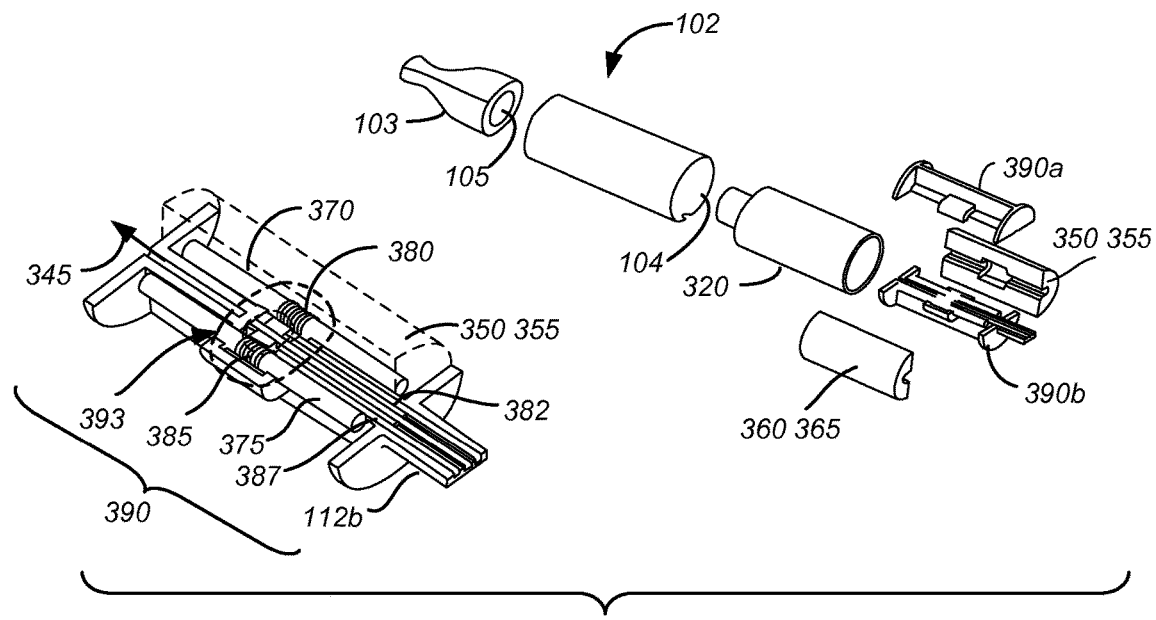
FIG. 5A is an illustrative ISO view of a configuration of an exemplary dual cartridge chamber, parallel arrangement reservoir, vaporization housing and mouthpiece exploded assembly and cut-away partial section view of the parallel arrangement reservoir, vaporization housing with the cover removed of an embodiment apparatus and/or system.
Figure 5B:
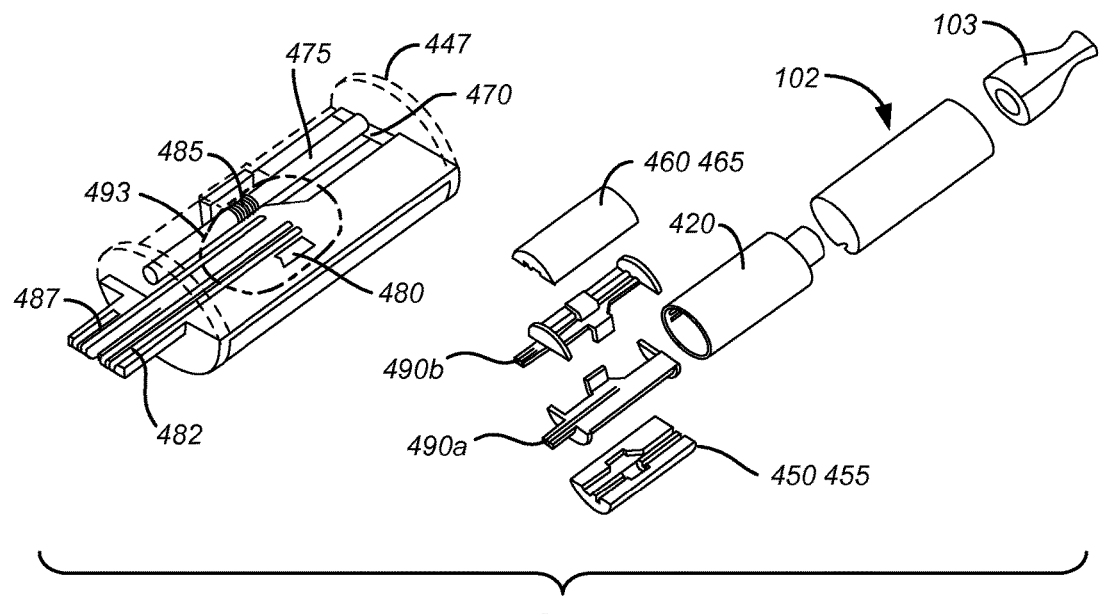
FIG. 5B is an illustrative ISO view of a configuration of an exemplary dual cartridge chamber, parallel arrangement reservoir, vaporization housing and mouthpiece exploded assembly and cut-away partial section view of the parallel arrangement reservoir, vaporization housing with the cover removed of an embodiment apparatus and/or system.

FIG. 5A is an illustrative ISO view of a configuration of an exemplary dual cartridge chamber, parallel arrangement reservoir, vaporization housing and mouthpiece exploded assembly and cut-away partial section view of the parallel arrangement reservoir, vaporization housing with the cover removed of an embodiment apparatus and/or system. FIG. 5B is an illustrative ISO view of a configuration of an exemplary dual cartridge chamber, parallel arrangement reservoir, vaporization housing and mouthpiece exploded assembly and cut-away partial section view of the series arrangement reservoir, vaporization housing with the cover removed of an embodiment apparatus and/or system. In the embodiment of FIG. 5B or of FIG. 5A the apparatus comprises a vaporization chamber casing 320, 420, a vapor release mechanism 390, 490 fabricated from a core 447 assembly comprising a first wicking component 390a, 490b associated with a first cartridge 360, 460 and a second wicking component 390b, 490a associated with the second cartridge 350, 450, and air flow inlet (not shown) creating an internal airflow path 345 running through a combined vaporizer chamber 393, 493.

In some embodiments, entire chamber release mechanism may be wholly or partially contained in a core 347, wherein the core may be a one-piece construction of fabricated assembly 347a/347b. In some embodiments, the multi-chamber release mechanism further comprises capacity sensors (not shown) to detect volumes in the carrier chambers. Additionally, an airflow inlet 340 is located near the connecting interface with a corresponding flow path 345 flowing through the core. In some embodiments of the system, the electronic vaporizing apparatus comprises a first absorbent material in the first cartridge chamber 355, a second absorbent material the second cartridge chamber 365, or a first absorbent material in the first cartridge chamber 355 and a second absorbent material the second cartridge chamber 365. The first absorbent material and the second absorbent material may be the same material with the same properties and/or arrangement within its chamber, the same material with differing properties and/or arrangement within its chamber, or different materials with the same or different arrangements between the chambers.

In some embodiments, the apparatus comprises a durable housing 101 comprising the digital processing device 113 or a portion thereof.

In some embodiments of the apparatus, the durable housing 101 is coupled integrally with or removably from the vaporizer housing 102.

In some embodiments of the apparatus, as illustrated in FIG. 3B, the digital processing device 113 comprises a printed circuit assembly (PCA) 117 comprising; an electronic interface connection 112a (part of 112), a flow sensor analyzer 123, an energy control circuit 121, and a memory 122 for storing the computer program for providing instruction to the digital processing device. In some embodiments, the apparatus comprises a battery input/output 124, an override button 125 and/or a charger input (e.g. from micro-USB) 127.

In some embodiments of the apparatus, the printed circuit assembly 117 further comprises: a microprocessor 129, an electronic communication system 130 for communicating with other electronic devices, and an antenna 128. In some embodiments of the system, the microprocessor is configured to control the communication and program input/output functions of the system. In some embodiments, the communication platform for communicating with other electronic devices comprises: wireless communication links such as Bluetooth 130 and Infrared (IR), (not shown), wired communication links such as micro-USB 144 (among many others), and combinations thereof, wherein the other electronic devices comprise: computers, mobile devices, computer networks, and electronic storage data devices. Additionally, in some embodiments, the apparatus is configured with software for a variety of intranet, internet/web applications.

In some embodiments of the apparatus, the energy control circuit 121 is configured to produce either a simple pulse or a Pulse Width Modulation output signal as illustrated in FIG. 3C configured to individually meter electrical power delivered to the first heater 185, the second heater 180, or both; control a first temperature of the first heater 185, a second temperature of the second heater 180, or both; and control a first rate of production of the first vapor, a second rate of production of the second vapor, or a third rate of production of the third vapor.

In some embodiments, the apparatus is configured to change the third vapor for any given puff, according to the nicotine management plan. In some embodiments of the apparatus, a vaporization chamber volume of the vaporization chamber corresponds to a typical puff volume. Or to the user's typical puff volume. In some embodiments, the vaporization chamber volume of the vaporization chamber is greater than a typical puff volume or the user's typical puff volume, as described elsewhere herein.

In some embodiments of the apparatus the durable housing component 101 may have alternate internal configurations, as illustrated in FIGS. 1B/2B and 1C. As shown in FIGS. 1B and 2B, the durable housing comprises an outer housing (101) and an inner casing 111 to provided added protection of the battery/power source 114. Alternatively, the inner casing may be of a one-piece (111) or multi-piece (111a/111b) construction. The programmable electronic controller, also known as a programmable electronic controller 113 can be comprise a series of assembled components such as a flex circuit connecting the battery 114, LED indicators 126 and charging circuit 119 to the remaining electronic components, or it may comprise a single printed circuit assembly (PCA) 117 with individual mounting features 115 for select features such as LED indicators 126 or override buttons 125 and Molex connectors 116 to accommodate interface connections 112.

As noted in any one of FIG. 1B, 1C, 2A, 3A or 3B, in some embodiments of the apparatus, the printed circuit assembly 117 comprises: an electronic interface connection 112 (112a+112b), a flow sensor analyzer 123, an energy control circuit 121, and a memory 122 for storing a programmable logic. In some embodiments, connectors such as Molex connectors 116 are employed to provide interface connections between components.

In some embodiments of the apparatus, the digital processing device (DPD), 113 or the PCA 117, or the combined DPD with a PCA, further comprises a microprocessor 129 configured to control communication platforms and input/output program functions for the apparatus; an electronic communication platform 130 for communicating with other electronic devices and an antenna 128.

In some embodiments, the programmable electronic controller or DPD is further configured with an energy control circuit 121 configured to produce either a simple pulse or a Pulse Width Modulation (PWM) output signal, as illustrated in FIG. 3C to individually meter the electrical power delivered to the two or more heating elements 180, 185 in the multi-chamber release mechanism, thus controlling the heating element temperature and the rate of vapor production, wherein the simple pulse or PWM output signal is capable of controlling the amount of nicotine dispensed in vapor for any given puff, over a period of time.

In some embodiments of the apparatus, the durable housing 101 comprises at least one of: a power source 114; a connection interface 112 (112*a*) configured to connect the durable housing 102 to the vaporizer housing 102; an LED 126; a battery contact 119*a*; and a charging interface circuit 119 as illustrated in FIGS. 2A and 2B.

In some embodiments, the apparatus is configured to change the percentage of nicotine in the third vapor from about 0% to about 100%, from 0% to 100%, from about 0.01% to about 99.99%, from 0.01% to 99.99%, from about 0.05% to about 99.95%, from about 0.1% to about 99.9%, from 0.1% to about 99.9%, from about 0.5% to about 99.5%, from 0.5% to 99.5%, from about 0% to about 90%, from 0% to 90%, from about 0% to about 80%, from 0% to 80%, from about 0% to about 75%, from 0% to 75%, from about 0% to about 10%, from 0% to 10%, from about 0.01% to about 10%, from 0.01% to 10%, from about 0% to about 25%, from 0% to 25%, from about 0.01% to about 25%, and/or from 0.01% to 25%.

In some embodiments, the percentage of nicotine in the third vapor can be adjusted in increments of 100%, 50%, 40%, 35%, 30%, 25%, 20%, 15%, 10%, 9%, 8%, 7%, 7.5%, 6%, 5%, 4%, 3%, 2%, 1%, 0.5%, 0.1%, 0.05%, 0.01%, about 100%, about 50%, about 40%, about 35%, about 30%, about 25%, about 20%, about 15%, about 10%, about 9%, about 8%, about 7%, about 7.5%, about 6%, about 5%, about 4%, about 3%, about 2%, about 5%, about 1%, about 0.5%, about 0.1%, about 0.05%, about 0.01%, less than 100%, less than 50%, less than 20%, less than 10%, less than 5%, less than 1%, less than 0.5%, less than 0.1%, less than 0.05%, less than 0.01%, greater than about 100%, greater than about 50%, greater than about 20%, greater than about 10%, greater than about 5%, greater than about 1%, greater than about 0.5%, greater than about 0.1%, greater than about 0.05%, and greater than about 0.01%.

In some embodiments of the apparatus, the digital processing device 113/117 comprises on-board memory 122 configured to store an operating system configured to perform the instructions for operating the vapor release mechanism 290, 390, 490; and record a first set of data and a second set of data.

Figure 7A:
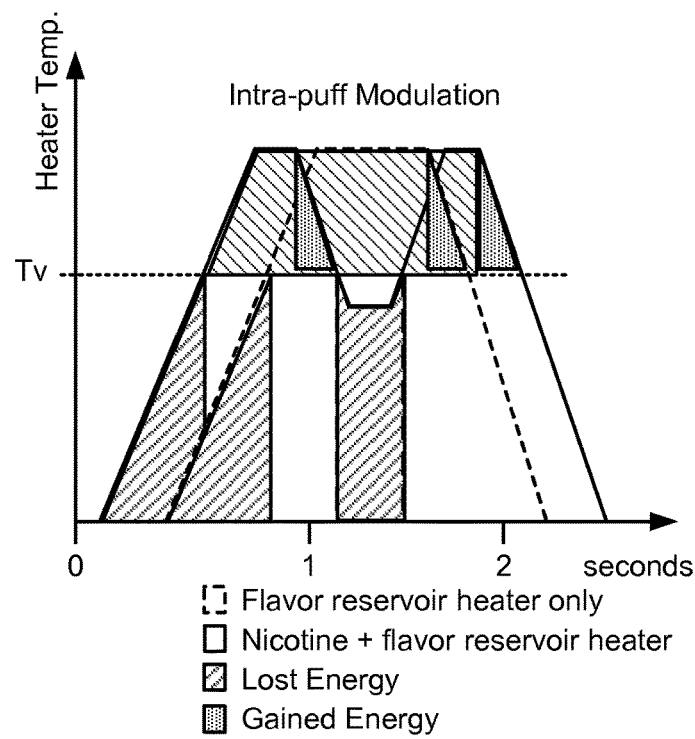
FIG. 7A is an illustrative graph demonstrating the energy utilization of the vapor release mechanism when running in the Intra-puff modulation mode with two heating circuits of an embodiment apparatus and/or system.
Figure 7B:
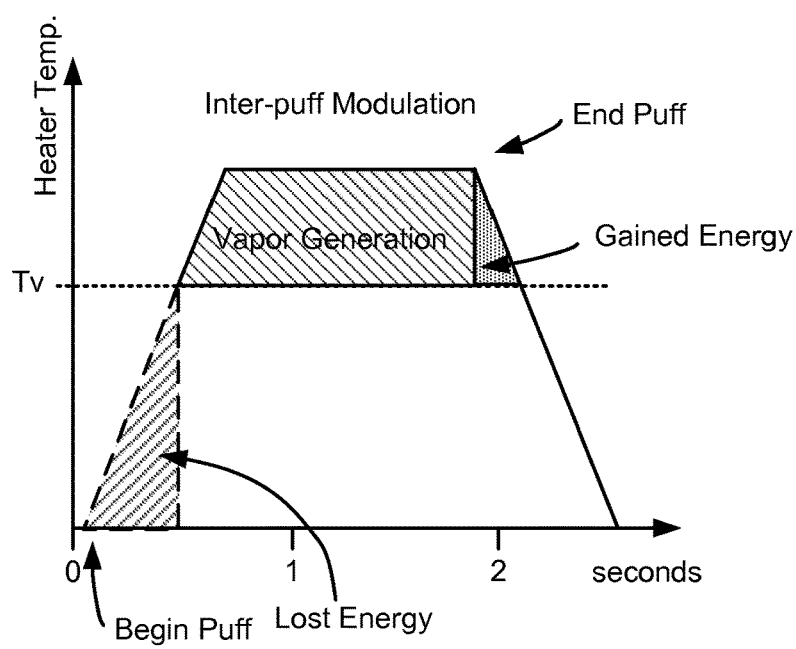
FIG. 7B is an illustrative graph demonstrating the energy utilization of the vapor release mechanism when running in the Inter-puff modulation mode with one heating circuit of an embodiment apparatus and/or system.

In some embodiments, the first set of data comprises vaporization a characteristic comprising one or more of: a first power reading of power delivered to the first heater, a second power reading of power delivered to the second heater, a first duration of energization delivered to the first heater, a second duration of energization delivered to the second heater, and a simple pulse signal profile or a pulse width modulation signal profile. Examples of these profiles are illustrated in FIGS. 7A and 7B.

Figure 9A:
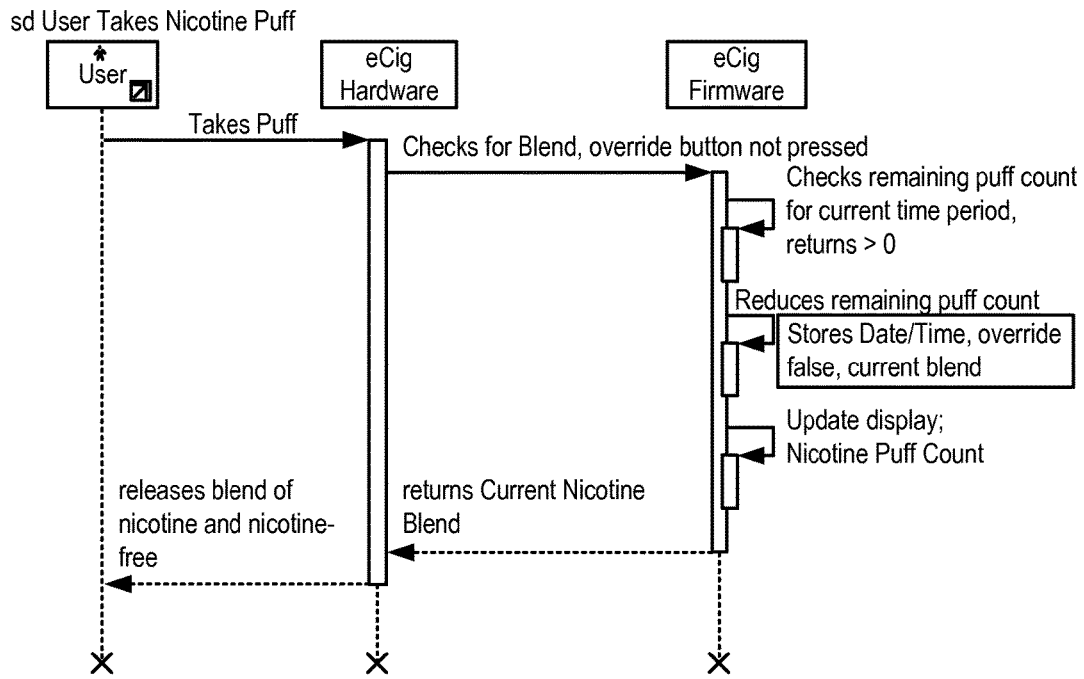
FIG. 9A is an illustrative graphic demonstrating a nicotine logic sequence diagram for an embodiment nicotine management plan.
Figure 9B:
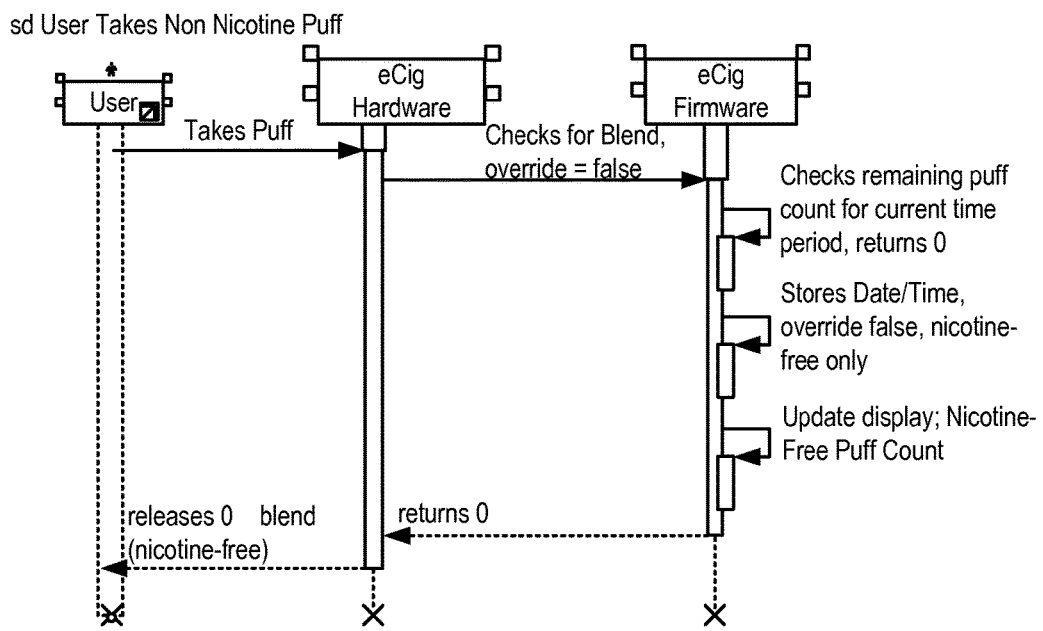
FIG. 9B is an illustrative graphic demonstrating a non-nicotine logic sequence diagram for an embodiment nicotine management plan.
Figure 9C:
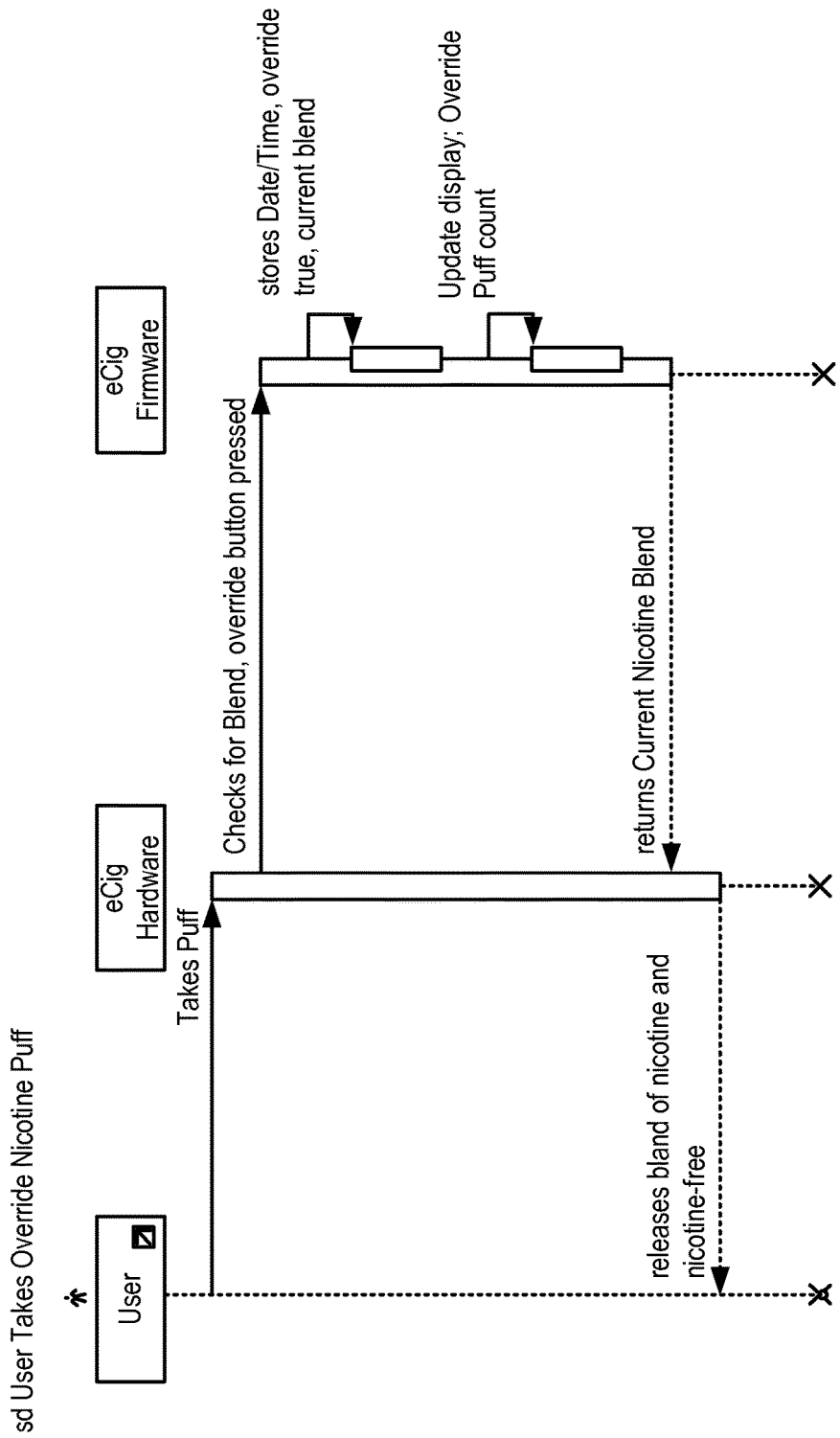
FIG. 9C is an illustrative graphic demonstrating a nicotine override logic sequence diagram for an embodiment nicotine management plan.

In some embodiments of the apparatus, the flow sensor analyzer 123 is configured to detect and record a second set of data comprising one or more of: a date of each user puff; a time of each user puff; a duration of each user puff; an amount of nicotine released to a user; a puff flow; a puff intensity; and an airflow rate within the vapor release mechanism 290. Examples of the logic sequences associated with this data are illustrated in FIGS. 9A-9C.

In some embodiments of the apparatus, the digital processing device 113/117 comprises on-board memory 122 and wherein the second set of data is stored in the on-board memory.

In some embodiments of the apparatus, the vaporizer housing 102 is configured to receive an attachable mouthpiece 103. In some embodiments, the mouthpiece 103 is replaceable. In some embodiments, the vaporizer housing 102 is replaceable.

In some embodiments of the apparatus, the digital processing device 113/117 is configured to execute the instructions defined by the computer program based on the nicotine management plan wherein the vapor release mechanism 290 produces the third vapor having a consistent characteristic regardless of the ratio of the first vapor to the second vapor.

In some embodiments of the apparatus, the characteristic comprises measurable amounts of nicotine in the third vapor or measurable percentage of nicotine in the third vapor generated by the electronic vaporizing apparatus. FIGS. 8A and 8B represent non-limiting examples of the modulating effect of an illustrative nicotine management plan utilized with the apparatus. FIG. 8A is an illustrative example of nicotine modulation that can occur with an embodiment nicotine management plan over a specified duration period of an embodiment system. FIG. 8B is an illustrative of a sample nicotine equivalence delivered to a user of the system with an embodiment nicotine management plan over a specified duration period. Alternative management plans are contemplated herein. For non-limiting example, a management plan may comprise rapid tapering which reduces a user's nicotine from their current usage amount (based on number of cigarettes the user consumes daily, or based on amount of nicotine the user consumes consume daily), or from a pre-selected usage rate (in number of cigarettes consumed per day, number of puffs taken per day, amount of nicotine consumed per day, or based on a starting amount of nicotine allowed daily unrelated to the current user's cigarette habit, for example) to no nicotine in a week, in two weeks, in three weeks, in four weeks, in five weeks, in six weeks, in seven weeks, in up to eight weeks, in one month, in two weeks to two months, or in two weeks to one month. For non-limiting example, a management plan may comprise a medium rate tapering which reduces a user's nicotine from their current usage amount (based on number of cigarettes the user consumes daily, or based on amount of nicotine the user consumes consume daily), or from a pre-selected usage rate (in number of cigarettes consumed per day, number of puffs taken per day, amount of nicotine consumed per day, or based on a starting amount of nicotine allowed daily unrelated to the current user's cigarette habit, for example) to no nicotine in a two months, in eight weeks, in nine weeks, in ten weeks, in eleven weeks, in up to twelve weeks, or in two months to three months. For non-limiting example, a management plan may comprise a long rate tapering which reduces a user's nicotine from their current usage amount (based on number of cigarettes the user consumes daily, or based on amount of nicotine the user consumes consume daily), or from a pre-selected usage rate (in number of cigarettes consumed per day, number of puffs taken per day, amount of nicotine consumed per day, or based on a starting amount of nicotine allowed daily unrelated to the current user's cigarette habit, for example) to no nicotine in three months, in twelve weeks, in thirteen weeks, in fourteen weeks, in fifteen weeks, in sixteen weeks, in seventeen weeks, in eighteen weeks, in three months to six months, in three months to four months, in three months to five months, or in up to six months. For non-limiting example, a management plan may comprise a extended rate tapering which reduces a user's nicotine from their current usage amount (based on number of cigarettes the user consumes daily, or based on amount of nicotine the user consumes consume daily), or from a pre-selected usage rate (in number of cigarettes consumed per day, number of puffs taken per day, amount of nicotine consumed per day, or based on a starting amount of nicotine allowed daily unrelated to the current user's cigarette habit, for example) to no nicotine in over six months, in twenty-six to 52 weeks, or six months to one year, or up to one year. Longer plans may be used, or shorter plans may alternatively be used. As used herein, a "month" is a calendar month, 30 days, or 4 weeks. As used herein, a "year" is 365 days, or 52 weeks. As used herein, "six months" is 26 weeks, or 182 days.

In some embodiments of the system and/or apparatus, the vapor characteristic produced with each puff comprise: vapor intensity (measurable as vapor flow rate), vapor volume, vapor density (measured by spectrophotometry methods known to one of skill in the art), vapor flavor, and/or oral sensation, wherein the characteristic is consistent irrespective of nicotine levels. In some embodiments of the system and/or apparatus, the vapor characteristic produced with each puff comprises vapor intensity (measurable as vapor flow rate). In some embodiments of the system and/or apparatus, the vapor characteristic produced with each puff comprises vapor volume. In some embodiments of the system and/or apparatus, the vapor characteristic produced with each puff comprises vapor density (measured by spectrophotometry methods known to one of skill in the art). In some embodiments of the system and/or apparatus, the vapor characteristic produced with each puff comprises vapor flavor, and/or oral sensation.

In some embodiments, the apparatus comprises an override feature 125, configurable to override the digital processing device 113/117 to modify the amount or percentage of the nicotine dispensed. In some embodiments, the override feature is manual. In some embodiments, the override feature is automatic.

In some embodiments of the apparatus, the override feature comprises: a button 125; a sensor; a touch pad; a microphone; an infrared (IR) device; and/or a Bluetooth device.

In some embodiments of the apparatus, the microprocessor 129 is configured to control communication systems 130 and input/output program functions for the apparatus.

In some embodiments of the apparatus, the electronic communication system 130 for communicating with one or more other electronic device comprises a wireless communication link 130 and/or a wired communication link 144, wherein the other electronic device comprises: a computer, a mobile device, a computer network and an electronic storage data device; a non-limiting example of which is illustrated in FIG. 11.

In some embodiments of the apparatus 100, the first cartridge chamber 260 and the second chamber 250 are in series arrangement as illustrated in FIG. 4B, are in parallel arrangement as illustrated in FIG. 6A, and/or comprise a central vapor flow path 145 through a vaporization chamber 190 common to the first cartridge 160 and the second cartridge150 as illustrated in FIG. 4A.

As shown in FIG. 4A, the cartridge chambers for the vaporizer housing 102 illustrate a dual cartridge, series arrangement with nicotine and non-nicotine cartridge chambers 150, 160, wicks 170, 175 and heating elements 180, 185 aligned in a series arrangement, with a vaporization chamber 190 arranged therebetween and in fluid communication with an airflow inlet 140, 240 and vapor flow outlet path 145 to a mouthpiece 103. The apparatus also illustrates an electrical connector 112b by which electrical current may be selectively transmitted to the individual heating elements to provide precise control over the vaporization temperature applied to each wick. In this arrangement, the chamber can be circumferential and stacked on top of each other. The order of the chambers does not matter. The nicotine chamber 150 could be on top or bottom, as could the non-nicotine chamber 160. An illustrative example of such an arrangement is shown in FIG. 4B.

In some embodiments, the multi-chamber vapor release mechanism is configured to independently or simultaneously provide the dispensation and vaporization of variable amounts of the nicotine and a flavorant and non-nicotine flavorant each from a separate cartridge chamber 250, 260 as illustrated in FIG. 4C. As will be further illustrated below, a key feature of the system and the apparatus in particular is the ability to independently or simultaneously activate the heating elements of the cartridge chambers in order to provide variable amounts of combined vapor containing nicotine to the user, thus providing the ability to slowly modulate the dispensation of nicotine without altering the vapor characteristic. Vapor generated from one or both heating elements would expand and mix in the vaporization chamber before travelling down the vapor path to the user. In some embodiments, the flavorant comprises 1,2 propanediol (propylene glycol) and/or 1,3 propanediol. In some embodiments, the flavorant comprises 1,2 propanediol (propylene glycol) and/or 1,3 propanediol and/or another vapor forming substance.

In some embodiments, the multi-chamber release mechanism is configured to independently or simultaneously provide dispensation and vaporization of variable amounts of a nicotine solution and a non-nicotine solution, each from a separate carrier chamber 250, 260, without a flavorant added to either chamber.

As illustrated in any one of FIG. 4B, 4D, 4E or 4F, in some embodiments, the multi-chamber release mechanism 290 of a vaporizer housing 102 comprises, two or more heating elements 280, 285, two or more sets of heating element control circuits 282, 287, two or more wicking elements 270, 275; at least one vaporization chamber 292, 294; and at least one vapor flow channel 245, wherein each one of the two or more wicking elements are in fluid communication with each one of the two or more carrier chambers 250, 260, each one of the two or more heating elements are controlled by one of the two or more sets of heating element control circuits attached to a connecting interface 112b and in contact with each wick and in fluid communication with the at least one vaporization chamber wherein formed vapor flows through at least one vaporization chamber to the mouthpiece through the at least one vapor flow channel. The entire chamber release mechanism may be wholly or partially contained in a core 247, wherein the core may be a one-piece construction of fabricated assembly 247a/247b. In some embodiments, the multi-chamber release mechanism further comprises capacity sensors (not shown) to detect volumes in the carrier chambers. Additionally, an airflow inlet 240 is located near the connecting interface with a corresponding flow path 245 flowing through the core. Cartridge chamber fill ports 241 may also be located at either end of the assembly.

In some embodiments of the apparatus, the durable housing 101 comprises at least one of: a power source 114, a vaporizing housing connection interface 104 configured to connect the durable housing 101 to the vaporizer housing 102, a connecting interface 112 (112a & 112b) configured to connect the durable housing digital processing device circuit to the vaporizer housing circuit, an LED 126, a battery contact 119a, and a charging interface circuit 119, as illustrated in FIGS. 2A and 2B.

In some embodiments of the apparatus, the power source comprises: a disposable battery 114 a rechargeable battery, wherein said rechargeable battery is configured with an optional battery charging mechanism 127, an external charging station, and/or a solar cell.

In some embodiments, the durable housing has an end cap 118, comprising capture features 137 and 138, and configurable to allow the charging circuit 119 to be moved, allowing for the removal of the battery 114, as illustrated in FIG. 2B.

Provided herein is a method of using the a programmable smoking cessation system comprising an electronic nicotine vaporizing apparatus described above, comprising modulating over time and according to a nicotine management plan an amount of nicotine in the third vapor or percentage of nicotine in the third vapor generated by the electronic vaporizing apparatus, wherein a first concentration of nicotine in the first liquid substance is fixed.

Provided herein is a method of using the programmable electronic vaporizing apparatus described above, comprising modulating over time and according to a nicotine management plan an amount of nicotine in the third vapor or percentage of nicotine in the third vapor generated by the electronic vaporizing apparatus, wherein a first concentration of nicotine in the first liquid substance is fixed.

In some embodiments of the method with the system or the apparatus, wherein modulating comprises implementing a rate of nicotine reduction in the third vapor over time that is controlled by the computer program and the nicotine management plan in combination with the digital processing device, thereby changing a ratio of first vapor to second vapor in the third vapor over time.

In some embodiments, the rate of nicotine reduction with the system comprises: a linear reduction, a logarithmic reduction, a stepped reduction, or a combination thereof, wherein the rate of nicotine reduction is measured in percentage of nicotine per time period.

In some embodiments of the method of using the system the nicotine management plan comprises the steps: A1.) establishing a frequency for the number of puffs for a given amount or percentage of nicotine delivered over a first period of time multiplied by a second period of time, B1.) maintaining said frequency for the number of puffs and decrementing the amount or percentage of nicotine delivered by a specified amount for said first period of time multiplied by said second period of time, C1.) repeating step B1.) until the amount or percentage of nicotine delivered=0, and continuing to next step, D1.) maintaining the amount or percentage of 0 nicotine for a third period of time, or until the user stops using the system.

In some embodiments of the method using the system, the nicotine management plan comprises the steps: A2.) establishing a frequency for the number of puffs for a given amount or percentage of nicotine delivered over a first period of time multiplied by a second period of time, B2.) changing said frequency for the number of puffs and decrementing the amount or percentage of nicotine delivered by a specified amount for said first period of time multiplied by said second period of time, C2.) repeating step B2.) until the amount or percentage of nicotine delivered=0, and continuing to next step, D2.) maintaining the amount or percentage of 0 nicotine for a third period of time, or until the user stops using the system.

In some embodiments of the method with the apparatus, the rate of nicotine reduction comprises: a linear reduction, a logarithmic reduction, stepped reduction, or a combination thereof, wherein the rate of nicotine reduction is measured in percentage of nicotine per time period.

In some embodiments of the method with the apparatus, the nicotine management plan comprises the steps: a1.) establishing a frequency for the number of puffs for a given amount or percentage of nicotine delivered over a first period of time multiplied by second period of time, b1.) maintaining said frequency for the number of puffs and decrementing the amount or percentage of nicotine delivered by a specified amount for said first period of time multiplied by said second period of time, c1.) repeating step b1.) until the amount or percentage of nicotine delivered=0, and continuing to next step, d1.) maintaining the amount or percentage of 0 nicotine for a third period of time, or until the user stops using the device.

In some embodiments of the method with the apparatus, the nicotine management plan comprises the steps: a2.) establishing a frequency for the number of puffs for a given amount or percentage of nicotine delivered over a first period of time multiplied by second period of time, b2.) changing said frequency for the number of puffs and decrementing the amount or percentage of nicotine delivered by a specified amount for said first period of time multiplied by said second period of time, c2.) repeating step b2.) until the amount or percentage of nicotine delivered=0, and continuing to next step, d2.) maintaining the amount of 0 nicotine for a third period of time, or until the user stops using the device.

In some embodiments of the method with the system or the apparatus, the apparatus comprises an override to allow an additional amount or percentage of nicotine to be dispersed.

In some embodiments, usage of the override can be monitored and tracked. In some embodiments, the override can be disabled. In some embodiments, the override comprises a time delay. In still other embodiments, the override time delay can be: a fixed period of time; a variable period of time; a series of periods of time; a permanent period of time, or any combination thereof.

In some embodiments, the nicotine management plan provides for disablement of the system after a defined period of time following the attainment of an amount or percentage of 0 nicotine delivered.

In some embodiments, the nicotine management plan provides for disablement of the apparatus after a defined period of time following the attainment of an amount or percentage of 0 nicotine delivered.

Provided herein is a method for smoking cessation comprising: providing the any configuration of the a programmable smoking cessation system comprising an electronic nicotine vaporizing apparatus described above and providing a nicotine management plan; wherein the nicotine management plan modulates over time an amount of nicotine in the third vapor or percentage of nicotine in the third vapor generated by the electronic vaporizing apparatus, wherein a first concentration of nicotine in the first liquid substance is fixed.

Provided herein is a method for smoking cessation comprising: providing any configuration of the programmable electronic vaporizing apparatus described above and providing a nicotine management plan, wherein the nicotine management plan modulates over time an amount of nicotine in the third vapor or percentage of nicotine in the third vapor generated by the electronic vaporizing apparatus, wherein a first concentration of nicotine in the first liquid substance is fixed.

In some embodiments of the method using the system or the apparatus, modulating comprises implementing a rate of nicotine reduction in the third vapor over time that is controlled by the computer program and the nicotine management plan in combination with the digital processing device, thereby changing a ratio of first vapor to second vapor in the third vapor over time.

In some embodiments of the method using the system, the rate of nicotine reduction comprises: a linear reduction, a logarithmic reduction, a stepped reduction, or a combination thereof, wherein the rate of nicotine reduction is measured in percentage of nicotine per time period as illustrated by the graphs in FIGS. 8A, 8B.

In some embodiments of the method using the system, the nicotine management plan comprises the steps: A1.) establishing a frequency for the number of puffs for a given amount or percentage of nicotine delivered over a first period of time multiplied by a second period of time, B1.) maintaining said frequency for the number of puffs and decrementing the amount or percentage of nicotine delivered by a specified amount for said first period of time multiplied by said second period of time; C1.) repeating step B1.) until the amount or percentage of nicotine delivered=0, and continuing to next step; D1.) maintaining the amount or percentage of 0 nicotine for a third period of time, or until the user stops using the system.

In some embodiments of the method using the system, the nicotine management plan comprises the steps: A2.) establishing a frequency for the number of puffs for a given amount or percentage of nicotine delivered over a first period of time multiplied by a second period of time; B2.) changing said frequency for the number of puffs and decrementing the amount or percentage of nicotine delivered by a specified amount for said first period of time multiplied by said second period of time; C2.) repeating step B2.) until the amount or percentage of nicotine delivered=0, and continuing to next step; D2.) maintaining the amount or percentage of 0 nicotine for a third period of time, or until the user stops using the system.

In some embodiments of the method using the apparatus, the rate of nicotine reduction comprises: a linear reduction, a logarithmic reduction, a stepped reduction, or a combination thereof, wherein the rate of nicotine reduction is measured in percentage of nicotine per time period as illustrated by the graphs in FIGS. 8A and 8B.

In some embodiments of the method using the apparatus, the nicotine management plan comprises the steps: a1.) establishing a frequency for the number of puffs for a given amount or percentage of nicotine delivered over a first period of time multiplied by second period of time; b1.) maintaining said frequency for the number of puffs and decrementing the amount or percentage of nicotine delivered by a specified amount for said first period of time multiplied by said second period of time; c1.) repeating step b1.) until the amount or percentage of nicotine delivered=0, and continuing to next step; d1.) maintaining the amount or percentage of 0 nicotine for a third period of time, or until the user stops using the apparatus.

In some embodiments of the method using the apparatus, the nicotine management plan comprises the steps: a2.) establishing a frequency for the number of puffs for a given amount or percentage of nicotine delivered over a first period of time multiplied by second period of time; b2.) changing said frequency for the number of puffs and decrementing the amount or percentage of nicotine delivered by a specified amount for said first period of time multiplied by said second period of time; c2.) repeating step b2.) until the amount or percentage of nicotine delivered=0, and continuing to next step; d2.) maintaining the amount of 0 nicotine for a third period of time, or until the user stops using the apparatus.

Examples of the logic for these methods is illustrated in FIGS. 9A-9C.

Provided herein is an electronic vapor release mechanism for a vaporizing apparatus 102 comprising a digital vaporizing chip 600 configured to independently or simultaneously vaporize variable amounts of a first liquid substance and the second liquid substance Various embodiments are illustrated in FIGS. 6A-6E.

Figure 6B:
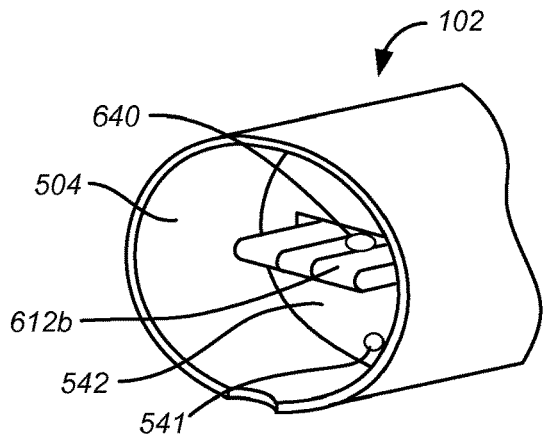
Figure 6B:
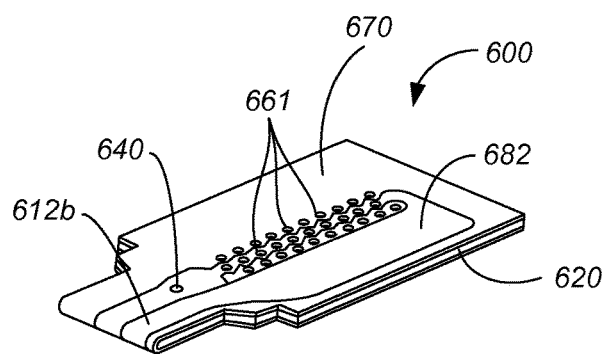
Figure 6C:
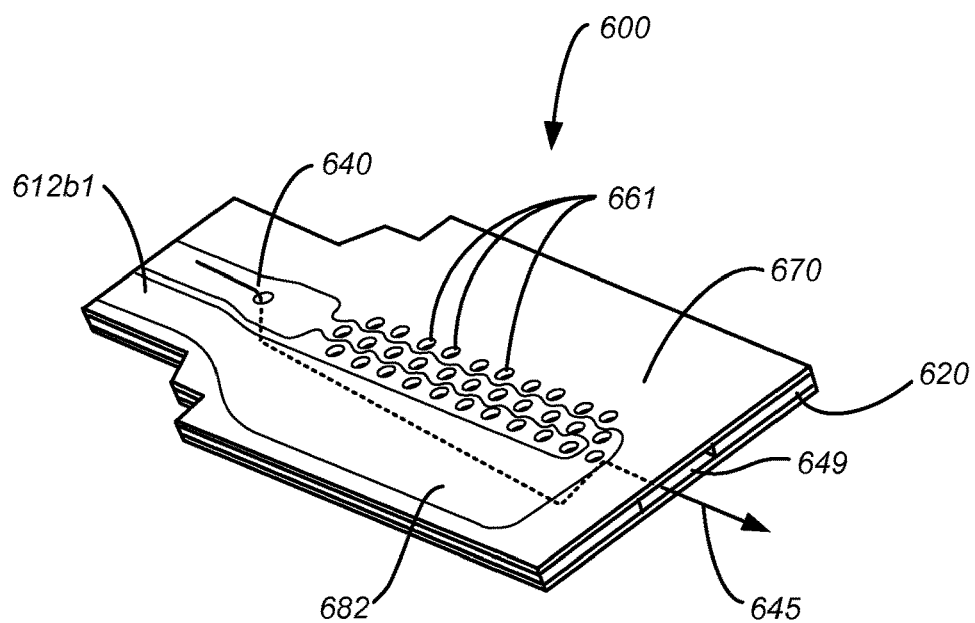
Figure 6C:
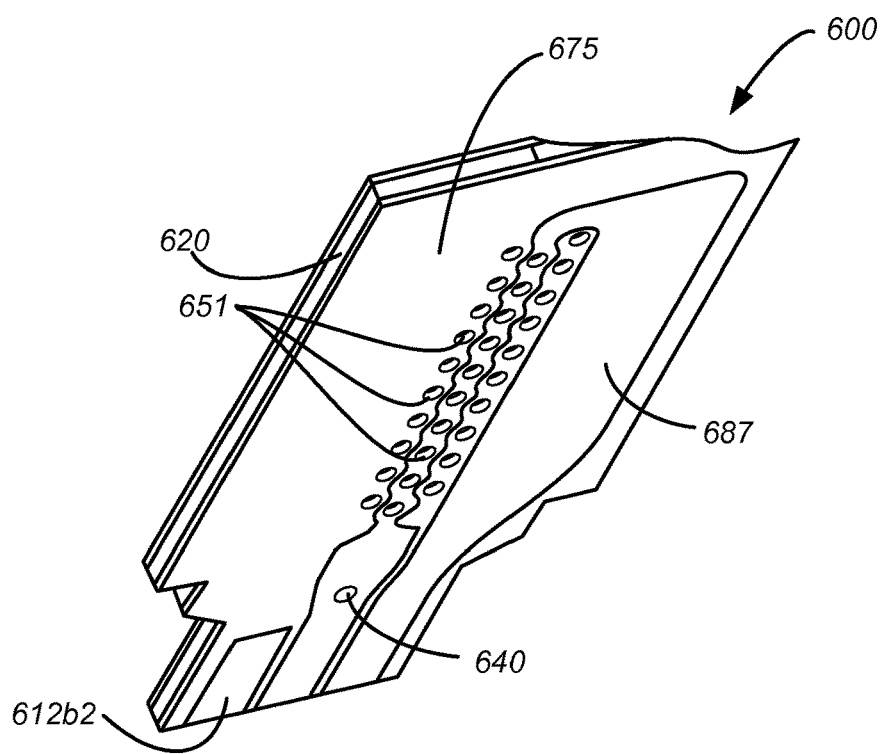
Figure 6D:
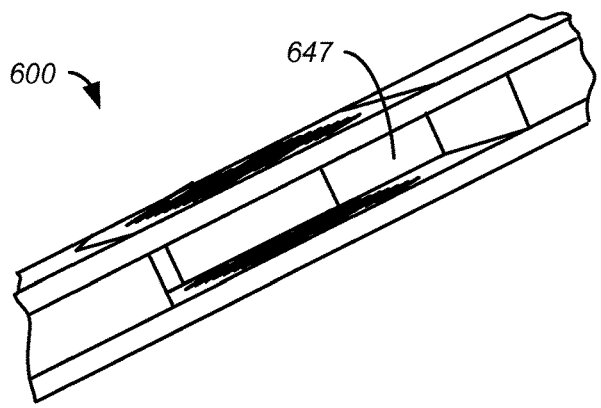
Figure 6D:
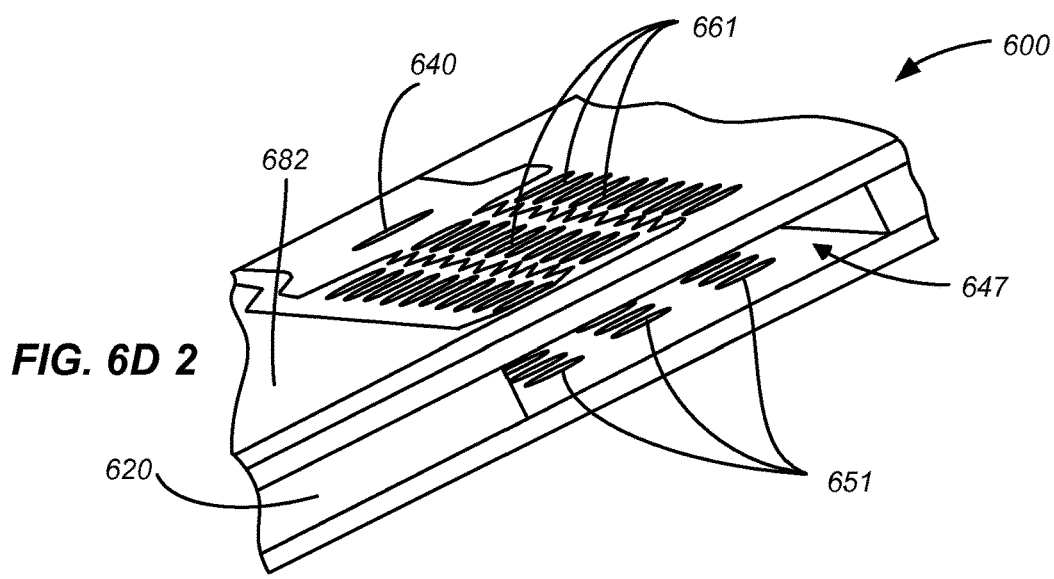
Figure 6D:
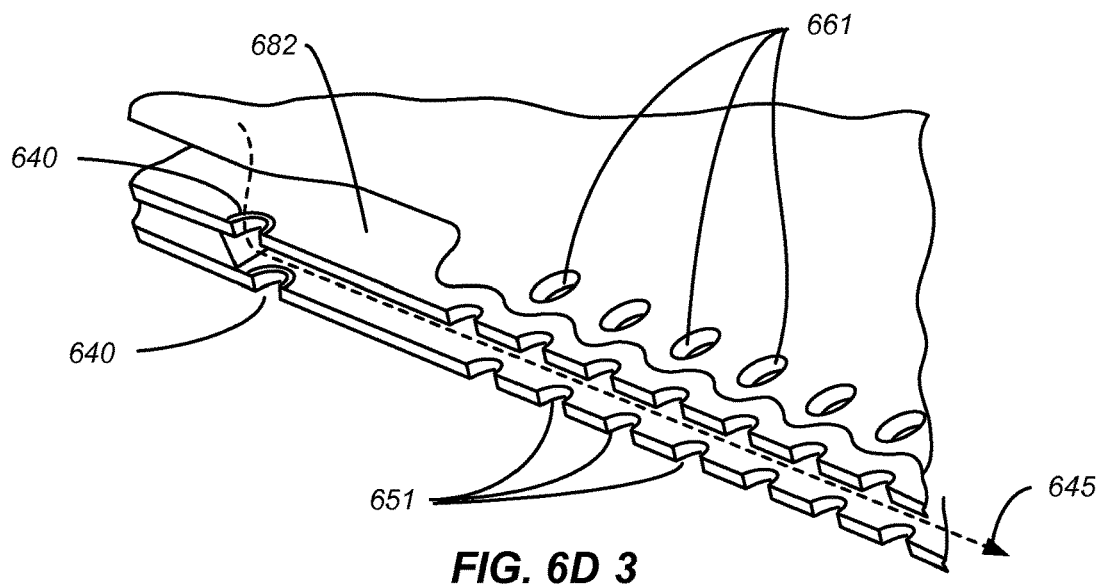
Figure 6E:
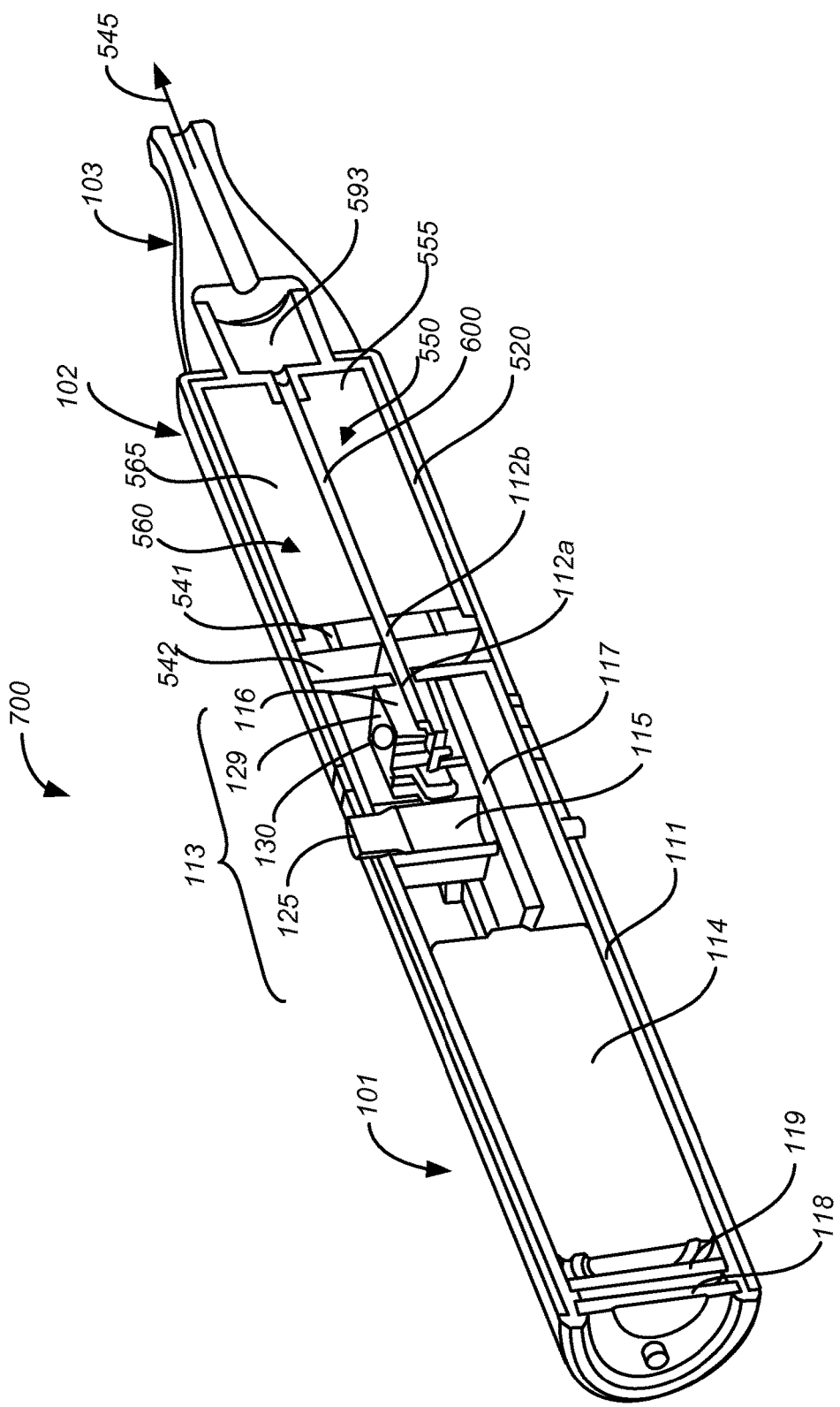
FIG. 6E is an illustrative ISO cross-section view of a dual parallel arrangement cartridge chamber vaporizer assembly with a digital vaporizing chip with a foil heater circuit of an embodiment apparatus and/or system.

FIG. 6A is an illustrative cut-away partial section ISO view of a configuration of an exemplary dual cartridge chamber, parallel arrangement reservoir, vaporization housing and mouthpiece assembly and a digital vaporizing chip with a foil heater circuit of an embodiment apparatus and/or system. FIG. 6B-1 is an illustrative ISO detail end view of the digital vaporizing chip with a foil heater circuit and interconnect feature of FIG. 6A. FIG. 6B-2 is an illustrative ISO view of an embodiment digital vaporizing chip with a foil heater circuit of an embodiment apparatus and/or system. FIG. 6C-1 is an illustrative reverse angle ISO view of an embodiment digital vaporizing chip with a foil heater circuit of FIG. 6B-2. FIG. 6C-2 is an illustrative ISO view of the opposite side of the digital vaporizing chip with a foil heater circuit of FIG. 6C-1. FIG. 6D-1 is an illustrative end ISO detail view of the digital vaporizing chip of FIG. 6B-2 with a foil heater circuit showing the airflow channel between the layers of the digital vaporizing chip. FIG. 6D-2 is a second illustrative end ISO detail view of the a digital vaporizing chip of FIG. 6B-2 with a foil heater circuit showing the airflow channel between the layers of the a digital vaporizing chip and the various wick holes in contact with their respective foil heater circuit. FIG. 6D-3 is an illustrative ISO cross-section detail view of the digital vaporizing chip of FIG. 6B-2 with a foil heater circuit through the airflow channel. FIG. 6E is an illustrative ISO cross-section view of a dual parallel arrangement cartridge chamber vaporizer assembly with a digital vaporizing chip with a foil heater circuit of an embodiment apparatus and/or system.

In some embodiments, as illustrated in FIG. 6A through FIG. 6E, the digital vaporizing chip 600 comprises: a multi-layer circuit board comprising an outermost layer comprising a connecting interface 612b and at least one inner layer of thermal and electrical insulating material 620; a wicking surface 670 located on a portion of the outer-most layer; an airflow channel 647 within or between the layer of thermal and electrical insulating material comprising a closed first end 642 and a second open end comprising an airflow outlet 649; a plurality of wicking holes 661 located about the wicking surface 670 and in fluid communication with the airflow channel 647; a foil heater circuit 682 on the wicking surface in fluid communication with the connecting interface 612b; and an airflow inlet 640 located on the outer-most layer and in fluid communication with the airflow channel; wherein the digital vaporizing chip 600 is configured to interface with a digital processing device and power source configured to control the foil heater circuit which in combination with the wicking surface is in intimate contact with a chamber comprising a vaporizable fluid, wherein vaporization of the vaporizable fluid occurs at the interface between the foil heater circuit and the wicking surface when a current is applied to the foil heater circuit according to instructions provided by the digital processing device, and wherein the formed vapor is drawn through the wicking holes into the airflow channel by a vacuum created when air is drawn through the airflow inlet and pulled out through the airflow outlet, creating an airflow path 645. In some embodiments, the vaporizer housing comprises connection features 504, 503 for attachment to a durable housing and mouthpiece respectively.

As illustrated in the FIGS. 6A-6D-3, in some embodiments of the digital vaporizing chip, the multi-layer flexible printed circuit board 600 comprises a first outermost layer, a second outermost layer, a connecting interface 612b, at least one inner layer of thermal and electrical insulating material 620, at least one foil heater circuit 682, 687, at least one wicking surface 670, 675, at least one wick hole 661, 651, at least one airflow inlet 640, at least one airflow channel 647, and at least one airflow outlet 649, wherein the connecting interface 612b is configured to interface with a digital processing device and a power source providing power to the at least one foil heater circuit 682, 687 which is in intimate contact with the at least one wicking surface 670, 675 and at least one wick hole 661, 651 which are in intimate contact with the vapor-producing medium, wherein air is drawn into the at least one airflow channel 647 through the at least one airflow inlet 640, and formed vapor is drawn through the at least one airflow channel 647 to create an airflow path 645 to the at least one airflow outlet 649, wherein the vapor is drawn out through an expansion vaporization chamber 593.

In some embodiments, the digital vaporizing chip 600 is configured for a vaporizer cartridge 520. In some embodiments, the digital vaporizing chip is disposable. In some embodiments, the vaporizer cartridge is disposable.

Provided herein is a programmable electronic vaporizing apparatus 700 as illustrated in FIG. 6E, comprising: a first liquid substance in a first cartridge chamber 560 wherein the first liquid substance comprises nicotine, a second liquid substance in a second cartridge chamber 550; and a vapor release mechanism comprising a digital vaporizing chip 600 configured to form a third vapor comprising a first vapor formed from the first liquid substance, a second vapor formed from the second liquid substance, or a combination thereof; and a digital processing device 113, wherein the apparatus changes the third vapor formed by the vapor release mechanism according to instructions provided to the digital processing device from a computer program.

In some embodiments of the apparatus 700, in order to change the third vapor, the digital processing device is configured to modulate an amount of nicotine in the third vapor according to the nicotine management plan, an amount of nicotine in the first vapor according to the nicotine management plan, an amount of the first liquid substance in the third vapor according to the nicotine management plan, an amount of the first liquid substance in the first vapor according to the nicotine management plan, an amount of the second liquid substance in the third vapor according to the nicotine management plan, an amount of the second liquid substance in the second vapor according to the nicotine management plan, a percentage of the first liquid substance in the third vapor according to the nicotine management plan, a percentage of the second liquid substance in the third vapor according to the nicotine management plan, a percentage of nicotine in the third vapor according to the nicotine management plan, a ratio of the first liquid substance to the second substance in the third vapor according to the nicotine management plan, or a combination thereof.

In some embodiments, the first liquid substance comprises a flavorant. In some embodiments, the second liquid substance comprises nicotine. In some embodiments the second liquid substance comprises no nicotine. In some embodiments, the second liquid substance comprises a flavorant. In some embodiments, the second liquid substance comprises a non-nicotine liquid. In some embodiments, the non-nicotine liquid is a flavorant.

In some embodiments, the vaporizer housing cartridge 102, comprises two or more carrier chambers 560, 550, an electronic multi-chamber release mechanism comprising a flexible printed circuit foil wick 600, an inner casing 520, a casing/carrier chamber endcap 542, carrier chamber filling ports 541, a vaporization chamber 593, and an airflow path 545 therethrough (see FIG. 6E for example).

In some embodiments, the apparatus comprises a first absorbent material 565, 555 in the first cartridge chamber 560, the second cartridge chamber 550, or both. In some embodiments, the apparatus comprises a first absorbent material 565 in the first cartridge chamber 560, a second absorbent material 555 the second cartridge chamber 550, or both.

In some embodiments of the apparatus, the vapor release mechanism is configured to independently or simultaneously vaporize variable amounts of the first liquid substance and the second liquid substance.

In some embodiments of the apparatus, the digital vaporizing chip 600 comprises a multi-layer circuit board comprising: a first outermost layer comprising a first connecting interface 612b1, a second outermost layer comprising a second connecting interface 612b2, a first inner layer comprising thermal and electrical insulating material 620, a second inner layer comprising thermal and electrical insulating material 620; a first wicking surface 670 located on a portion of the first outer-most layer, a second wicking surface 675 located on a portion of the second outer-most layer; an airflow channel 647 between the first inner layer and second inner layer comprising a closed first end 642 and an open second end comprising an airflow outlet 649; a first plurality of wicking holes 661 located about the first wicking surface in fluid communication with the airflow channel, a second plurality of wicking holes 651 located about the second wicking surface in fluid communication with the airflow channel; a first foil heater circuit 682 on the first wicking surface in fluid communication with the first connecting interface, a second foil heater circuit 687 on the second wicking surface in fluid communication with the second connecting interface; a first airflow inlet 640 located on the first outer-most layer in fluid communication with the airflow channel and a second airflow inlet 640 located on the second outer-most layer in fluid communication with the airflow channel, wherein the first wicking surface is configured to draw the first liquid substance in proximity to or in contact with the first foil heater circuit, wherein the second wicking surface is configured to draw the second liquid substance in proximity to or in contact with the second foil heater circuit, and wherein the first foil heater circuit and second foil heater circuit are in fluid communication with the airflow channel, wherein the first connecting interface 612b1 and the second connecting interface 612b2 are connected to the digital processing device 613, and wherein the digital processing device is configured to modulate the amount of the first liquid substance drawn by the first foil heater circuit 682 using the first connecting interface 612b1 and to modulate the amount of the second liquid substance drawn by the second foil heater circuit 687 using the second connecting interface 612b2.

In some embodiments of the apparatus 700, the vapor release mechanism comprises a first sensor (not shown) that detects a volume of the first liquid substance in the first cartridge chamber. In some embodiments, the vapor release mechanism comprises a second sensor (not shown) that detects a volume of the second liquid substance in the second cartridge chamber.

In some embodiments, the apparatus comprises a vaporizer housing 102 comprising a first cartridge chamber comprising 560 the first cartridge chamber 565, a second cartridge 550 comprising the second cartridge chamber 555, and the vapor release mechanism 600, or a third cartridge 520 comprising the first cartridge chamber 565, the second cartridge chamber 555, and the vapor release mechanism 600.

In some embodiments, the apparatus comprises a durable housing 101 comprising the digital processing device 113 or a portion thereof.

In some embodiments, the durable housing 101 is coupled integrally with or removably from the vaporizer housing 102.

In some embodiments of the system the durable housing component 101 may have alternate internal configurations, as illustrated in FIG. 6E. The apparatus comprises an outer housing (101) and an inner casing 111 to provided added protection of the battery/power source 114. Alternatively, the inner casing may be of a one-piece (111) or multi-piece (111a/111b) construction. The programmable electronic controller 113 can comprise a series of assembled components such as a flex circuit connecting the battery 114, LED indicators 126 and charging circuit 119 to the remaining electronic components, or it may comprise a single printed circuit assembly (PCA) 117 with individual mounting features 115 for select features such as LED indicators 126, communication platforms such as Bluetooth 130, or override buttons 125 and Molex connectors 116 to accommodate interface connections 112 (112a/112b). In some embodiments, the printed circuit assembly comprises a battery input/output 124 and a charger input 127. In some embodiments, the housing has an end cap 118. In some embodiments, the end cap 118 has an indicator LED cover.

In some embodiments of the apparatus, the digital processing device (DPD) 113 also known as a programmable electronic controller, comprises a printed circuit assembly (PCA) 117 comprising: an electronic interface connection 112a, a flow sensor analyzer 123, an energy control circuit 121, and a memory 122 for storing the computer program.

In some embodiments of the apparatus, the DPD 113 or programmable electronic controller is configured to execute instructions according to instructions defined by a software program for a specific nicotine modulation protocol wherein, the components of the vaporizer housing produce a vapor having a consistent characteristic, and a nicotine concentration which is gradually diminished over a specified timeframe.

As illustrated in FIGS. 9A-9C, the digital processing device 113 is configured to monitor each puff taken on the apparatus and compare that data with the instructions defined by a software program for a specific nicotine modulation protocol. For example, FIGS. 9A & 9B illustrate the software routines for evaluation of nicotine and non-nicotine vapor, wherein the flow sensor analyzer compares the intensity of the puff, along with the amount of nicotine and non-nicotine vapor delivered, as well as the count sequence allowed within the selected routine of the nicotine management plan. The puff count is then updated for the current time period, the remaining allowable puff count is decremented, the data is stored in the memory, and the apparatus then releases the appropriate blend of nicotine and non-nicotine vapor.

In some embodiments of the system and/or apparatus, the vapor characteristic produced with each puff comprise: vapor intensity (measurable as vapor flow rate), vapor volume, vapor density (measured by spectrophotometry methods known to one of skill in the art), vapor flavor, and/or oral sensation, wherein the characteristic is consistent irrespective of nicotine levels. In some embodiments of the system and/or apparatus, the vapor characteristic produced with each puff comprises vapor intensity (measurable as vapor flow rate). In some embodiments of the system and/or apparatus, the vapor characteristic produced with each puff comprises vapor volume. In some embodiments of the system and/or apparatus, the vapor characteristic produced with each puff comprises vapor density (measured by spectrophotometry methods known to one of skill in the art). In some embodiments of the system and/or apparatus, the vapor characteristic produced with each puff comprises vapor flavor, and/or oral sensation.

In some embodiments of the apparatus, the printed circuit assembly further comprises: a microprocessor 129, an electronic communication system 130 for communicating with other electronic devices, and an antenna 128.

In some embodiments of the apparatus, the energy control circuit 121 is configured to produce either a simple pulse or a Pulse Width Modulation output signal configured to individually meter electrical power delivered to the first foil heater circuit 682, the second foil heater circuit 687, or both; control a first temperature of the first foil heater circuit, a second temperature the second foil heater circuit, or both; and control a first rate of production of the first vapor, a second rate of production of the second vapor, or a third rate of production of the third vapor.

In some embodiments, the apparatus is configured to change the third vapor for any given puff, according to the nicotine management plan.

In some embodiments of the apparatus, a vaporization chamber volume of the vaporization chamber corresponds to a typical puff volume. In some embodiments the vaporization chamber volume is greater than the puff volume. In some embodiments, a typical puff volume is about 15 ml to about 175 ml, about 20 ml to about 150 ml, about 15 ml to about 100 ml, about 15 ml to about 75 ml, about 20 ml to about 75 ml, about 25 ml to about 50 ml, about 25 ml, about 35 ml, about 40 ml, about 45 ml, about 50 ml, about 60 ml, 15 ml to 175 ml, 20 ml to 150 ml, 15 ml to 100 ml, 15 ml to 75 ml, 20 ml to 75 ml, 25 ml to 50 ml, 25 ml, 35 ml, 40 ml, 45 ml, 50 ml, or 60 ml. In some embodiments, the user's own typical puff volume is determined by system, or the user's own typical puff volume is provided to the system and used to adjust the nicotine in the third vapor (as amount or percentage) over time according to the management plan.

In some embodiments of the apparatus 700, the digital processing device 113 comprises on-board memory 122 configured to: store an operating system configured to perform the instructions; and record a first set of data and a second set of data.

In some embodiments of the apparatus 700, the first set of data comprises vaporization characteristics comprising one or more of: a first power reading of power delivered to the first foil heater circuit, a second power reading of power delivered to the second foil heater circuit, a first duration of energization delivered to the first foil heater circuit, a second duration of energization delivered to the second foil heater circuit, and a simple pulse signal profile or a pulse width modulation signal profile.

As illustrated in FIG. 7A, the graph represents a way of visually expressing the energy requirements of a dual-vaporizer system. It illustrates that there is a significant amount of lost energy while the user heats up the vaporizable solution until it finally reaches its vaporization temperature. And when there are two vaporizers (to achieve the "intra-puff" nicotine modulation (amount/percentage), the amount of lost energy during this part of the process is doubled.

As illustrated in FIG. 7B, the graph illustrates the energy requirements of the "inter-puff" method of nicotine modulation; the process of energizing just one coil at a time, but doing so in a varying frequency proportion between nicotine and flavor-only vaporizers. For example, one may begin by energizing the electronic vaporizing apparatus all the time, but eventually decrementing the sequence to only 4 out of 5 puffs to achieve 80% nicotine amount; followed by only 3 out of 5 puffs to achieve 60% nicotine amount, etc. In summary, the estimated energy requirements of a dual-vaporizer system will be less than the power required to operate two heating elements simultaneously, but more than just one heating element alone.

In some embodiments of the apparatus, the flow sensor analyzer 123 is configured to detect and record a second set of data comprising one or more of: a date of each user puff, a time of each user puff, a duration of each user puff, an amount of nicotine released to a user, a puff flow, a puff intensity, and an airflow rate within the vapor release mechanism.

In some embodiments of the apparatus, the digital processing device 113 comprises on-board memory 122 and wherein the second set of data is stored in the on-board memory.

In some embodiments of the apparatus 700, the vaporizer housing 102 is configured to receive an attachable mouthpiece 103. In some embodiments, the mouthpiece is replaceable. In some embodiments, the vaporizer housing is replaceable.

In some embodiments of the apparatus 700, the digital processing device 113 is configured to execute the instructions defined by the computer program based on the nicotine management plan wherein the vapor release mechanism produces the third vapor having a consistent characteristic regardless of the ratio of the first vapor to the second vapor.

In some embodiments of the apparatus, the nicotine management plan gradually diminishes the amount or percentage of nicotine in the third vapor over a specified period of time.

In some embodiments of the apparatus, the characteristic comprises measurable amounts of nicotine in the third vapor or measurable percentage of nicotine in the third vapor generated by the electronic vaporizing apparatus.

In some embodiments, the apparatus comprises an override feature 125, configurable to override the digital processing device 113 to modify the amount or percentage of the nicotine dispensed. In some embodiments, the override feature is manual. In some embodiments, the override feature is automatic.

FIG. 9C illustrates a routine, wherein the user may choose to use an override feature, allowing an additional does of nicotine to be delivered to the user, outside of the specific nicotine tapering protocol chosen by the user. This feature is provided as a safety mechanism, since some embodiments of the system and/or apparatus allow a user to have a momentary lapse in the management plan versus allowing the user to revert back to his or her former means of nicotine intake. In this case the flow sensor analyzer compares the intensity of the puff, along with the amount of excess nicotine vapor delivered, as well as the date, time and count sequence within the selected routine of the nicotine management plan. The Override puff count is then updated for the current time period, the remaining normal allowable puff count is decremented, the data is stored in the memory, and the apparatus then releases the appropriate blend of nicotine and non-nicotine vapor to the user.

Figure 10A:
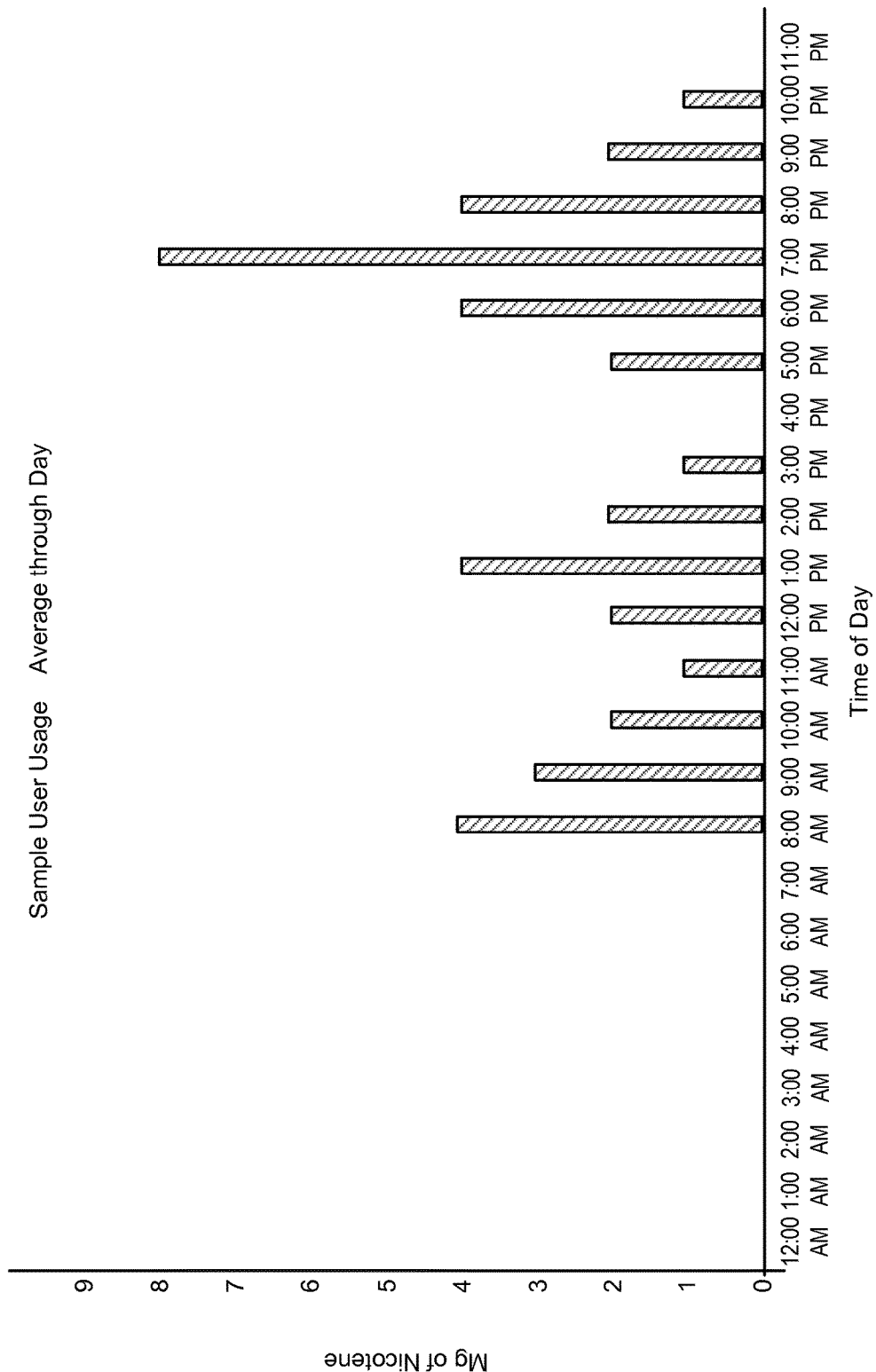
FIG. 10A is an illustrative graphic demonstrating a sample of user's daily frequency data output for nicotine intake when using an embodiment nicotine management plan.
Figure 10B:
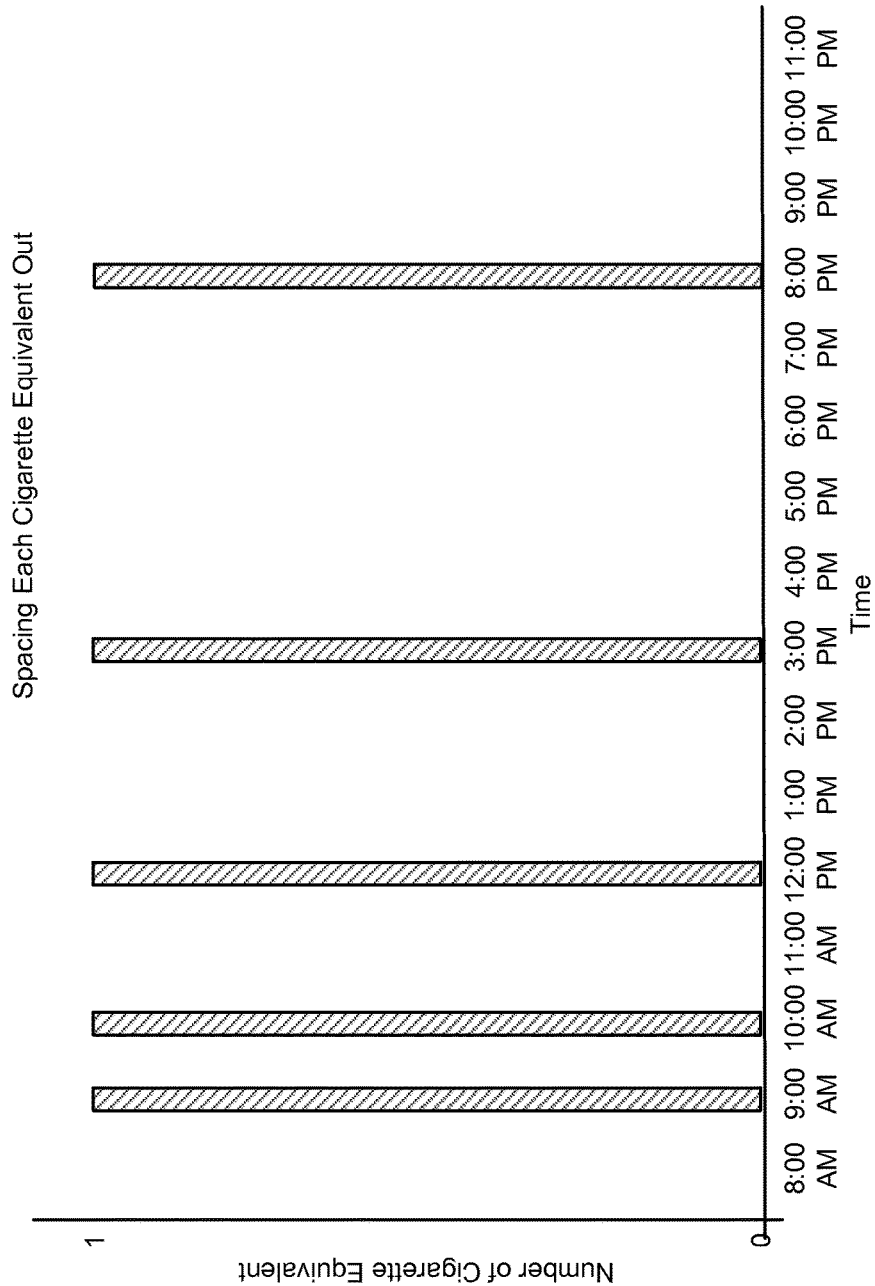
FIG. 10B is an illustrative graphic demonstrating a sample of user's daily inter-puff spacing data of an embodiment nicotine management plan.

FIGS. 10A & 10B illustrate graphic outputs showing the user's daily frequency data output for nicotine intake and a user's daily inter-puff spacing data for one of the nicotine modulating management protocols. This data is just a small representative sample of data that is stored and can be shared with the user and or a clinical professional.

In some embodiments of the apparatus 700, the override feature 125 comprises: a button, a sensor, a touch pad, a microphone, an infrared (IR) device, and/or a Bluetooth device.

In some embodiments of the apparatus, the microprocessor 129 is configured to control communication systems 130 and input/output program functions for the apparatus.

In some embodiments of the apparatus 700, the electronic communication system for communicating with one or more other electronic device comprises: a wireless communication link 130; and a wired communication link 144, wherein the other electronic device comprises: a computer, a mobile device, a computer network, and an electronic storage data device, as illustrated in FIG. 11.

In some embodiments of the apparatus, the first cartridge chamber 560/565 and the second cartridge chamber 550/555 are in series arrangement, are in parallel arrangement, and/or comprise a central vapor flow path 545 (alternatively referred to as an air flow path herein) through a vaporization chamber 593 common to the first cartridge and the second cartridge.

In some embodiments of the apparatus 700, the durable housing 101 comprises at least one of: a power source 114, a connection interface 104 configured to connect the durable housing to the vaporizer housing, an LED 126, a battery contact 119a, and a charging interface circuit 119.

In some embodiments of the apparatus 700, the power source comprises: a disposable battery 114, a rechargeable battery, wherein said rechargeable battery is configured with an optional battery charging mechanism 119, an external charging station (not shown), and/or a solar cell (not shown).

In some embodiments of the apparatus, the durable housing further comprises: a vaporization housing connection interface 112a; and a removable end cap 118, as illustrated in FIG. 1B.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An electronic vaporizing apparatus comprising:
   a first liquid substance in a first cartridge chamber wherein the first liquid substance comprises nicotine;
   a second liquid substance in a second cartridge chamber;
   a vapor release mechanism comprising:
      a first heater coupled to a first wick,
      a second heater coupled to a second wick,
      a first control circuit coupled to the first heater,
      a second control circuit coupled to the second heater, and
      a first vaporization chamber,
      the vapor release mechanism configured to generate a third vapor comprising a first vapor formed from the first liquid substance drawn from the first cartridge chamber by the first wick and heated by the first heater as controlled by the first control circuit, a second vapor formed from the second liquid substance drawn from the second cartridge chamber by the second wick and heated by the second heater as controlled by the second control circuit, or a combination thereof; and
   a digital processing device comprising non-transitory computer readable storage media encoded with a program including instructions executable by an operating system to control a constant rate of nicotine reduction over time according to a nicotine management plan for a user of the electronic vaporization apparatus;
   wherein the first wick is configured to draw the first liquid substance in proximity to or in contact with the first heater,
   wherein the second wick is configured to draw the second liquid substance in proximity to or in contact with the second heater,
   wherein the first heater and second heater are in fluid communication with the first vaporization chamber,
   wherein the first control circuit and the second control circuit are part of the digital processing device, and
   wherein the apparatus generates the constant third vapor formed by the vapor release mechanism according to the instructions based on the nicotine management plan, which limits the amount or rate or percent of nicotine the user can intake for a given time.

2. The electronic vaporizing apparatus of claim 1, wherein the first liquid substance further comprises a flavorant.

3. The electronic vaporizing apparatus of claim 1, wherein the second liquid substance comprises a flavorant or a non-nicotine liquid.

4. The electronic vaporizing apparatus of claim 1, wherein the electronic vaporizing apparatus comprises a first absorbent material in the first cartridge chamber, the second cartridge chamber, or both.

5. The electronic vaporizing apparatus of claim 1, wherein the vapor release mechanism is configured to independently or simultaneously vaporize variable amounts of the first liquid substance and the second liquid substance.

6. The electronic vaporizing apparatus of claim 1, comprising a vaporizer housing comprising:
   a first cartridge comprising the first cartridge chamber, a second cartridge comprising the second cartridge chamber, and the vapor release mechanism, or
   a third cartridge comprising the first cartridge chamber, the second cartridge chamber, and the vapor release mechanism.

7. The electronic vaporizing apparatus of claim 1, wherein the electronic vaporizing apparatus further comprises a durable housing comprising the digital processing device or a portion thereof and wherein the durable housing is coupled integrally with or removably from the vaporizer housing.

8. The electronic vaporizing apparatus of claim 1, wherein the digital processing device is configured to execute the instructions defined by the computer program based on the nicotine management plan wherein the vapor release mechanism produces the third vapor having a consistent characteristic regardless of the ratio of the first vapor to the second vapor, and
   wherein the characteristic comprises:
      measureable amounts of nicotine in the third vapor or measurable percentage of nicotine in the third vapor generated by the electronic vaporizing apparatus; or
      measureable amounts of flavorant in the third vapor or measurable percentage of flavorant in the third vapor generated by the electronic vaporizing apparatus.

9. The electronic vaporizing apparatus of claim 1, wherein the nicotine management plan gradually diminishes the amount or percentage of nicotine in the third vapor over a specified period of time.

10. The electronic vaporizing apparatus of claim 1,
    wherein the digital processing device is configured to modulate the amount of the first liquid substance drawn by the first wick to the first heater using the first control circuit and to modulate the amount of the second liquid substance drawn by the second wick to the second heater using the second control circuit.

11. The electronic vaporizing apparatus of claim 10, wherein the vapor release mechanism detects a volume of the first liquid substance in the first cartridge chamber.

12. The electronic vaporizing apparatus of claim 10, wherein the vapor release mechanism detects a volume of the second liquid substance in the second cartridge chamber.

13. The electronic vaporizing apparatus of claim 1, wherein the digital processing device is configured for modulating the rate or amount of nicotine delivery and comprises a printed circuit assembly comprising:
    an electronic interface connection;
    an energy control circuit; and
    a memory for storing the computer program.

14. The electronic vaporizing apparatus of claim 13, wherein the printed circuit assembly further comprises:
    a microprocessor;
    an electronic communication system for communicating with other electronic devices; and
    an antenna;
    wherein the microprocessor is configured to control communication systems and input/output program functions for the apparatus, and
    wherein the electronic communication system comprises:
    a wireless communication link; and
    a wired communication link, and
    wherein the other electronic devices comprise:
    a computer;
    a mobile device;
    a computer network; and
    an electronic storage data device.

15. The electronic vaporizing apparatus of claim 13, wherein the energy control circuit is configured to produce either a simple pulse or a Pulse Width Modulation output signal configured to:

independently or simultaneously meter electrical power delivered to the first heater, the second heater, or both;

independently or simultaneously control a first temperature of the first heater, a second temperature the second heater, or both; and independently or simultaneously control a first rate of production of the first vapor, a second rate of production of the second vapor, or a third rate of production of the third vapor.

16. The electronic vaporizing apparatus of claim 1, wherein the digital processing device comprises on-board memory configured to:

store an operating system configured to perform the instructions; and record a first set of data and a second set of data.

17. The electronic vaporizing apparatus of claim 16, wherein the first set of data comprises:

vaporization characteristics comprising one or more of;
 a first power reading of power delivered to the first heater,
 a second power reading of power delivered to the second heater,
 a first duration of energization delivered to the first heater,
 a second duration of energization delivered to the second heater, and
 a simple pulse signal profile or a pulse width modulation signal profile.

18. The electronic vaporizing apparatus of claim 16, wherein the digital processing device is configured to digitally determine and record the second set of data comprising one or more of:

a date of each user puff;
a time of each user puff;
a duration of each user puff;
an amount of nicotine released to a user;
a puff flow;
a puff intensity; and
an airflow rate within the vapor release mechanism.

19. The electronic vaporizing apparatus of claim 1, the digital processing device providing instruction to the vapor release mechanism to modulate:

an amount of nicotine in the third vapor according to the instructions provided by the program based on the nicotine management plan, an amount of nicotine in the first vapor according to the instructions provided by the program based on the nicotine management plan, an amount of the first liquid substance in the third vapor according to the instructions provided by the program based on the nicotine management plan, an amount of the first liquid substance in the first vapor according to the instructions provided by the program based on the nicotine management plan, an amount of the second liquid substance in the third vapor according to the instructions provided by the program based on the nicotine management plan, an amount of the second liquid substance in the second vapor according to the instructions provided by the program based on the nicotine management plan, a percentage of the first liquid substance in the third vapor according to the instructions provided by the program based on the nicotine management plan, a percentage of the second liquid substance in the third vapor according to the instructions provided by the program based on the nicotine management plan, a percentage of nicotine in the third vapor according to the instructions provided by the program based on the nicotine management plan, a ratio of the first liquid substance to the second substance in the third vapor according to the instructions provided by the program based on the nicotine management plan, or a combination thereof.

20. The electronic vaporizing apparatus of claim 19, wherein the system is configured to change the third vapor for any given puff, according to the nicotine management plan, and wherein a vaporization chamber volume of the vaporization chamber corresponds to a typical puff volume.

21. The electronic vaporizing apparatus of claim 19, wherein the system is configured to change the percentage of nicotine in the third vapor from about 0% to about 100%, from 0% to 100%, from about 0.01% to about 99.99%, from 0.01% to 99.99%, from about 0.05% to about 99.95%, from about 0.1% to about 99.9%, from 0.1% to about 99.9%, from about 0.5% to about 99.5%, from 0.5% to 99.5%, from about 0% to about 90%, from 0% to 90%, from about 0% to about 80%, from 0% to 80%, from about 0% to about 75%, from 0% to 75%, from about 0% to about 10%, from 0% to 10%, from about 0.01% to about 10%, from 0.01% to 10%, from about 0% to about 25%, from 0% to 25%, from about 0.01% to about 25%, or from 0.01% to 25%.

22. The electronic vaporizing apparatus of claim 21, wherein the percentage of nicotine in the third vapor can be adjusted in increments of 100%, 50%, 40%, 35%, 30%, 25%, 20%, 15%, 10%, 9%, 8%, 7%, 7.5%, 6%, 5%, 4%, 3%, 2%, 1%, 0.5%, 0.1%, 0.05%, 0.01%, about 100%, about 50%, about 40%, about 35%, about 30%, about 25%, about 20%, about 15%, about 10%, about 9%, about 8%, about 7%, about 7.5%, about 6%, about 5%, about 4%, about 3%, about 2%, about 1%, about 0.5%, about 0.1%, about 0.05%, about 0.01%, less than 100%, less than 50%, less than 20%, less than 10%, less than 5%, less than 1%, less than 0.5%, less than 0.1%, less than 0.05%, less than 0.01%, greater than about 100%, greater than about 50%, greater than about 20%, greater than about 10%, greater than about 5%, greater than about 1%, greater than about 0.5%, greater than about 0.1%, greater than about 0.05%, or greater than about 0.01%.

23. A method of using the electronic vaporizing apparatus of claim 1, comprising:

modulating over time and according to the nicotine management plan, an amount of nicotine in the third vapor or a percentage of nicotine in the third vapor generated by the electronic vaporizing apparatus, a first concentration of nicotine being fixed, said modulating comprises implementing a rate of nicotine reduction in the third vapor over time that is controlled by the computer program and the nicotine management plan in combination with the digital processing device, thereby changing a ratio of the first vapor to the second vapor in the third vapor over time, the rate of nicotine reduction comprises:
 a linear reduction;
 a logarithmic reduction;
 a stepped reduction; or
 a combination thereof; and the rate of nicotine reduction is measured in percentage of nicotine per time period.

* * * * *